(12) United States Patent
Carroll et al.

(10) Patent No.: US 9,977,024 B2
(45) Date of Patent: May 22, 2018

(54) TARGETED COVALENT PROBES AND INHIBITORS OF PROTEINS CONTAINING REDOX-SENSITIVE CYSTEINES

(71) Applicant: THE SCRIPPS RESEARCH INSTITUTE, La Jolla, CA (US)

(72) Inventors: Kate S. Carroll, Jupiter, FL (US); Vinayak Gupta, Jupiter, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days. days.

(21) Appl. No.: 14/650,772

(22) PCT Filed: Dec. 8, 2013

(86) PCT No.: PCT/US2013/073765
§ 371 (c)(1),
(2) Date: Jun. 9, 2015

(87) PCT Pub. No.: WO2014/089546
PCT Pub. Date: Jun. 12, 2014

(65) Prior Publication Data
US 2016/0195532 A1    Jul. 7, 2016

Related U.S. Application Data

(60) Provisional application No. 61/735,058, filed on Dec. 9, 2012.

(51) Int. Cl.
*G01N 33/573*    (2006.01)
*C12Q 1/37*    (2006.01)
*C12Q 1/42*    (2006.01)
*C12N 9/99*    (2006.01)
*A61K 31/517*    (2006.01)
*A61K 31/425*    (2006.01)

(52) U.S. Cl.
CPC ......... *G01N 33/573* (2013.01); *A61K 31/425* (2013.01); *A61K 31/517* (2013.01); *C12N 9/99* (2013.01); *C12Q 1/37* (2013.01); *C12Q 1/42* (2013.01); *G01N 2333/916* (2013.01); *G01N 2500/04* (2013.01); *G01N 2500/20* (2013.01)

(58) Field of Classification Search
CPC .................................................... G01N 33/50
See application file for complete search history.

(56) References Cited

FOREIGN PATENT DOCUMENTS

WO    WO 2005/026156 A1    3/2005
WO    WO 2005/105761 A1    11/2005

OTHER PUBLICATIONS

Leonard et al., Redox-Based Probes for Protein Tyrosine PhosphatasesAngewandte Chemie, International Edition (2011), 50(19), 4423-4427.*
Leonard et al., ACS Chemical Biology (2009), 4(9), 783-799.*
Ajmani et al., Chemical Biology & Drug Design (2009), 74(6), 582-595.*
Hang, et al., "Mechanism-Based Probe for the Analysis of Cathepsin Cysteine Proteases in Living Cells" *ACS Chemical Biology* 1 (11): 713-723 (2006).
Paulsen, et al., "Peroxide-dependent sulfenylation of the EGFR catalytic site enhances kinase activity", *Nature Chemical Biology* 8 (1): 57-64 (2012).
Reddie, et al., "A chemical approach for detecting sulfenic acid-modified proteins in living cells", *Mol Biosyst* 4 (6); 521-531 (2008).
Leonard, et al., "Mining the Thiol Proteome for Sulfenic Acid Modifications Reveals New Targets for Oxidation in Cells", *ACS Chemical Biology* 4 (9): 783-799 (2009).
Leonard, et al., "Redox-Based Probes for Protein Tyrosine Phosphatases", *Angew. Chem. Int. Ed.* 50; 4423-4427 (2011).

* cited by examiner

*Primary Examiner* — Paul V Ward
(74) *Attorney, Agent, or Firm* — Geoffrey K. Cooper; Thomas Fitting

(57) ABSTRACT

Covalent, irreversible small-molecule inhibitors that modify the sulfenyl form (i.e., sulfenic acid, RSOH and sulfenamide, RSNR'2) of therapeutically important proteins (particularly kinases and phosphatases) are disclosed, where the compositions include a compound having a substituted aryl or heterocyclic core structure that promotes binding interactions with a specific protein, and a nucleophilic reaction center (carbon, nitrogen, sulfur, or phosphorous) that is capable of forming a covalent bond with a sulfenic acid- or sulfenamide-modified cysteine residue in the protein. Methods for synthesizing these compounds are also disclosed, as well as methods of using them for determining the bioactivity of a chemical composition comprising an active compound toward a specific protein and for determining the potency of an inhibitor against a specific protein.

9 Claims, 29 Drawing Sheets

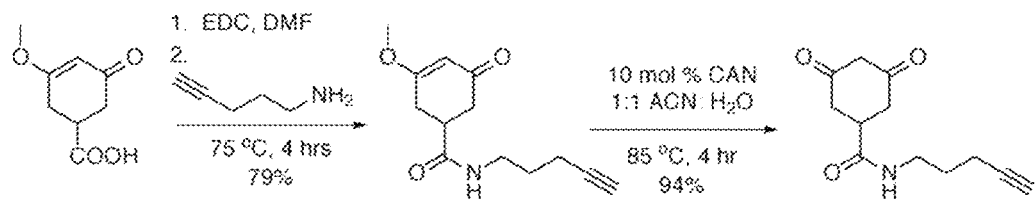
Scheme 1: Synthesis of DYn-0
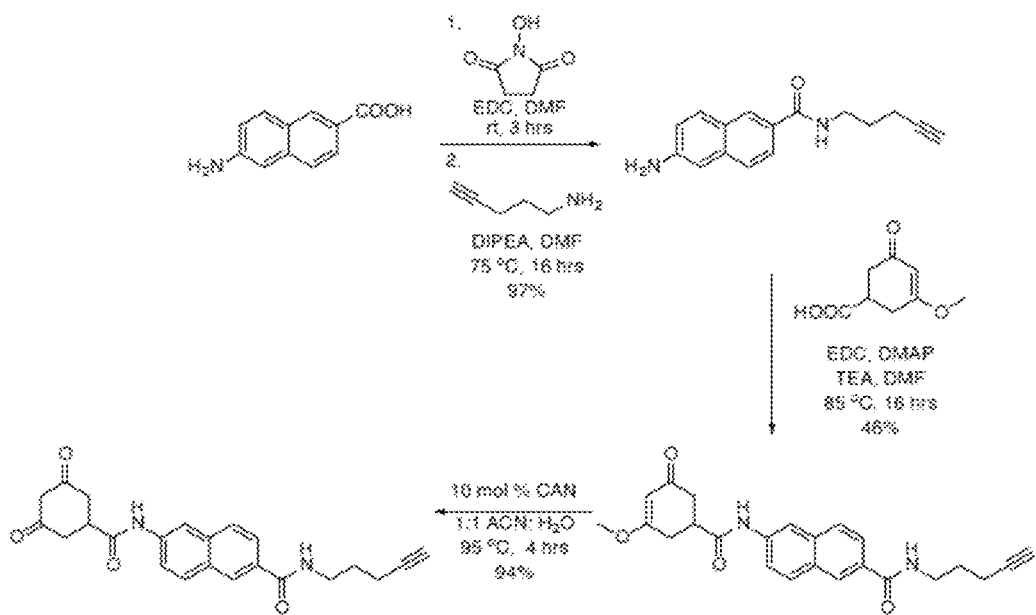
Scheme 2: Synthesis of DYn-Naph
FIG. 6A

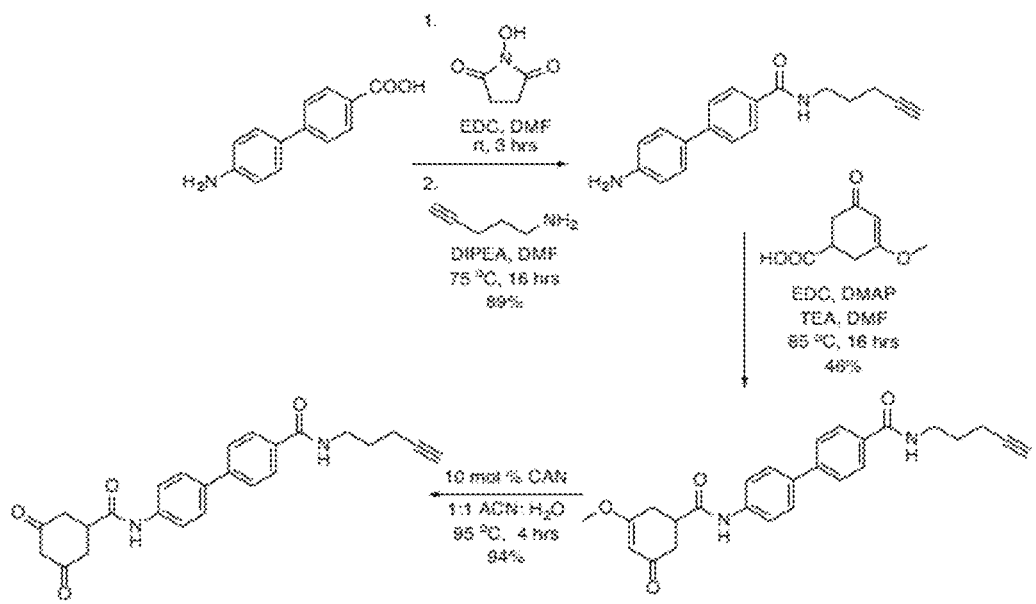
Scheme 3: Synthesis of DYn-BP
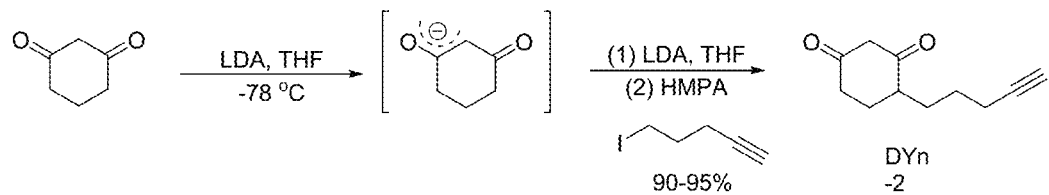
Scheme 4: Synthesis of DYn-2
FIG. 6B A
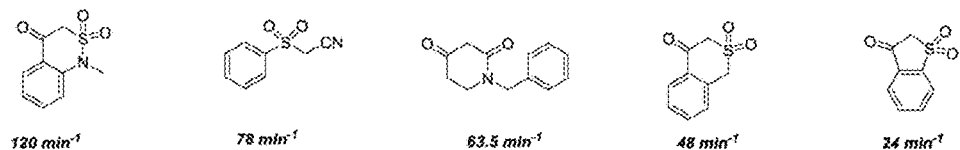
B
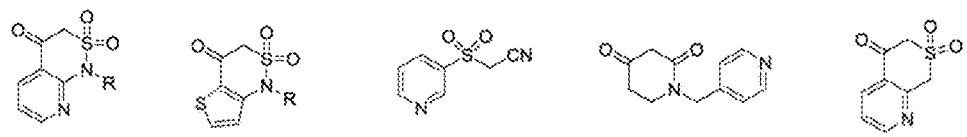
FIG. 10
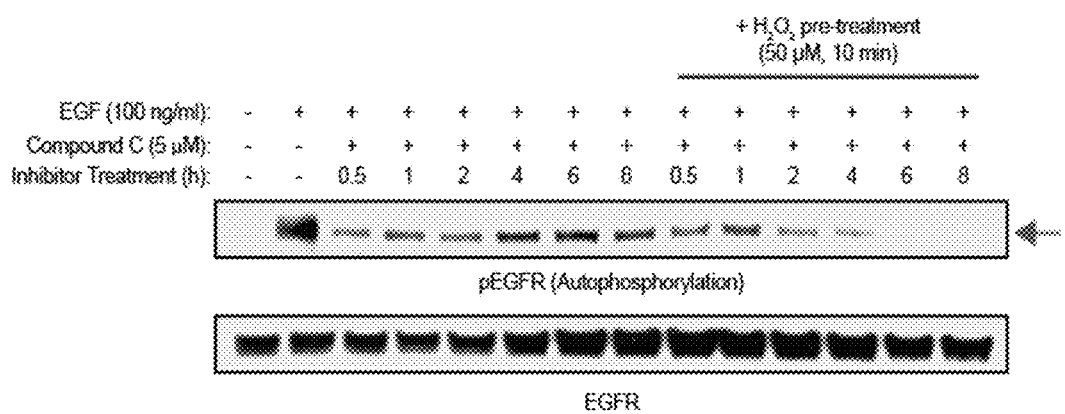
FIG. 11

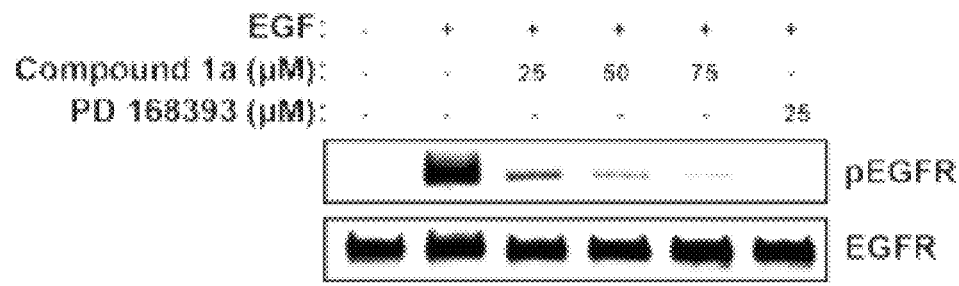
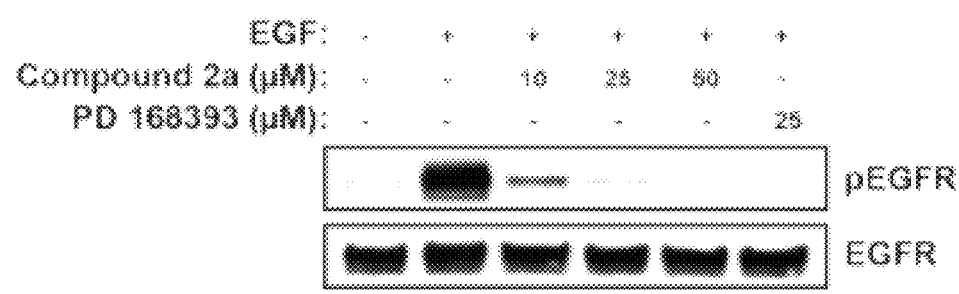
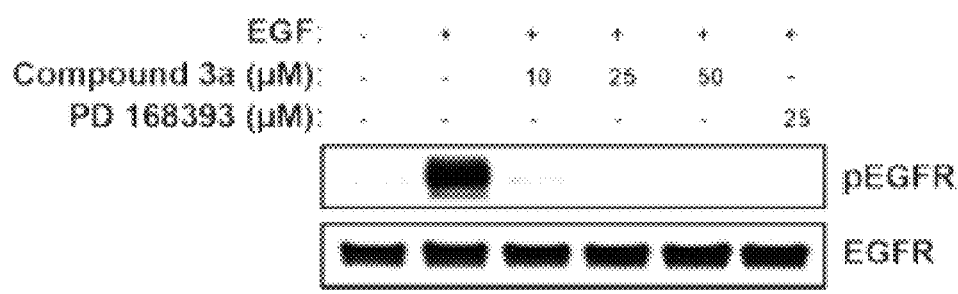
FIG. 15

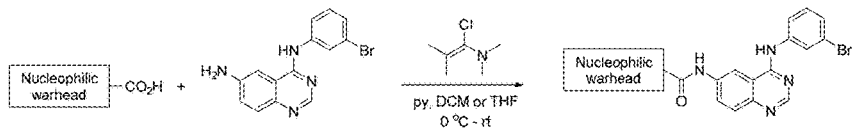
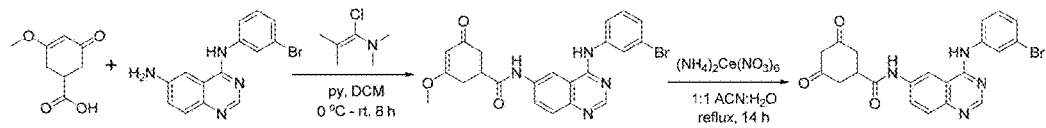
Scheme 2: Synthesis of a redox-based EGFR inhibitor
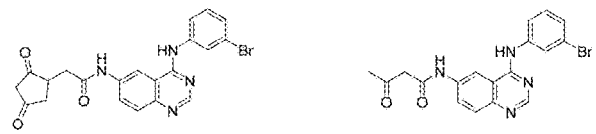
Section 3: Structures of redox-based EGFR inhibitors with different nucleophilic warheads
FIG. 16
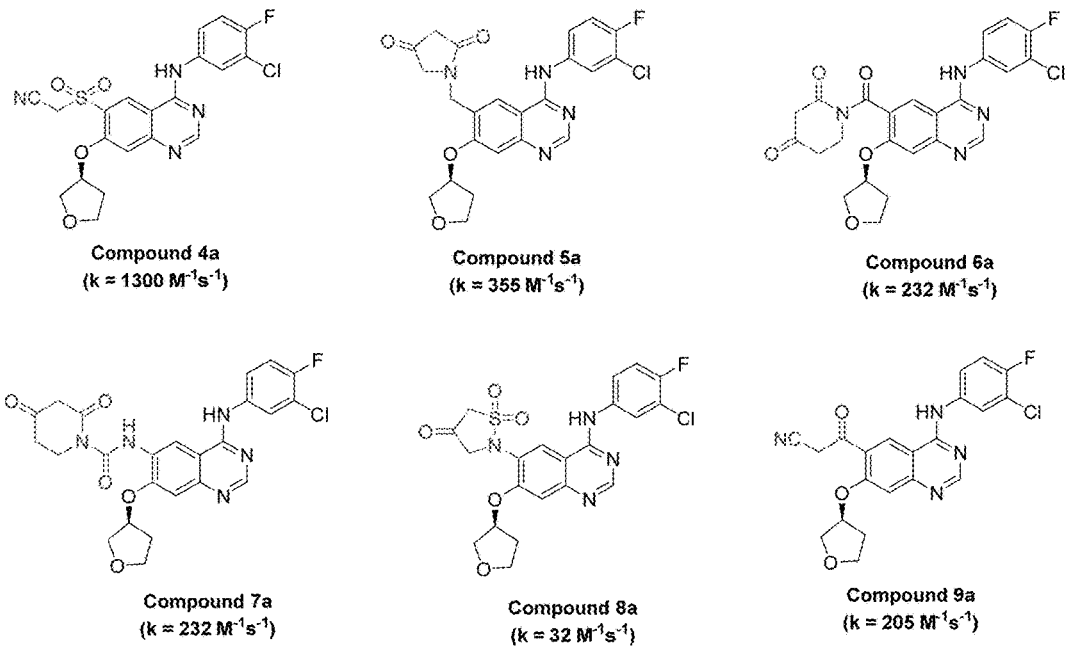
FIG. 17

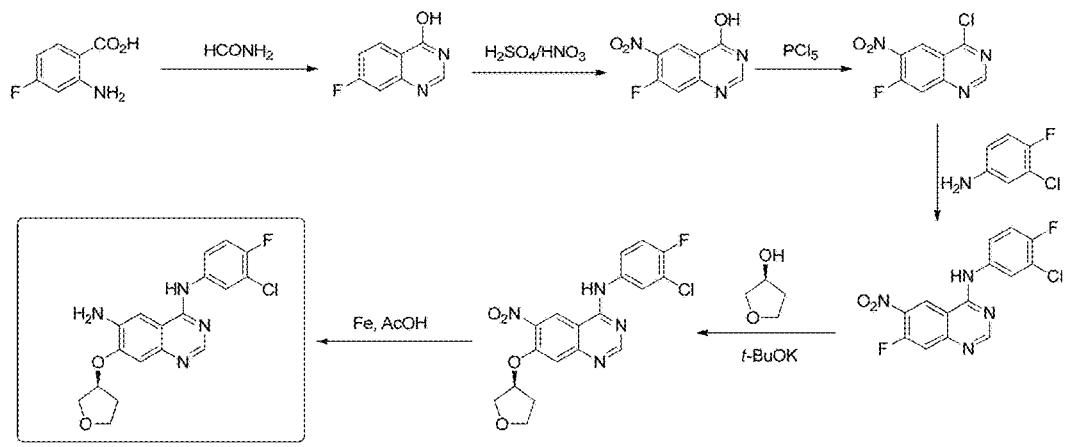
Scheme 1. Synthesis of the core for amide linked warhead attachment
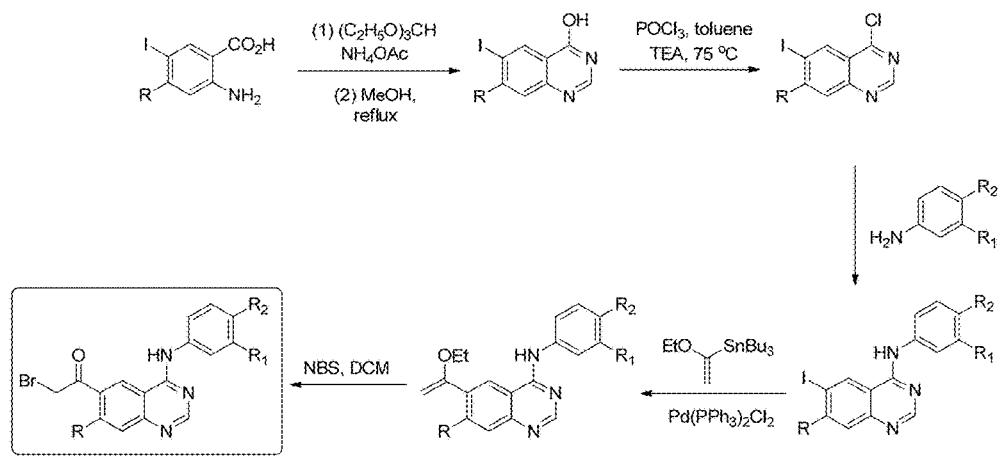
Scheme 2. Synthesis of the core for direct warhead attachment
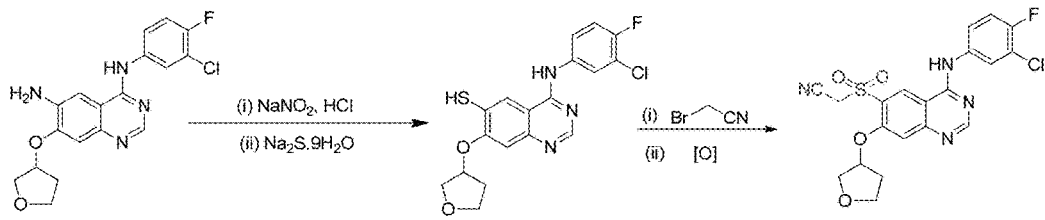
Scheme 3. Synthesis of 4a
FIG. 18A

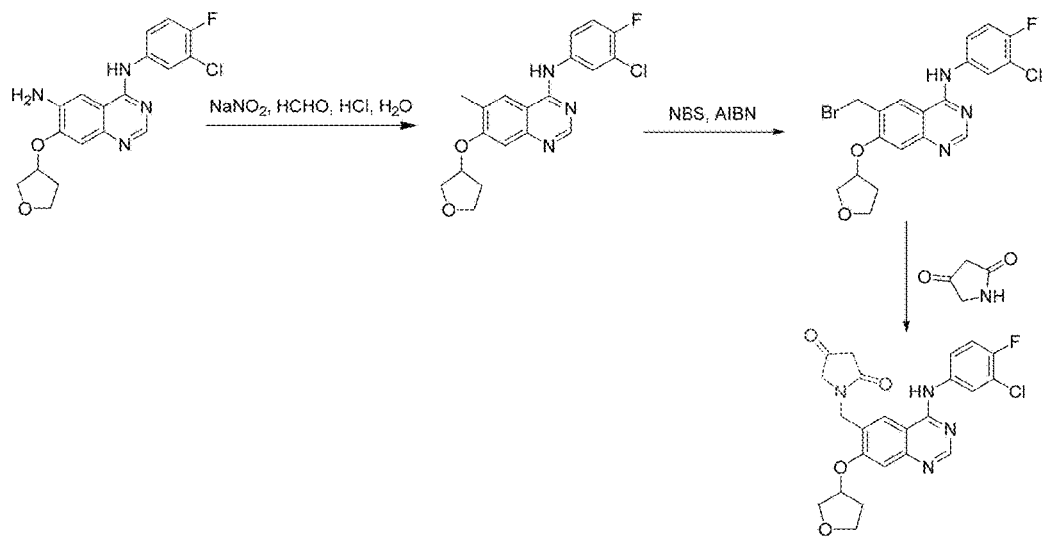
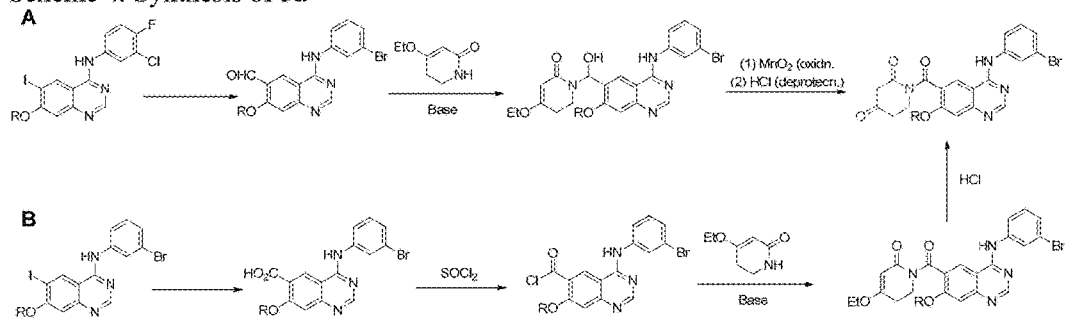
Scheme 4. Synthesis of 5a
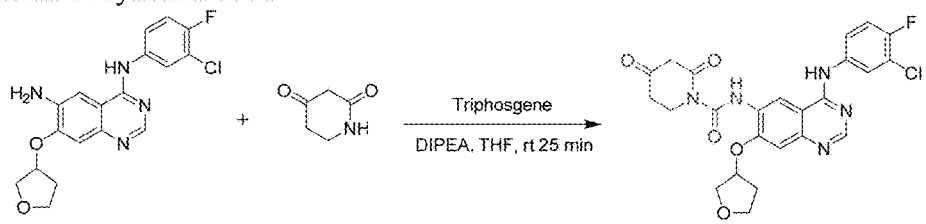
Scheme 5. Synthesis of 6a
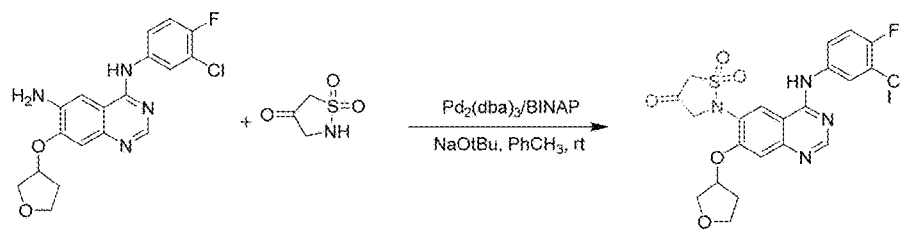
Scheme 6. Synthesis of 7a
Scheme 7. Synthesis of 8a
FIG. 18B Scheme 8. Synthesis of 9a

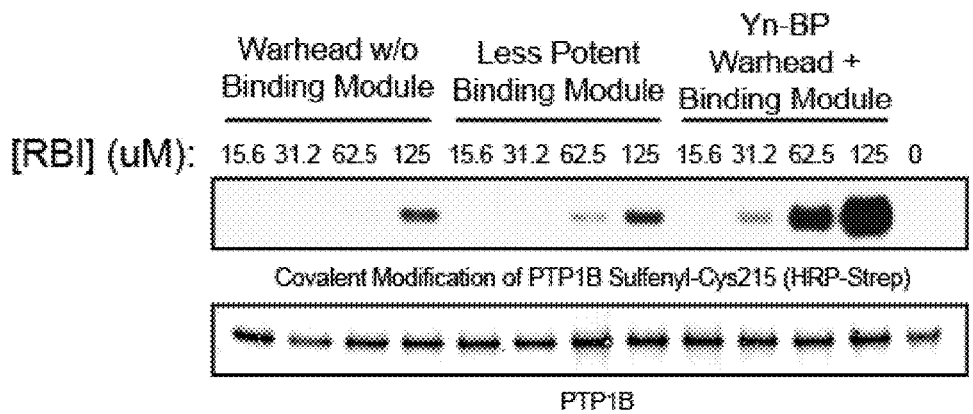
FIG. 25
Scheme 1:
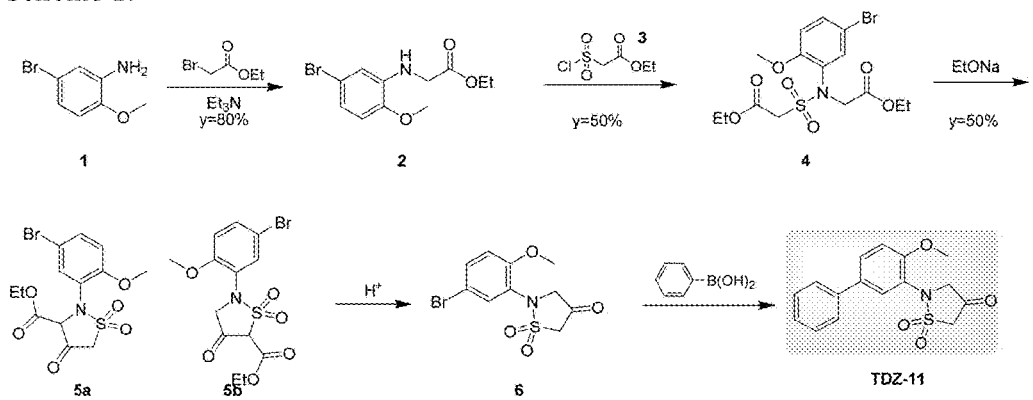
Scheme 2:
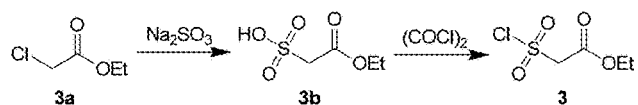
FIG. 26

Scheme 1:
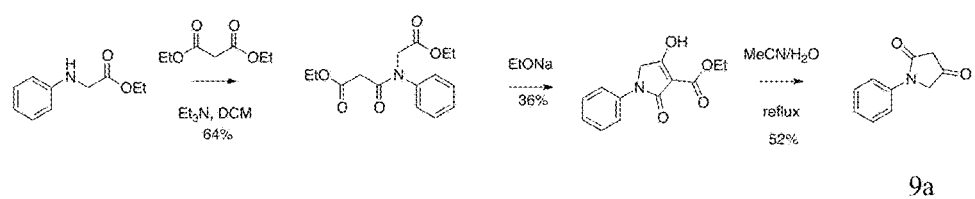
Scheme 2:
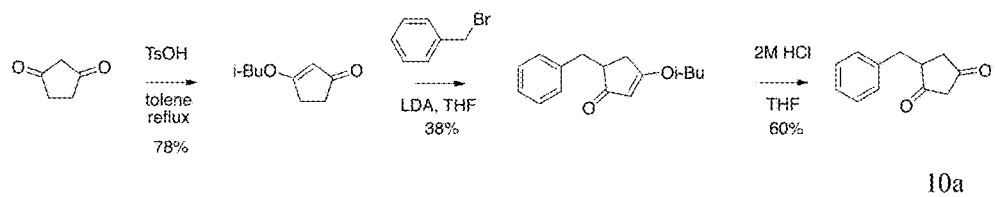
Scheme 3:
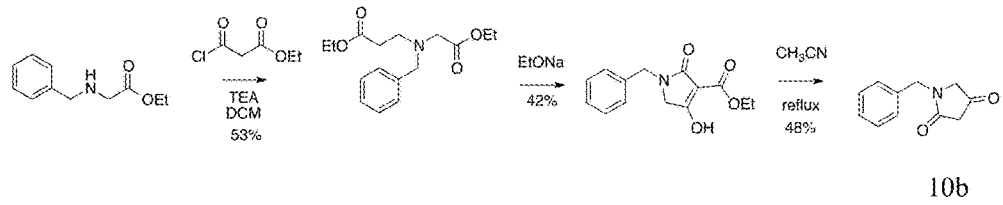
FIG. 27

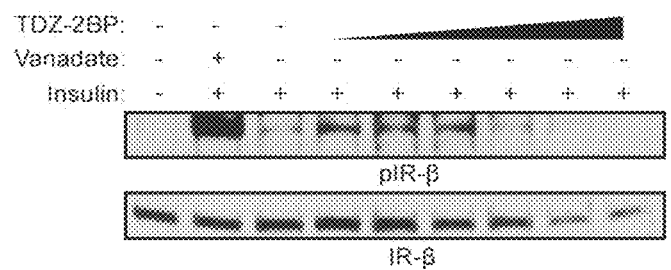
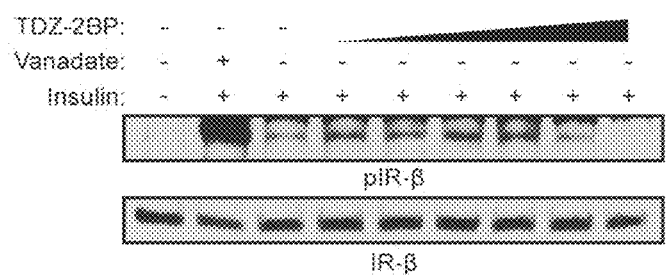
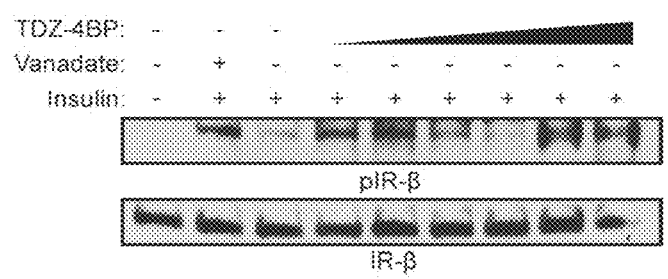
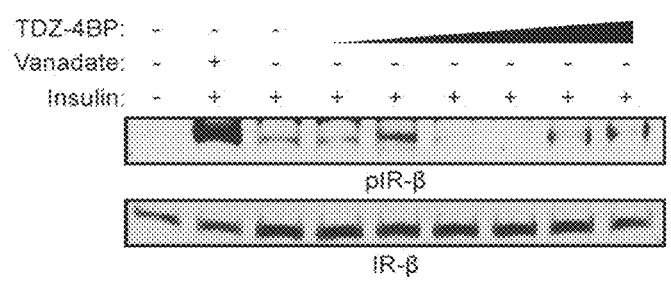
FIG. 28

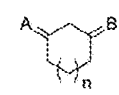

n = 0,1,2
A = O, S
B = O, S

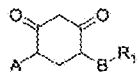

A = H, alkyl, aryl, O, S, NH, F, Cl
B = H, alkyl, aryl, O, S, NH, F, Cl
$R_1$ = H, alkyl, aryl, $CO_2R$, CONHR
(R = H, alkyl, aryl)

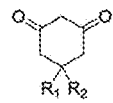

$R_1$ = OR, SR, NH-R, H, alkyl, aryl, $CO_2R$, CONHR
$R_2$ = OR, SR, NH-R, H, alkyl, aryl, $CO_2R$, CONHR
(R = H, alkyl, aryl)

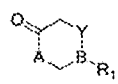

A = C, N, O, S
B = C, N, O, S
Y = CO, SO, $SO_2$
$R_1$ = H, alkyl, aryl, $CO_2R$, CONHR
(R = H, alkyl, aryl)

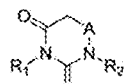

A = CO, SO, $SO_2$
B = O, S, NH
$R_1$ = H, alkyl, aryl, $CO_2R$, CONHR
$R_2$ = H, alkyl, aryl, $CO_2R$, CONHR
(R = H, alkyl, aryl)

A = CO, SO, $SO_2$
B = N, O, S, SO, $SO_2$
$R_1$ = H, alkyl, aryl, $CO_2R$, CONHR
(R = H, alkyl, aryl)

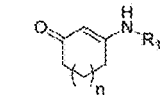

n = 0, 1, 2
R1 = H, alkyl, aryl, $CO_2R$, CONHR
(R = H, alkyl, aryl)

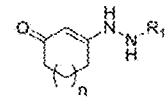

n = 0, 1, 2
$R_1$ = H, alkyl, aryl, $CO_2R$, CONHR
(R = H, alkyl, aryl)

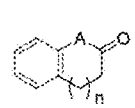

n = 0, 1, 2
A = $CH_2$, O, N, S

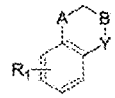

A = CO, SO, $SO_2$
B = CO, SO, $SO_2$
Y = $CH_2$, O, S, N-R (R = alkyl, aryl)
$R_1$ = EDG, EWG

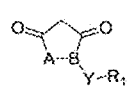

A = $CH_2$, O, S, N
B = $CH_2$, O, S, N
Y = $CH_2$, O, S, N
$R_1$ = H, alkyl, aryl, $CO_2R$, CONHR
(R = H, alkyl, aryl)

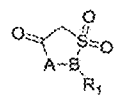

A = $CH_2$, N, O, S
B = $CH_2$, N
$R_1$ = H, alkyl, aryl, $CO_2R$, CONHR
(R = H, alkyl, aryl)

A = CO, SO, $SO_2$
$R_1$ = EWG, EDG

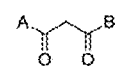

A = H, alkyl, aryl, S, O, N, NNHR, $CF_3$
B = H, alkyl, aryl, S, O, N, NNHR, $CF_3$

R = H, alkyl, aryl
A = H, alkyl, aryl, CN, $NO_2$, $CF_3$, F, Cl

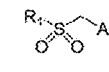

$R_1$ = alkyl, aryl, NHR, O
A = $CO_2R$, CONHR, CONHNHR, CN, $NO_2$, $CF_3$, F
(R = H, alkyl, aryl)

| S.No. | Nucleophiles | $k_{obs}$ (min$^{-1}$) | S.No. | Nucleophiles | $k_{obs}$ (min$^{-1}$) | S.No. | Nucleophiles | $k_{obs}$ (min$^{-1}$) |
|---|---|---|---|---|---|---|---|---|
| 1 | acetylacetone | 3.8 | 16 | butanone | NR | 31 | CF$_3$ sulfonyl methyl | |
| 2 | heptane-2,4-dione | 3.5 | 17 | 1,1,1-trifluoroacetone | NR | 32 | Ph-SO$_2$-CH$_2$-CF$_3$ | |
| 3 | benzoylacetone | 3.2 | 18 | Ph-CO-CH$_2$-CF$_3$ | | 33 | Ph-NH-CO-CH$_2$-SO$_2$-Me | Very slow |
| 4 | dibenzoylmethane | 0.8 | 19 | nitroacetone | Unstable | 34 | Me-CO-CH$_2$-SO$_2$-NH-Ph | 1.4 |
| 5 | methyl acetoacetate | 0.9 | 20 | Ph-CO-CH$_2$-NO$_2$ | 0.5 | 35 | Ph-SO$_2$-CH$_2$-CO-OMe | 0.7 |
| 6 | diethyl malonate | 0.1 | 21 | EtO-CO-CH$_2$-NO$_2$ | 0.6 | 36 | Ph-SO$_2$-CH$_2$-NO$_2$ | 7.8 |
| 7 | N-methyl acetoacetamide | 0.4 | 22 | Et-CO-CH$_2$-CN | unstable | 37 | Me-SO$_2$-CH$_2$-CN | 28.6 |
| 8 | N-phenyl acetoacetamide | 1.5 | 23 | Ph-CO-CH$_2$-CN | 12.3 | 38 | Ph-SO$_2$-CH$_2$-CN | 78 |
| 9 | N,N-diethyl acetoacetamide | 0.05 | 24 | EtO-CO-CH$_2$-CN | 0.7 | 39 | | |
| 10 | morpholino acetoacetamide | 0.06 | 25 | Me-NH-CO-CH$_2$-CN | to be repeated | 40 | | |
| 11 | EtO-CO-CH$_2$-CO-NH-NH$_2$ | NR | 26 | Ph-NH-CO-CH$_2$-CN | to be repeated | 41 | | |
| 12 | H$_2$N-NH-CO-CH$_2$-CO-NH-NH$_2$ | NR | 27 | NC-CH$_2$-CN | 20 to be repeated | 42 | | |
| 13 | Me-CO-CH$_2$-CO-CF$_3$ | NR | 28 | Me-CO-CH$_2$-SO$_2$-Me | 2.7 | 43 | | |
| 14 | F$_3$C-CO-CH$_2$-CO-CF$_3$ | NR | 29 | Me-CO-CH$_2$-SO$_2$-Ph | 8.7 | 44 | | |
| 15 | Ph-CO-CH$_2$-CO-CF$_3$ | NR | 30 | Ph-CO-CH$_2$-SO$_2$-Me | 6.4 | 45 | | |

■ Completed    ▨ Rate studies are pending    ▦ To be synthesized

FIG. 31

TARGETED COVALENT PROBES AND INHIBITORS OF PROTEINS CONTAINING REDOX-SENSITIVE CYSTEINES

CROSS-REFERENCE OF RELATED APPLICATIONS

This is a United States national stage entry of international PCT Application PCT/US2013/073765, filed Dec. 8, 2013, which claims the benefit of priority from U.S. Provisional Patent Application No. 61/735,058, filed Dec. 9, 2012, entitled, "Targeted Covalent Probes And Inhibitors Of Proteins Containing Redox-Sensitive Cysteines," both of which are incorporated herein by reference in their entireties.

NAMES OF PARTIES TO A JOINT RESEARCH AGREEMENT

The claimed invention was made by, on behalf of, and/or in connection with Targanox, Inc. to a joint research agreement within the meaning of 35 U.S.C. § 103(c). The claimed invention was made as a result of activities undertaken within the scope of the agreement.

FIELD OF INVENTION

This invention relates generally to compounds that are probes and irreversible inhibitors of proteins containing redox-sensitive cysteines, including kinases and phosphatases.

BACKGROUND

Phosphorylation and dephosphorylation of various amino acid side chains (e.g., serine, threonine, and tyrosine) is a major mechanism for regulating protein function in eukaryotic cells. Protein kinases and phosphatases regulate nearly all aspects of cell physiology and have emerged as therapeutic targets for a variety of human diseases. The persistent challenges in kinase and phosphatase inhibitor drug discovery have been poor selectivity across the family of enzymes and high intracellular substrate concentrations. In recent years, it has been recognized that covalent inhibitors afford a mechanism to overcome these hurdles and exhibit a distinct pharmacology as compared to non-covalent inhibitors (e.g., prolonged pharmacodynamics and potential to overcome resistance mutations).

Conventional irreversible inhibitors of kinases and phosphatases inactivate their target through covalent attachment to a specific cysteine thiol functional group. However, the electrophilic center (e.g., acrylamide, haloacetamide, vinyl sulfonamide) that reacts with the cysteine residue can show nonspecific reactivity toward other cellular thiols, including glutathione that is present at millimolar concentrations inside mammalian cells. The electrophile may also crossreact with other nucleophilic functionalities present in biological systems (amino and imidazole groups of amino acids, various reactive sites in nucleic acid bases, water). As a result, the high concentration of nucleophiles present in a cell can render traditional approaches to irreversible inhibition problematic (e.g., toxicity, potency). In view of the foregoing, an acute need exists to develop new chemical methods for covalent targeting of kinases and phosphatases.

SUMMARY OF THE INVENTION

The deficiencies of the prior art, namely the challenges in kinase and phosphatase inhibitor discovery have been poor specificity and selectivity and high intracellular substrate concentrations, current covalent inhibitors may substantially overcome the difficulties in consideration of the invention disclosed here. More specifically, additional innovation and advantages are realized when configuring the protection systems.

One object of the invention relates to a compound for modifying the activity of a target protein kinase or phosphatase comprising a nucleophilic warhead and a binding element specific for the target protein.

Another object may be directed to a method of modifying the activity of a target protein by exposing a target protein to a compound comprising a nucleophilic warhead and a binding element specific for the target protein.

In yet a further object, the invention relates to a method of treating a disease in a subject comprising: administering to a subject afflicted with a disease a therapeutically effective amount of a compound that modifies the activity of a target protein and reduces or alleviates the symptoms of the disease.

Another object may be directed to a process for synthesizing a compound for modifying the activity of a target protein comprising: converting a carboxylic acid group on a nucleophilic moiety to an acid chloride, and condensing the acid chloride on the nucleophilic moiety with a primary amine on a binding element.

A further object relates to a method of screening for compounds that bind to a protein with at least one redox-sensitive cysteine residue comprising: exposing a compound to a protein under conditions suitable to cause binding between the compound and the target protein and detecting binding between the compound and the protein.

In yet another object, the invention relates to a method of detecting a protein with a redox-sensitive cysteine comprising: exposing a probe compound to a protein, and detecting the presence or absence of binding of the probe compound to the protein.

A further object relates to a method of detecting a therapeutic target protein comprising: exposing a probe compound to a protein; and detecting the presence or absence of binding of the probe compound to the protein.

These and other features, aspects and advantages of the present invention will become better understood with reference to the following drawings, description, and claims.

BRIEF DESCRIPTION OF THE DRAWINGS

FIG. 6A-FIG. 6B depicts examples of methods used to synthesize probe compounds: DYn-0, DYn-Naph, DYn-BP, and DYn-2.

FIG. 10 depicts preferred nucleophilic warheads ranked by reactivity and binding (A) and modified warheads ranked by reactivity, solubility, and binding (B).

FIG. 11 depicts redox and time-dependent covalent inhibition of EGFR autophosphorylation by compound C.

FIG. 15 depicts Western blot results comparing the phosphorylation of EGFR (pEGFR) with treatment of Compounds 1a, 2a, and 3a in increasing concentrations.

FIG. 16 depicts an example of the method used to synthesize the inventive redox-based EGFR inhibitors.

FIG. 17 depicts exemplary redox-based EGFR inhibitors based on the Afatinib core.

FIG. 18A-FIG. 18C depicts a highly convergent synthetic scheme for the synthesis of the EGFR inhibitors of FIG. 18.

FIG. 25 depicts robust dose-dependent covalent modification of oxidized PTP by compound DYn-BP as compared to compounds that lack either the binding group or the nucleophile warhead.

FIG. 26 depicts a method that is predicted to be useful for synthesizing Compound D (referred to as "TDZ-11" in the figure).

FIG. 27 depicts methods for synthesizing novel PTP1B inhibitors of the invention.

FIG. 28 depicts cell-based data obtained using TDZ-2BP and TDZ-4BP probes.

FIG. 29 depicts generic structures for irreversible sulfenic acid nucleophiles.

FIG. 30 depicts exemplary cyclic nucleophiles including their observed pseudo $1^{st}$ order rate constants ($min^{-1}$).

FIG. 31 depicts exemplary linear nucleophiles including their observed pseudo $1^{st}$ order rate constants ($min^{-1}$).

DETAILED DESCRIPTION OF THE INVENTION

Figure 1:
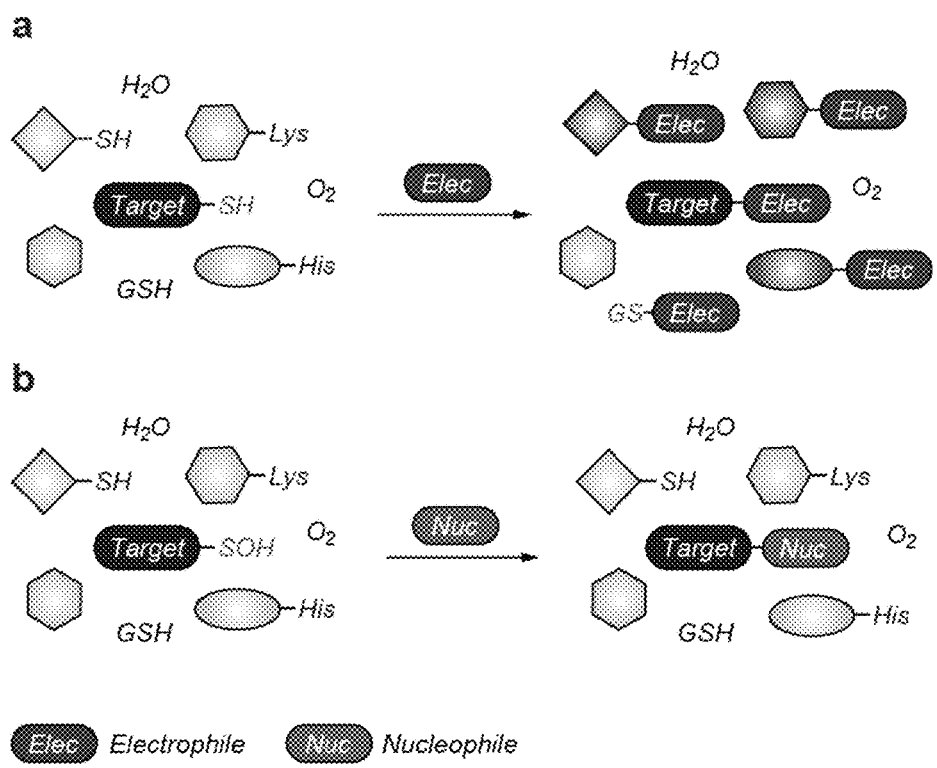
FIG. 1 depicts (a) the conventional approach to irreversible, covalent inhibition of kinases and phosphatases targeting a cysteine thiol among several nucleophiles (the diamond, hexagon, and oval shapes represent off-target hits); and (b) the redox-based inhibitor (RBI) approach targeting the sulfenyl form of cysteine, which is unique among biological functional groups.

A chemical methodology known as redox-based inhibitors (RBIs) may be used to address the problems that may be caused when employing a conventional electrophilic functionality to target a specific cysteine thiol group among a vast sea of biological nucleophiles. According to the RBI method, active site-directed small-molecule inhibitors containing a nucleophilic substituent form a covalent bond with a sulfenic acid- or sulfenamide-modified side chain of a target protein cysteine residue. (See, FIG. 1). Such modifications form in proteins, including kinase and phosphatase enzymes, with reactive cysteine residues during $H_2O_2$-mediated signal transduction in normal cells and constitutively in diseases associated with chronically elevated levels of $H_2O_2$, such as cancer. In the sulfenyl oxidation state, the electron-deficient sulfur atom behaves chemically as a soft electrophile. This reactivity is exquisitely unique among biological functional groups and represents a novel chemical mechanism for covalent targeting of potential therapeutic proteins, including kinases and phosphatases. However, it is understood that the invention is not bound by any specific mechanism of action, so long as the goals of the invention (i.e., identifying target proteins with redox-sensitive cysteines and modifying their activities with the inventive compounds) are achieved. In some cases, the goal of the invention may not be to inhibit the activity of a target protein, but to enhance the activity of the protein. Further, the invention is not limited to kinases and phosphatases and applies to any protein with at least one redox-sensitive cysteine.

Reversible oxidation of cysteine thiols may be an important regulatory mechanism for protein function. In particular, cysteine oxidation may function as a global signaling mechanism in cells. Targeting cysteine residues in their oxidized state may lead to the development of a new class of therapeutics that have increased specificity for disease-relevant proteins, thereby reducing non-specific effects.

The compounds of the invention include two moieties: a binding element or binding module, used interchangeably here, that promotes interactions with a specific target protein and a nucleophilic warhead that binds to a sulfenyl-modified cysteine residue in the target protein. Optionally, the compounds of the invention may also contain a label (e.g., fluorophore, biotin, azide, or alkyne) for visualization and affinity purification of target proteins. In addition, altering the structure of an existing compound that modifies the activity of a target protein to include a nucleophilic "warhead" can create a novel compound of the invention.

The embodiments of the invention relate generally to the modification of the activity of proteins, and include inhibitors that specifically interact with a redox-sensitive cysteine in the active site of a kinase or phosphatase. The invention also includes probes designed to detect proteins with redox-sensitive cysteines.

As used herein, the terms "binding" or "interaction" refers to an association between a chemical entity, compound, or portions thereof, with another chemical entity, compound, or portions thereof. The association can be non-covalent or covalent.

As used herein, the term "redox-sensitive cysteine" refers to a cysteine residue that is susceptible to being oxidized or reduced under physiological or experimental conditions.

Modulating Compounds

In one aspect, this invention relates to certain classes of novel compounds that are useful for modifying the activity of target proteins with at least one redox-sensitive cysteine. Compounds useful for modifying target protein activity comprise a "binding element" and a functional, nucleophilic moiety or "warhead." The nucleophilic warhead can include any carbon, nitrogen, sulfur, or phosphorous-based functional group capable of binding to a target protein with at least one redox-sensitive cysteine residue. In certain embodiments, the nucleophilic warhead is capable of binding to a target protein that is a kinase or phosphatase. In further embodiments, the nucleophilic warhead is capable of forming a covalent bond with a redox-sensitive cysteine residue within the active site of the protein. In further embodiments, the nucleophilic warhead is capable of binding to sulfenic acid- or sulfenamide-modified redox-sensitive cysteine residue.

The binding element or module of the inventive compound can be any functional group or structure suitable for promoting interactions with the target protein. In certain embodiments, the binding element is a functional group or structure suitable for promoting interactions with a target protein kinase of phosphatase. Further embodiments may be directed to binding elements that can be any functional group or structure that promotes interactions with the active site of the target protein. The binding element of another embodiment can be any functional group or structure that promotes modification of the activity of a target protein. Yet further embodiments may relate to binding elements that comprise or contain a substituted aryl or heterocyclic core structure comprised of two or more rings that promote interactions with a specific protein, including, but not limited to, a specific protein kinase or phosphatase. The compounds of the invention that modify the activity of target proteins may also be used as probes, preferably if the compounds contain a label, reporter, or reporter tag, where in preferred embodiments the label is detectable.

Syntheses of Modulating Compounds

A further aspect of the invention comprises a process for synthesizing compounds that modify or modulate, either by increasing or decreasing, the activity of target proteins with at least one redox-sensitive cysteine by altering the structure of a compound to include a nucleophilic warhead. In certain embodiments, the compound that is altered to include a nucleophilic warhead may be a compound that is known to modify the activity of a target protein. Other embodiments may be directed to compounds known to modify the activity of a target protein that are known agonists or antagonists of the target protein. In further embodiments, the process synthesizes a compound that can modify the activity of a target protein kinase or phosphatase with at least one redox-sensitive cysteine.

Method for Screening Redox-Sensitive Cysteine Target Protein-Binding Compounds

Another aspect of the invention relates to a method of screening for compounds that bind to a target protein with at least one redox-sensitive cysteine. Generally, the method comprises exposing a compound to a target protein containing at least one redox-sensitive cysteine under conditions suitable to cause binding between the compound and the target protein, and then detecting if there is binding between the compound and the target protein. Any suitable assay known in the art may be used to detect binding between the compound and the protein. For example, binding between the compound and the kinase or phosphatase may be detected using mass spectroscopy, fluorescence assays, chromatography techniques, or combinations of any of the aforementioned methods. The chromatography techniques may include, but are not limited to, high-performance liquid chromatography. Further, binding between the compound and target protein may be detected using a combination of assays, for example, a combination of liquid chromatography and mass spectroscopy. In certain embodiments of the screening method, a suitable fragment of the target protein containing a redox-sensitive cysteine may be used instead of the entire target protein. Further, in some embodiments, the compound may also comprise only a nucleophilic warhead. Certain embodiments may be directed to target proteins that may be either a kinase or phosphatase or any therapeutically relevant protein with at least one redox-sensitive cysteine.

Compound and Target Protein Binding Via Covalent Adduct

In yet other embodiments, the binding between the compound and the target protein may be in the form of a covalent adduct and the covalent adduct may be detected. The compound may form a covalent adduct with the active site of the target protein in certain embodiments where the covalent adduct formed by the compound and the target protein may be either reversible or irreversible. In additional embodiments, the redox-sensitive cysteine residue may be a sulfenic acid- or sulfenamide-modified cysteine residue. Sulfenylation may be a general regulatory mechanism among kinases. The target cysteine may be found in exemplary kinases having similar amino acid sequences (TABLE 1). Oxidation of the conserved cysteine within the ATP binding site of EGFR (Cys797) may be a significant target for irreversible inhibitors and accordingly, may be the site of oxidation.

TABLE 1

| KINASE | AMINO ACID SEQUENCE WITH TARGET CYSTEINE |
|--------|------------------------------------------|
| EGFR   | T Q L M P F G C L L D |
| HER2   | T Q L M P Y G C L L D |
| HER4   | T Q L M P H G C L L E |
| BLK    | T E Y M A R G C L L D |
| BMX    | T E Y I S N G C L L N |
| BTK    | T E Y M A N G C L L N |
| ITK    | F E F M E H G C L S D |

TABLE 1-continued

| KINASE | AMINO ACID SEQUENCE WITH TARGET CYSTEINE |
|---|---|
| JAK3 | M E Y L P S G <u>C</u> L R D |
| TEC | T E F M E R G <u>C</u> L L N |
| TXK | T E F M E N G <u>C</u> L L N |

Preferred embodiments may be directed to compounds that include a binding element having a substituted aryl or heterocyclic core structure that promotes binding with the target protein kinase or phosphatase, and a nucleophilic warhead that is capable of forming a covalent adduct with a sulfenic acid or sulfenamide-modified cysteine residue in the active site of the protein.

Compound and Target Protein Binding—Enzymatic Activity Confirmation

Figure 2:
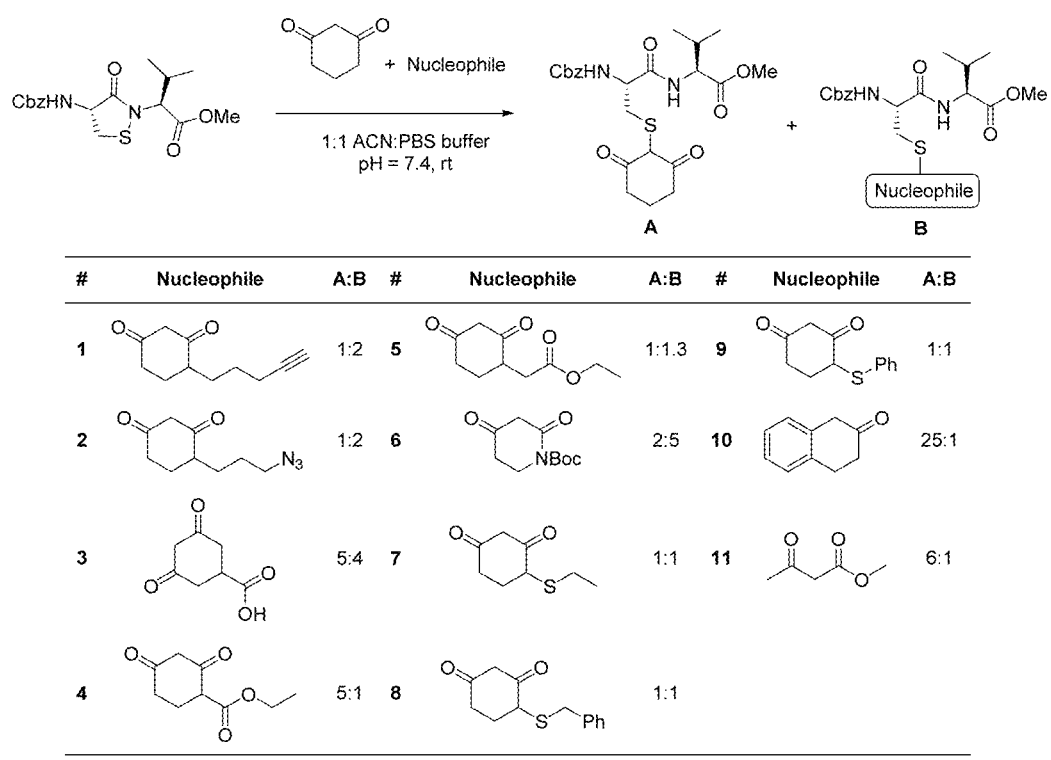
FIG. 2 depicts an example of a method comparing the nucleophilic reactivity of various compounds to the nucleophilic reactivity of 1,3-cyclohexanedione.
Figure 3A:
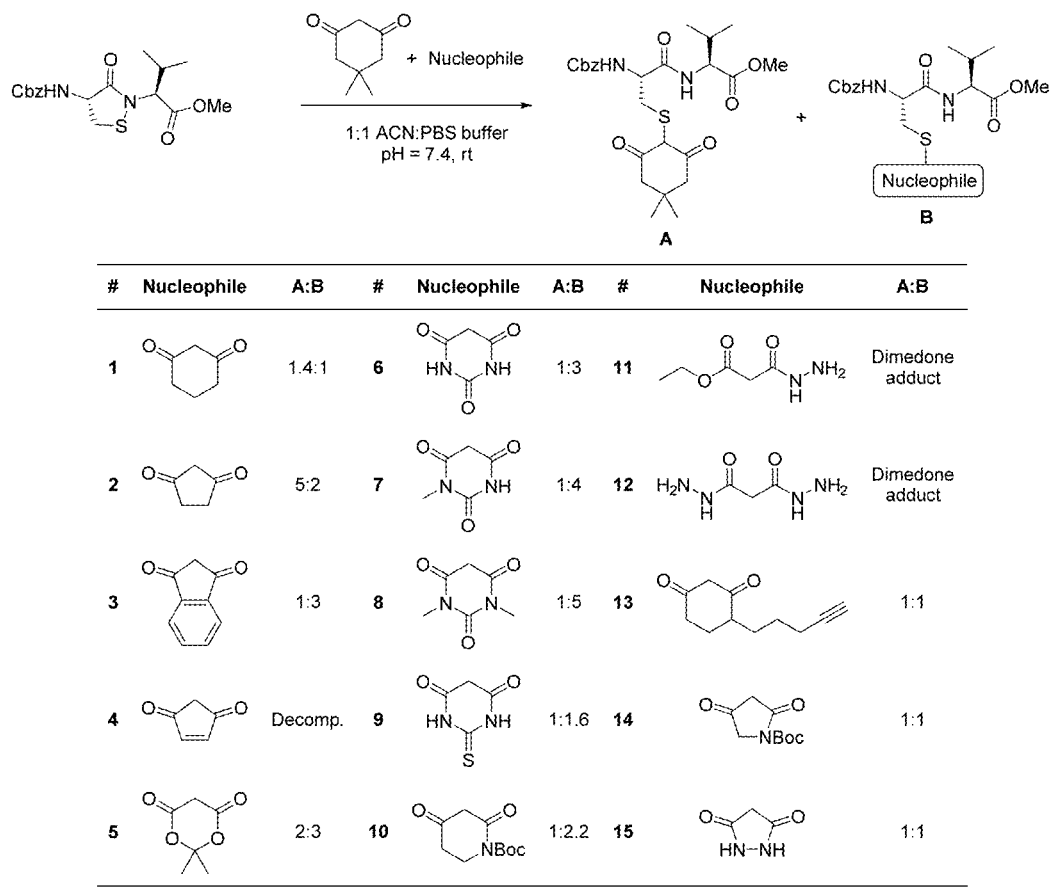
FIG. 3A depicts an example of a method comparing the nucleophilic reactivity of various compounds to the nucleophilic reactivity of dimedone.
Figure 3B:
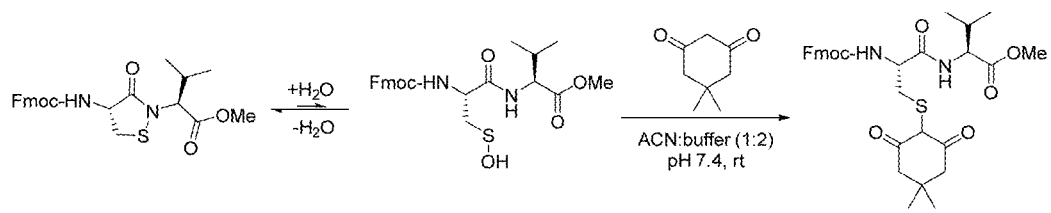
FIG. 3B depicts another model system to measure reaction rates of compounds compared to dimedone.

If it is determined that a compound binds to a target protein, then the compound likely modifies the activity of the target protein. A compound's ability to modify the activity of a target protein may be confirmed using standard assays for measuring enzymatic activity of the target protein in the presence of the compound. Generally, the activity of the target protein is measured in the presence of a protein substrate and the compound, and then compared to the activity of the target protein in the presence of the protein substrate, but in the absence of the compound. In certain embodiments, the target protein may be a kinase or phosphatase and the substrate may be a substrate suitable for a kinase or phosphatase. For example, in one embodiment of the method, the ADP-Glo™ Assay by Promega may be used to confirm that a compound modifies the activity of a target protein kinase. In another embodiment of the method, the Pro-Fluor® Tyrosine Phosphatase Assay by Promega may be used to confirm that a compound modifies the activity of a target protein phosphatase. In certain embodiments, the activity of the target protein is measured in different oxidizing or reducing environments. For example, in certain embodiments, the activity of the target protein in the presence of a protein substrate, and either the presence or absence of a compound, may be measured in experimental environments having different concentrations of $H_2O_2$, or any other oxidizing agent. The higher the reactivity, the higher the amount of compound bound to the target protein Comparison of Multiple Compounds Binding a Target Protein Another aspect of the invention relates to a method of comparing the ability of two different compounds to react with a target protein or target protein fragment containing a sulfenylated redox-sensitive cysteine. Generally, the method includes exposing a target protein fragment containing a sulfenylated redox-sensitive cysteine to an amount of one compound and an equal amount of another compound under conditions suitable to cause binding between the target protein and the compounds, detecting the amount of binding between the target protein and the compounds, and then comparing the amount of binding between the target protein and one compound to the amount of binding between the target protein and the other compound. The amount of binding between the compounds and the target protein may be determined by calculating a ratio or percentage of target protein bound to the compound out of the total protein pool that was contacted with the compounds. A compound that displays a higher amount of binding to the target protein compared to another compound is considered to be more reactive than the other compound. In some embodiments, a fragment of the target protein may be used instead of the entire target protein. In further embodiments, the amount of binding between the target protein and the two different compounds is detected using chromatography techniques. The chromatography techniques may include, but are not limited to, high-performance liquid chromatography. In further embodiments, the compound comprises only a nucleophilic warhead. Examples of the method are described in FIGS. 2-3, which compare the reactivity of different compounds with a target protein fragment, specifically a protected dipeptide, containing a sulfenylated redox-sensitive cysteine.

Determining Compound's Reactivity with Oxidized Forms of Target Protein

A further aspect of the invention relates to a method for determining a compound's reactivity with oxidized forms of a target protein with at least one redox-sensitive cysteine. Generally, the method comprises making a first sample by exposing a compound to an oxidized form of a target protein under conditions suitable to cause binding between the compound and the oxidized protein in the first sample; measuring the quantity of binding between the compound and target protein in the first sample; making a control sample by exposing the compound to a reduced form of a target protein under conditions suitable to cause binding between the reduced form of the target protein in the control sample; measuring the quantity of binding between the compound and target protein in the control sample; and determining the potency of the compound by comparing the quantity of binding in the first sample to the quantity of binding in the control sample. In some embodiments, the target protein is a kinase or phosphatase. In further embodiments of the method, a fragment of the target protein may be used instead of the entire target protein. Certain embodiments may be directed to the binding between the compound and the target protein in the samples which may form a covalent adduct between the compound and the target protein, and the quantity of covalent adducts may be measured and compared in the samples. Any suitable assay for measuring the quantity of binding, or quantity of covalent adducts, in the two samples may be used with this method. For example, binding between the compound and the target protein may be detected using mass spectroscopy, fluorescence assays, and/or chromatography techniques. The chromatography techniques may include, but are not limited to, high-performance liquid chromatography. Further, binding between the compound and target protein may be detected using a combination of assays, for example, a combination of liquid chromatography and mass spectroscopy. The method may also be carried out in live and intact cells to determine a compound's reactivity with oxidized forms of the target protein in live cells. In certain embodiments, the potency of the compound is determined based on the degree of reduction of the quantity of adducts formed in the first sample compared with the quantity of adducts formed in the control sample, in a proportion to the quantity of compound used. In further embodiments, the potency of the compound is determined by calculating a ratio of the number of adducts formed in the first sample compared to the number of adducts formed in the control sample. A ratio of one compound can be compared directly to a ratio for another compound.

Reactivity of dimedone with oxidized PTP1B was compared under varying conditions by mass spectroscopy analysis. When analysis was performed for the following samples: PTP alone; PTP+10 eq $H_2O_2$ (10 mins)+10 mM dimedone (1 hour); PTP1B+1.25 eq H$_2$O$_2$ (50 mins)+50 mM dimedone (1 hour); PTP1B+1.25 eq H$_2$O$_2$ (50 mins), no adduct was observed. The presence of an adduct or covalent adduct suggests binding between the compound and the target protein, and in the case of the reactions identified in TABLE 2, the target protein is PTP1B. The degree of potency of the compound may be based on the degree of reduction of the quantity of adducts formed in a first sample compared with the quantity of adducts formed in the control sample in proportion to the quantity of compound used.

TABLE 2

| REACTIVITY WITH OXIDIZED PTP1B | COMPOUND |
|---|---|
| No adduct | 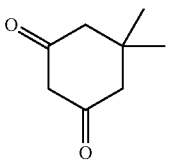<br>Dimedone |
| No adduct | 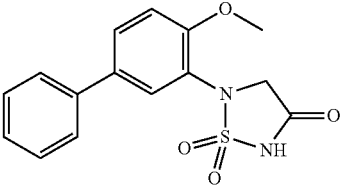<br>TDZ |
| No adduct | 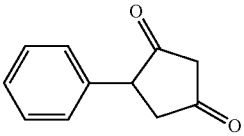<br>TDZ-1 |
| Adduct | 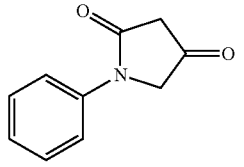<br>TDZ-2 |
| Adduct | 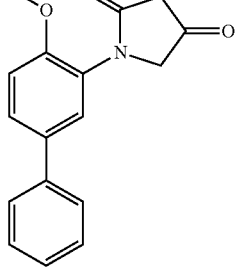<br>TDZ-2BPOMe |
| Adduct | 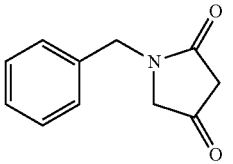<br>TDZ-2BPOH |
| No adduct | 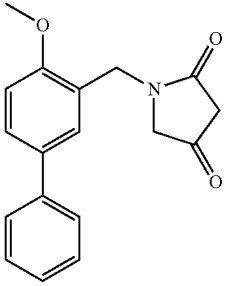<br>TDZ-3 |
| Adduct | 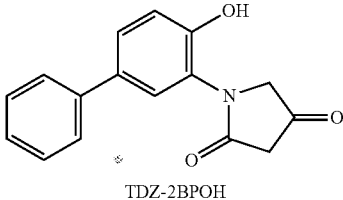 [SMILES: O=C1CC(=O)N(c2cc(-c3ccccc3)ccc2O)C1]<br>TDZ-4 |
| Adduct | 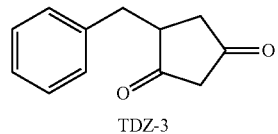 [SMILES: O=C1CC(=O)C(Cc2ccccc2)C1]<br>TDZ-4BPOMe |
| Adduct | 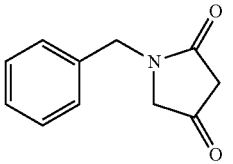<br>TDZ-4BPOH |
| No adduct | 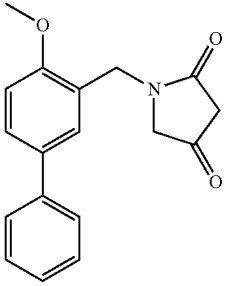<br>TDZ-5 |

TABLE 2-continued
| REACTIVITY WITH OXIDIZED PTP1B | COMPOUND |
|---|---|
| No adduct | 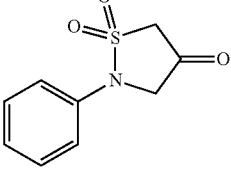 TDZ-6 |
| No adduct | 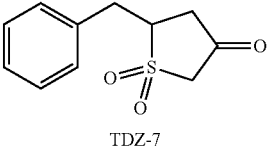 [SMILES: O=C1CC(Cc2ccccc2)S(=O)(=O)C1] TDZ-7 |
| No adduct | 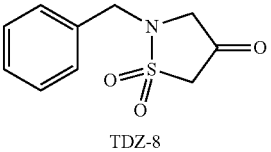 [SMILES: O=C1CN(Cc2ccccc2)S(=O)(=O)C1] TDZ-8 |
| No adduct | 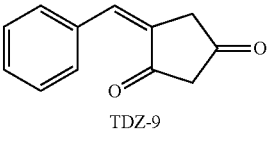 [SMILES: O=C1CC(=O)/C(=C\c2ccccc2)C1] TDZ-9 |
| No adduct | 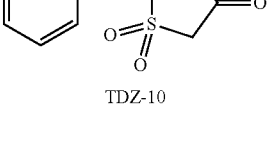 TDZ-10 |
| No adduct | 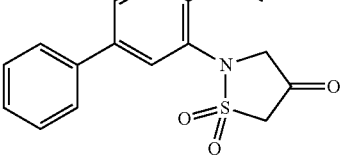 TDZ-11 |
| Adduct | 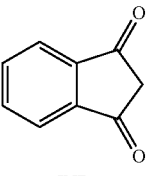 IND |
| Adduct | 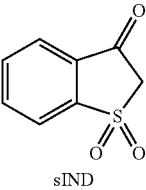 sIND |
| Adduct | 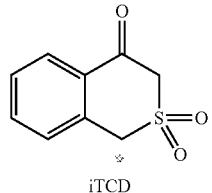 [SMILES: O=C1CS(=O)(=O)Cc2ccccc21] iTCD |
| Adduct | 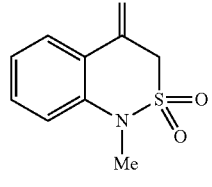 mBTD |
| No Adduct | 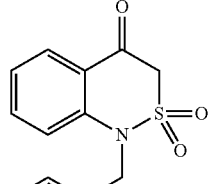 bBTD |
| No Adduct | 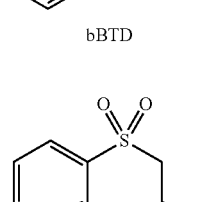 sQHD |
| No Adduct | 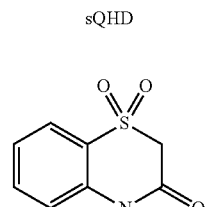 msQHD |
| No Adduct | 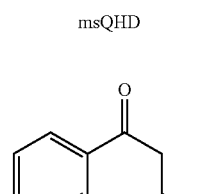 QHD |

TABLE 2-continued

| REACTIVITY WITH OXIDIZED PTP1B | COMPOUND |
|---|---|
| No Adduct | 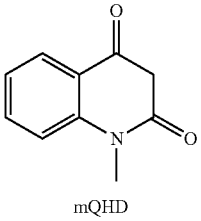<br>mQHD |
| No Adduct | 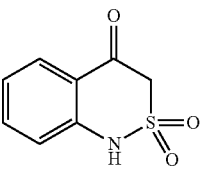<br>BTD |
| Adduct | 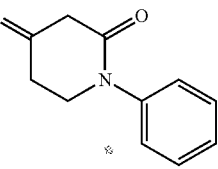<br>pPRD |
| Adduct | 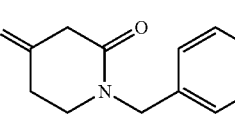<br>bPRD |

Screening for Redox-Sensitive Cysteine Target Proteins with Probes

The invention also provides a method of detecting proteins containing at least one redox-sensitive cysteine by using probe compounds designed to interact with a redox-sensitive cysteine in a protein. Generally, the method includes exposing a probe compound to a target protein, and then detecting the presence or absence of binding of the probe compound to the target protein. The presence of binding of the probe compound to the target protein indicating that the target protein contains a redox-sensitive cysteine in its sulfenic acid or sulfenamide-modified form. In certain embodiments, the target protein is a kinase or phosphatase. In further embodiments, the redox-sensitive cysteine is in a sulfenic acid- or sulfenamide-modified form. The method can be carried out in vitro or in vivo in accordance with known techniques or variations of known techniques. The method may also be used to detect proteins containing at least one redox-sensitive cysteine in intact cells. Further, the method can be used to determine whether a protein with a redox-sensitive cysteine is present or absent in a sample. The method can further be used to monitor redox signaling pathways and networks in cells and in assays that do not involve cells. The methods can also be used to screen cells or tissue for exposure to environmental contaminants or oxidative stress.

Figure 4:
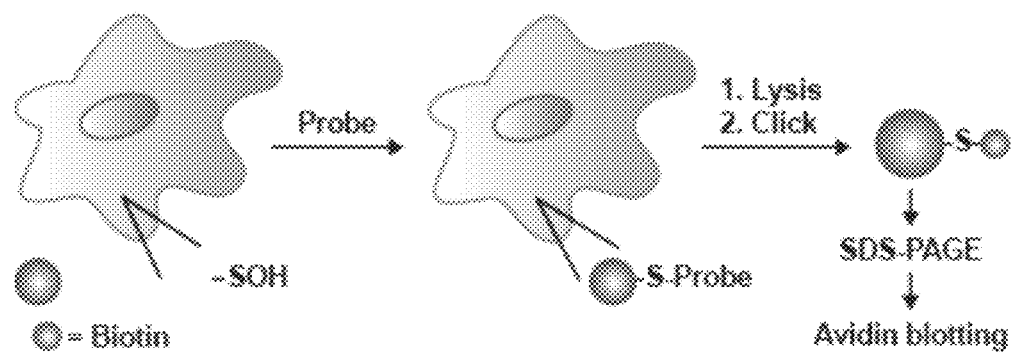
FIG. 4 depicts an example of the method for detecting protein kinases and phosphatases containing at least one redox-sensitive cysteine.

The methods of detecting proteins containing at least one redox-sensitive cysteine can be implemented with any suitable assay. For example, the amount and location of proteins containing at least one redox-sensitive cysteine in its sulfenic acid or sulfenamide-modified form may be visualized in intact tissues or cells, permeabilized cells, or fixed tissues or cells. In some embodiments, the presence or absence of binding of probe compounds to proteins containing at least one redox-sensitive cysteine is detected, at least in part, using "click chemistry." Examples of "click chemistry" are described in Hang, H. C., et al. Mechanism-Based Probe for the Analysis of Cathepsin Cysteine Proteases in Living Cells. ACS Chem. Biol. 1, 713-723 (2006). Further, proteins containing at least one redox-sensitive cysteine may be detected, isolated, and/or identified by applying a probe compound to intact cells or tissues, cell lysates, or fractionated cell extracts, and then isolating, detecting, and/or identifying protein kinases or phosphatases bound to the probe compound using immunoaffinity procedures and/or two-dimensional gel procedures for separation followed by mass spectrometry (for example, nuclear magnetic resonance spectroscopy or "NMR"), chromatographic techniques, or Western blot analysis. An example of the inventive method of detecting proteins containing at least one redox-sensitive cysteine is depicted in FIG. 4, where a probe compound was used to label proteins in A431 cells using "click chemistry" and streptavidin-HRP Western blotting.

A further example of the inventive method for identifying target proteins with at least one redox-sensitive cysteine uses the probe compound DYn-2. The probe compound DYn-2 is a particularly chemoselective probe for detecting proteins containing at least one sulfenic acid or sulfenamide-modified redox-sensitive cysteine directly in cells. Further, DYn-2 has demonstrated improved sensitivity compared to other probes. For example, studies have demonstrated that DYn-2 displays a greater total signal and signal ratio compared to DAz-2 when both probes were used to label A431 and HeLa cells under identical conditions. See, for example, FIG. 2(e) in Paulsen et al., "Peroxide-dependent sulfenylation of the EGFR catalytic site enhances kinase activity," *Nat. Chem. Biol.*, 8, 57-64 (2011) (including Supplemental Information). DYn-2 is capable of monitoring global changes in protein sulfenylation and has demonstrated the ability to detect differences in sulfenylation rates within cells due to differences in protein target localization. The structure of the DYn-2 compound is provided in FIG. 5.

Some of the target proteins that have been identified using the inventive methods include, kinases and phosphatases, but are not limited to, PTEN, PTP1B, SHP2, and EGFR.

Probe Compounds for Identifying Redox-Sensitive Cysteine Proteins

A further aspect of the invention comprises the probe compounds that can be used with the inventive methods for identifying proteins with at least one redox-sensitive cysteine. These include probe compounds that are designed to interact with the sulfenic acid or sulfenamide-modified form of redox-sensitive cysteines. In certain preferred embodiments, the probe compounds comprise a nucleophilic warhead that binds with a redox-sensitive cysteine and a label that may be detected using methods known in the art. The label can be any suitable label or detectable or otherwise functional group, including, but not limited to, biotin, avidin, fluorophores, antigens (including, e.g., proteins and peptides), antibodies, porphyrins, and radioactive or stable isotopes. The label may further comprise azides or alkynes suitable for use in "click chemistry." The probe compounds may, optionally, include a binding element that promotes interactions with a target protein. In certain embodiments, the binding element promotes interactions with the active site of a target protein. In addition, the probe compounds may also, in some cases, modify the activity of a target protein. Examples of these probe compounds include, but are not limited to, those depicted in FIG. 5.

Syntheses of Probe Compounds

The invention also provides methods of synthesizing probe compounds by altering the structure of a compound to include a nucleophilic warhead. Methods of synthesizing the compounds DAz-1 and DAz-2 are described in Reddie et al., "A chemical approach for detecting sulfenic acid-modified proteins in living cells," Mol. Biosyst., 4, 521-531 (2008) and Leonard et al., "Mining the Thiol Proteome for Sulfenic Acid Modifications Reveals New Targets for Oxidation in Cells," ACS Chem. Biol., 4, 783-799 (2009). FIG. 6A and FIG. 6B provide examples of methods of synthesizing probe compounds DYn-0 (Scheme 1), DYn-Naph (Scheme 2), DYn-BP (Scheme 3), and DYn-2 (Scheme 4).

A further aspect of the invention is a method of identifying proteins that are potential therapeutic targets, based on the proteins having at least one redox-sensitive cysteine. Generally, the method includes exposing a probe compound to a target protein and detecting the presence or absence of binding of the probe compounds to the target protein, the presence of binding of the probe compound to the target protein indicating that the target protein contains at least one redox-sensitive cysteine and is a potential therapeutic target. The method can be carried out in vitro or in vivo in accordance with known techniques or variations of known techniques. In some embodiments of the method, the potential therapeutic target protein is a kinase or phosphatase. The methods of detecting potential therapeutic target proteins containing at least one redox-sensitive cysteine can be implemented with any suitable assay. For example, the amount and location of potential therapeutic target proteins may be visualized in intact tissues or cells, permeabilized cells or fixed tissues or cells. In some embodiments, the presence or absence of binding of probe compounds to potential therapeutic target proteins containing at least one redox-sensitive cysteine is detected, at least in part, using "click chemistry." Further, potential therapeutic target proteins containing at least one redox-sensitive cysteine may be detected, isolated, and/or identified by applying a probe compound to intact cells or tissues, cell lysates, or fractionated cell extracts, and then isolating, detecting, and/or identifying proteins bound to the probe compound using immunoaffinity procedures and/or two-dimensional gel procedures for separation followed by mass spectrometry (for example, NMR), chromatographic procedures, or Western blot analysis.

The method of identifying a potential therapeutic target protein may further include measuring the activity of target protein (or an active fragment or domain thereof) at different oxidation levels. The activity of the potential therapeutic target protein may be measured using any suitable assay, including incubating the protein with a substrate molecule in an environment with a particular concentration of an oxidizing agent, such as $H_2O_2$, and then directly or indirectly measuring the level of enzymatic activity of the protein on the substrate. Further, the level of enzymatic activity of the protein can be measured at different concentrations of the oxidizing agent to determine the changes in enzymatic activity at different oxidation levels. For example, the ADP-Glo™ Assay by Promega may be used to measure the enzymatic activity of protein kinases at specific concentrations of an oxidizing agent, such as $H_2O_2$.

EGFR Target Protein

In one example, the method was used to identify epidermal growth factor receptor ("EGFR") as a potential therapeutic target. Studies revealed that EGFR contains a redox-sensitive cysteine referred to as "Cys797." In addition, the ADP-Glo™ Assay by Promega was used to determine the tyrosine kinase activity of recombinant human EGFR kinase domain at different $H_2O_2$ concentrations. It was determined that the activity of EGFR was modified by the concentration of $H_2O_2$, such that the activity increased at $H_2O_2$ concentrations of about 0.05 µM-about 10 µM and the activity decreased at $H_2O_2$ concentrations greater than about 50 µM relative to activity measured at the about 0.05 µM-about 10 µM concentrations. Significantly, the activity of EGFR at $H_2O_2$ concentrations greater than about 50 µM was still higher than the activity of EGFR in its reduced and unoxidized form. Studies also demonstrated that the redox-sensitive cysteine of EGFR (Cys797) is a direct target of $H_2O_2$. Further information concerning the methods of the invention are described in Paulsen et al., Peroxide-dependent sulfenylation of the EGFR catalytic site enhances kinase activity, Nat. Chem. Biol., 8, 57-64 (2011) (including Supplemental Information), which is incorporated by reference herein, in its entirety.

In another example, the method was used to identify protein tyrosine phosphatase 1B ("PTP1B") as a potential therapeutic target. Studies have detected an oxidized form of PTP1B in cells and demonstrated that PTP1B activity is modified by different $H_2O_2$ concentrations.

The invention also provides methods of modifying the activity of proteins that contain at least one redox-sensitive cysteine. Generally, the method includes exposing a target protein to a compound of the invention comprising a nucleophilic warhead and binding element or module. In some embodiments of the method, the target protein is a kinase or phosphatase. In a further embodiment of the method, the target protein contains a redox-sensitive cysteine within its active site. In a further embodiment, the compound covalently binds to a redox-sensitive cysteine within the active site of the target protein. In further embodiments of the method, the compound binds to the target protein and inhibits the activity of the target protein. In a further embodiment of the method, the compound binds to the target protein and enhances the activity of the target protein. In further embodiments, the compound either reversibly or irreversibly binds to the target protein. In a preferred embodiment, the compound binds to a specific form of the target protein, which is in a particular oxidative state. This provides the advantage of increased specificity to the target protein. In some embodiments the method is used to modify the activity of the protein kinase EGFR. In other embodiments, the method is used to modify the activity of the protein phosphatase PTP1B.

The invention also provides a method of treating, preventing, or reducing disease or disease symptoms in a subject or animal suffering from the disease or disease symptoms. Generally, the method includes administering a compound to the subject that modifies the activity of a target protein with at least one redox-sensitive cysteine. In some embodiments, the compound comprises a nucleophilic warhead and binding element. In certain embodiments, the target protein is a kinase or phosphatase. In further embodiments, a therapeutically effective amount of the compound is administered to the subject. In certain embodiments, the subject is an animal. In a preferred embodiment, the animal is a mammal. In a further preferred embodiment, the mammal is a human. In a further preferred embodiment, the administered compound covalently binds to a target protein and inhibits the activity of the target protein. The administered compound may bind either reversibly or irreversibly to the target protein. In some embodiments, the disease can include, but is not limited to, cancer, diabetes, or any other disease where the target protein activity or inactivity is detrimental to the health of the subject.

The invention also provides compounds comprising a nucleophilic warhead and binding element that modify the activity of EGFR. EGFR is the cell-surface receptor for the epidermal growth factor family of extracellular protein ligands. Mutations in EGFR that lead to overexpression and/or increased activity have been associated with a number of different cancers. In studies described above, it was revealed that EGFR activity increased in the presence of higher concentrations of $H_2O_2$ because of the interaction between $H_2O_2$ and the redox-sensitive cysteine of EGFR (Cys797). Similarly, studies also revealed that the sulfenylated form of EGFR, created by exposure to higher concentrations of $H_2O_2$, is more active than forms of EGFR at lower oxidation states. This discovery may have clinical significance as it has been shown that cancer cells have higher $H_2O_2$ concentrations than normal cells.

In certain embodiments, the compounds are inhibitors of EGFR. In further embodiments, the compounds of the invention inhibit the activity of EGFR by covalently binding to EGFR. In further embodiments, the compounds of the invention inhibit the activity of EGFR by reversibly or irreversibly binding to EGFR.

In preferred embodiments, the compounds of the invention are inhibitors of the sulfenylated (e.g., sulfenic acid) form of EGFR. In further preferred embodiments, the compounds of the invention inhibit the sulfenylated form of EGFR by binding to the sulfenylated form of EGFR. In further preferred embodiments, the compounds of the invention are specific irreversible inhibitors of the sulfenylated form of EGFR because the compounds bind irreversibly to the sulfenylated form of EGFR, but not to forms of EGFR with different oxidation states. Further information concerning inhibitors of EGFR is contained in the document titled "Kinase and Phosphatase Inhibitor Project Updates" (Sep. 21, 2012), which is incorporated by reference herein, in its entirety.

A particular embodiment of a compound that modifies the activity of EGFR is a compound of Formula I:

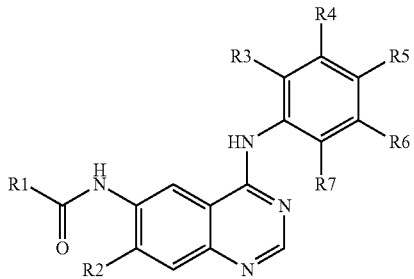

wherein:

R1 is any functional, nucleophilic moiety or warhead that is capable of binding to a sulfenic acid- or sulfenamide-modified cysteine residue. R1 may include, but is not limited to, carbon, nitrogen, sulfur, or phosphorous-based nucleophilic warheads. In certain embodiments, R1 may include a straight, branched, and/or cyclic alkyl functional group containing 1-20 carbon atoms, 0-2 nitrogen atoms, 0-2 oxygen atoms and/or 0-2 sulfur atoms. In certain embodiments, R1 may include more than one functional group.

R2 is a single hydrogen atom or a straight, branched or cyclic alkyl functional group. In certain embodiments, R2 may include more than one functional group. In further embodiments, R2 may include a straight, branched, and/ or cyclic alkyl functional group containing 1-10 carbon atoms, 0-2 nitrogen atoms, 0-2 oxygen atoms and/or 0-2 sulfur atoms.

R3-R7 are atoms that may be the same or different and include, but are not limited to, halogens, hydrogen, carbon, nitrogen, oxygen, sulfur, and/or phosphorus. In certain embodiments, each of R3-R7 may be further connected to additional atoms and/or a straight, branched or cyclic alkyl functional group or functional groups.

Figure 7:
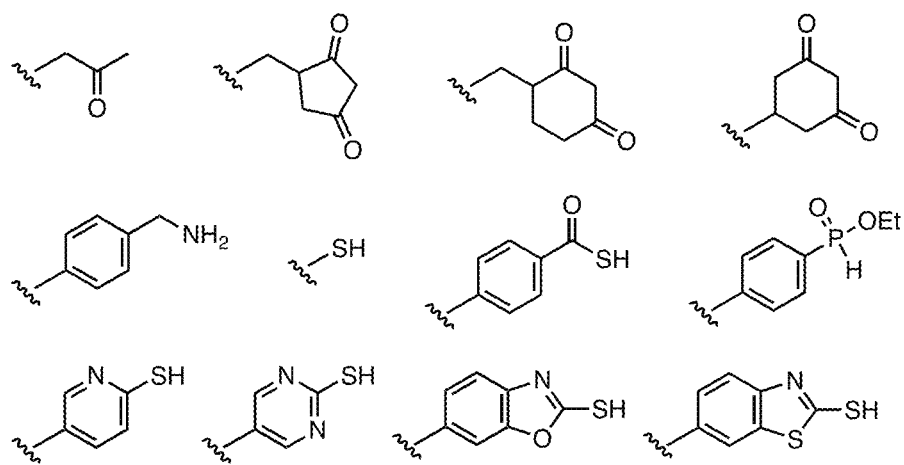
FIG. 7 depicts examples of carbon, nitrogen, sulfur, or phosphorous-based nucleophilic warheads capable of forming a covalent bond with a sulfenic acid- or sulfenamide-modified cysteine residue.
Figure 8A:
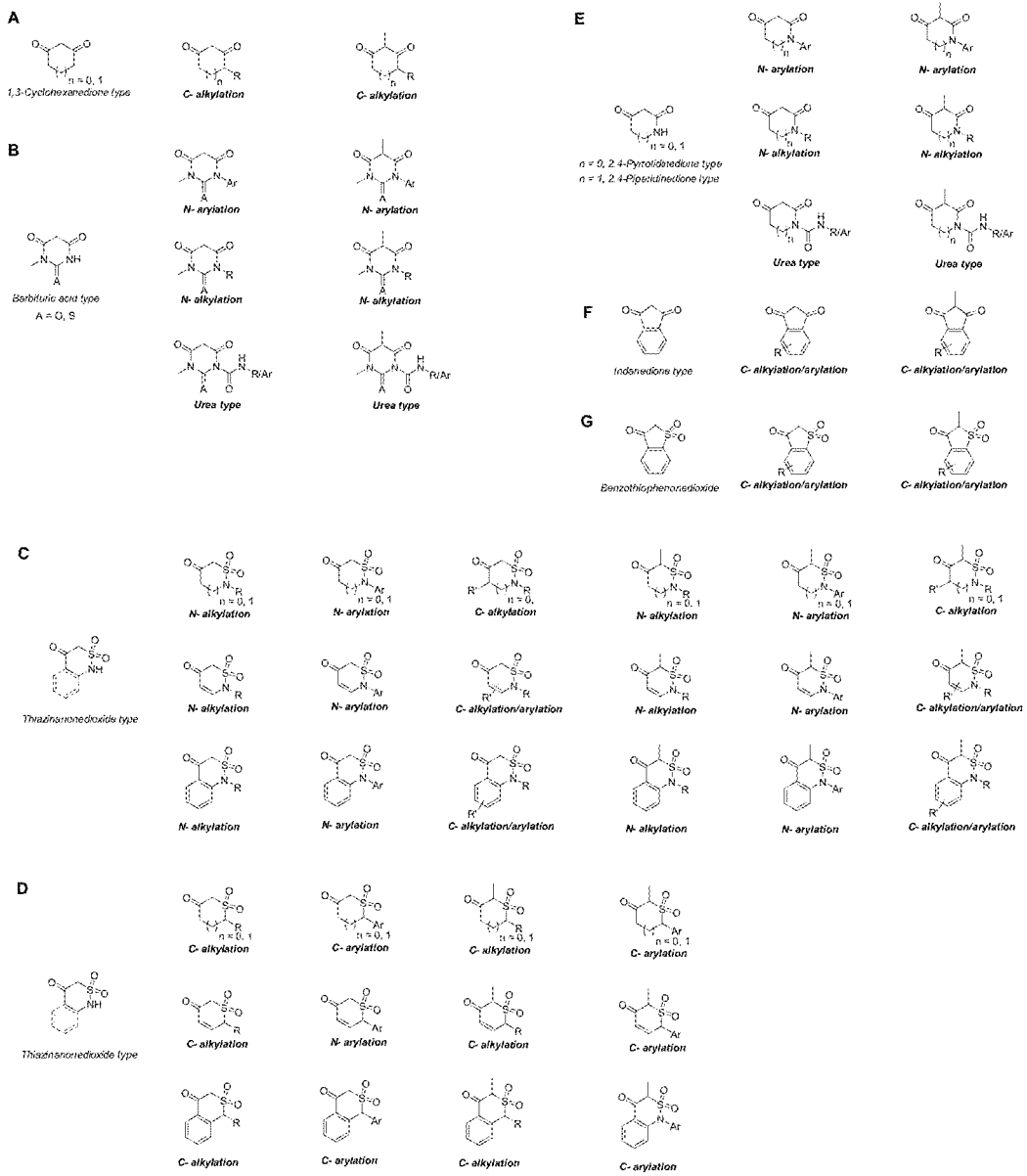
FIG. 8A depicts generic cyclic nucleophilic warheads by chemical "subtype" with appropriate sites for functionalization with binding elements. The subtypes are: (A) 1,3-cyclohexanedione; (B) barbituric acid; (C) thiazinanonedioxide; (D) thiazinanonedioxide; (E) 2,4-Pyrrolidinedione (n=0) and 2,4-Piperidinedione (n=1); (F) indanedione; and (G) benzothiophenonedioxide.
Figure 8B:
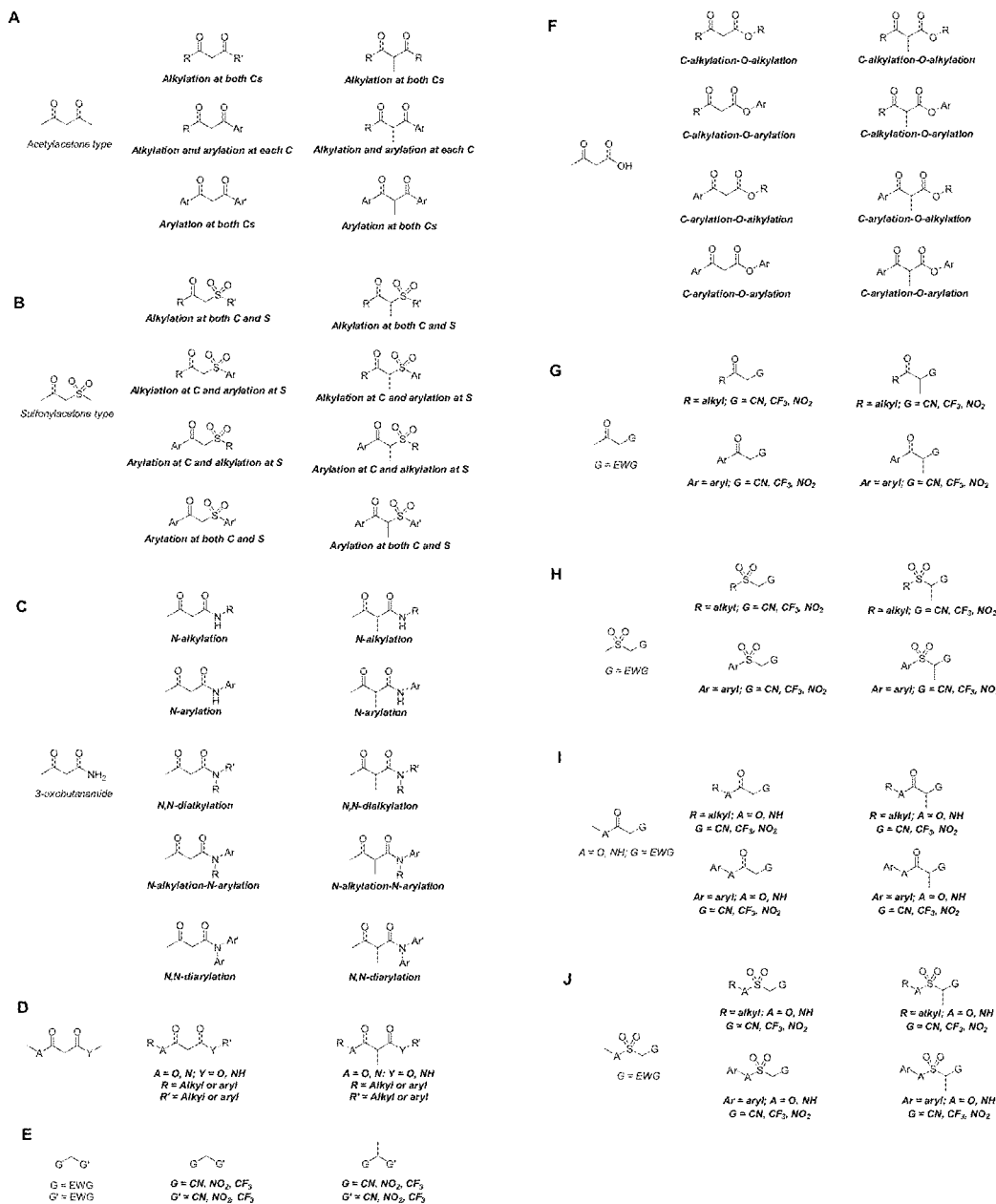
FIG. 8B depicts generic linear nucleophilic warheads by chemical "subtype" with appropriate sites for functionalization with binding elements.
Figure 9:
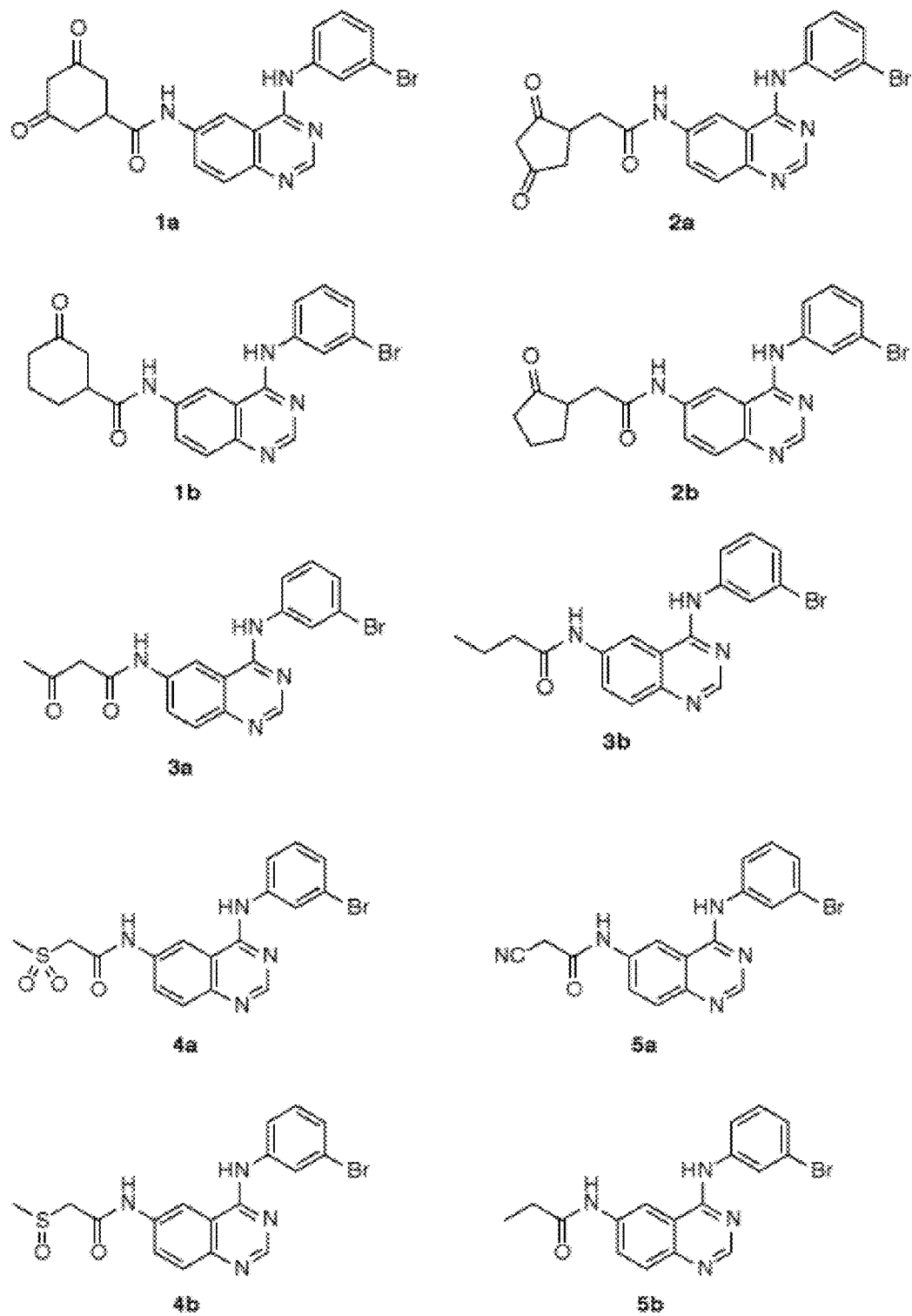
FIG. 9 depicts additional examples of EGFR inhibitor library compounds (a) and control compounds (b).

FIG. 7 provides examples of R1 nucleophilic warhead functional groups. FIG. 8 provides generic cyclic (FIG. 8A) and linear (FIG. 8B) nucleophilic warheads by chemical subtypes, showing the appropriate sites for functionalization with binding elements. FIG. 9 provides EGFR Inhibitor compounds (a) and control compounds (b).

FIG. 10A shows preferred nucleophilic warheads ranked in order by reactivity and binding properties. Preferred nucleophilic warheads may have a reactivity ranging from about 20 min$^{-1}$ to about 120 min$^{-1}$, preferably from about 20 min$^{-1}$ to about 200 min$^{-1}$. The warheads are ranked based on their pseudo $1^{st}$ order rate constants. The warheads have a number of polar and non-polar functionalities for fortuitous interactions with the target. The additional heteroatoms (like N or S or O) are expected to provide additional aqueous solubility. The warheads themselves are not expected to provide binding affinities per se, however, if they do, it is an added advantage. Some of the affinities of the warheads by themselves are expected to be in the millimolar (mM) range; however, micromolar (µM) would be preferred and possible. In general, nucleophilic warheads may have a binding property that ranges from high mM (i.e., 10 mM) to low uM (i.e., 10 uM). The preferred nucleophilic warheads depicted in FIG. 10A may be modified and ranked based on reactivity, solubility, and binding (FIG. 10B).

In one specific embodiment, a compound that modifies the activity of EGFR has the following Formula II:

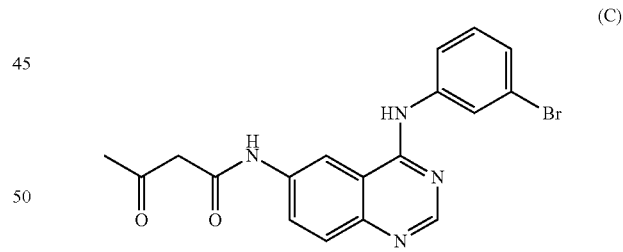

Compound C, pictured above, is an example of a compound that inhibits the activity of EGFR. Experimental results, depicted in FIG. 11, have demonstrated that Compound C (5 µM) provides greater inhibition in conditions having higher concentrations of $H_2O_2$ (50 µM). The Western blots show phosphorylated EGFR (pEGFR) and total EGFR of A431 cells stimulated with the indicated concentrations of EGF (100 ng/ml), $H_2O_2$ (50 µM) for 10 minutes, and Compound C for the indicated treatment times. These study results suggest that Compound C (i.e., compound 3a of FIG. 9) more potently inhibits the sulfenylated form of EGFR than reduced forms of EGFR. The compounds (1a, 2a, 4a, 5a) of FIG. 9 are further examples of EGFR inhibitors that target the sulfenylated form of EGFR.

Figure 12:
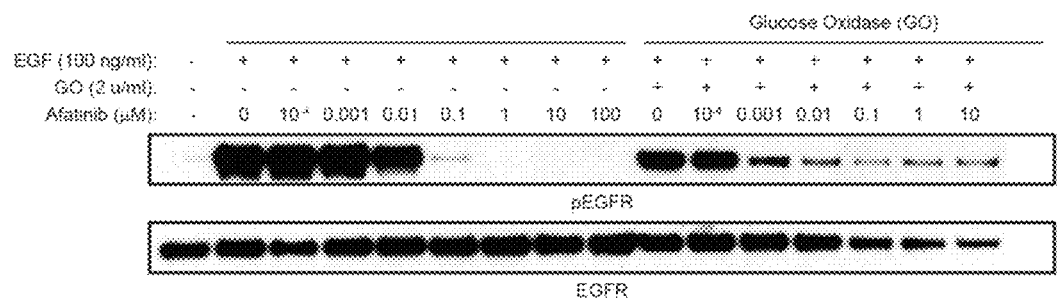
FIG. 12 depicts the results of chronic hydrogen peroxide stress that generates a population of EGFR resistant to Afatinib, an irreversible EGFR inhibitor.
Figure 13:
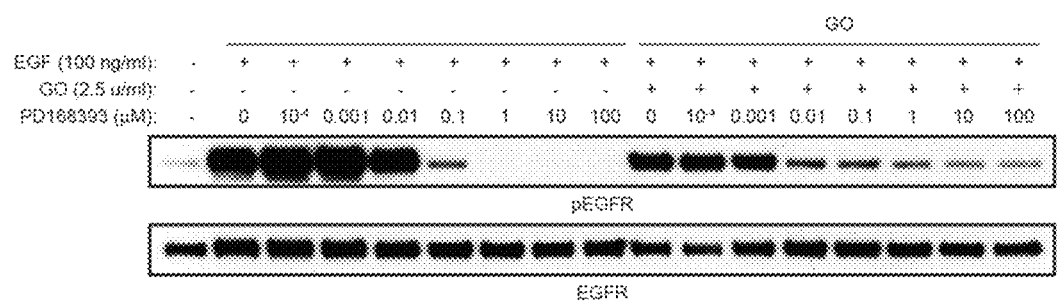
FIG. 13 depicts the results of chronic hydrogen peroxide stress that generates a population of EGFR resistant to PD168393, an irreversible EGFR inhibitor.

After A431 cells were treated with and without glucose oxidase for 3 hours and varying concentrations of Afatinib, a known irreversible EGFR inhibitor, for one hour, the cells were washed and stimulated with EGF for 5 minutes (FIG. 12). The cells were washed and lysed and western blot analysis was performed. The results depicted in FIG. 12 demonstrate that the reduced form of EGFR was inhibited more by Afatinib than the oxidized form. More specifically, chronic hydrogen peroxide stress generated a population of EGFR resistant to Afatinib. Similarly, chronic hydrogen peroxide stress also generated a population of EGFR resistant to PD168393 irreversible EGFR inhibitor (see, FIG. 13).

Figure 14:
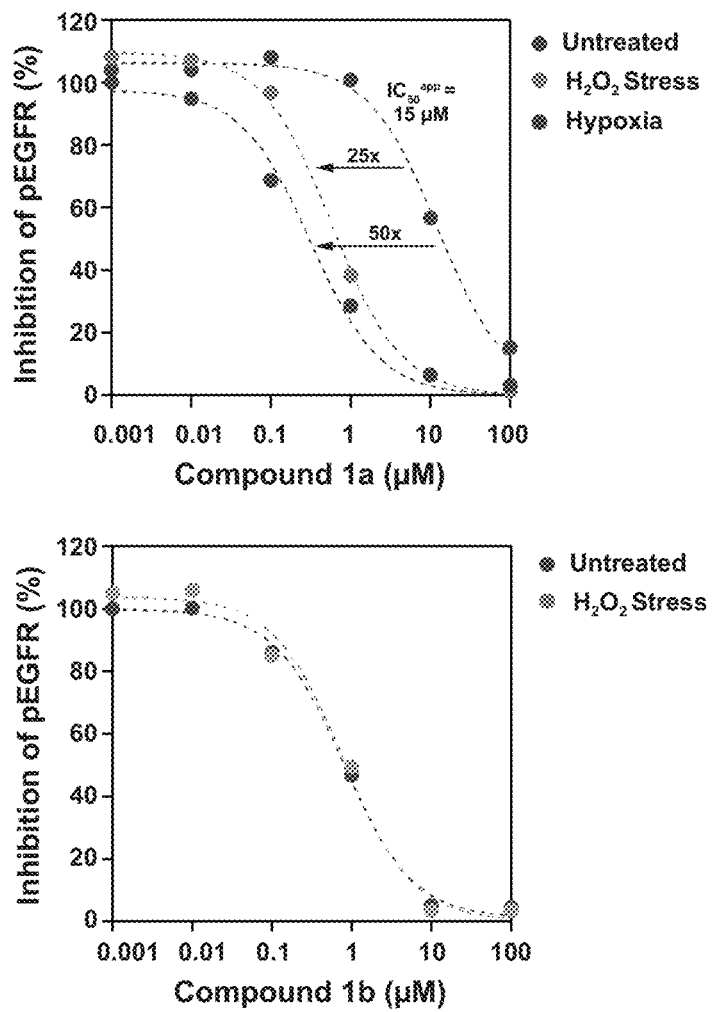
FIG. 14 depicts a comparison of the inhibition of pEGFR under varying conditions of a compound with the nucleophilic warhead (1a) to that without the nucleophilic warhead (1b).

Several of the targeted covalent inhibitor compounds were assayed for sulfenyl EGFR. FIG. 14 depicts the inhibition of phorphorylated EGFR (pEGFR) with hydrogen peroxide stress and further inhibition under conditions of hypoxia. Incubation occurred for about 1 hour. Treatment with varying increasing concentrations of Compound 1a (of FIG. 9) shows a decrease or inhibition of pEGFR in untreated compared to the oxidized form of EGFR ($H_2O_2$ stress, Hypoxia), while in contrast the control, Compound 1b (of FIG. 9) did not show much difference between untreated and under hydrogen peroxide stress. The concentrations of the compounds ranged from about 0 μM to about 75 μM for Compound 1a; for Compound 2a, about 0 μM to about 50 μM; and for Compound 3a, about 0 μM to about 50 μM. Compound 1a was also found to have time-dependent inhibition and redox-modulated inhibition as demonstrated by the increased inhibition in the presence of $H_2O_2$ stress. Comparing Compound 1a to Compound 1b demonstrated that covalent inhibition requires the nucleophilic warhead. Western blots demonstrated that Compound 2a and Compound 3a exhibited higher affinity for EGFR compared to Compound 1a, where PD168393 was a positive EGFR inhibitor control (see, FIG. 15) Inhibition with the EGFR inhibitor compounds (1a, 2a, and 3a) is dose-dependent, i.e., the more inhibitor, the more inhibition may be observed or higher affinity for EGFR. The Western blots were performed using a primary antibody for phospho-EGFR (pY1068, Abcam, 1:1000) and for EGFR (1005, Santa Cruz Biotechnology, 1:200), while the secondary antibody was an anti-rabbit IgG-HRP (Calbiochem, 1:30000-1:50000).

Further biological studies of the inhibitor compounds are shown in TABLE 3. The half maximal inhibitory concentration (IC50) is a measure of the effectiveness of a compound to inhibit a biological process or function, such as in this case, EGFR in A431 cells, with hydrogen peroxide ($H_2O_2$) or glutathione (GSH). PD168393 is a known irreversible EGFR inhibitor. The IC50 values of compounds 1a-5a decrease under oxidative (i.e., $H_2O_2$) conditions when compared to EGF control. Whereas, such trend is not observed with PD168393, and the observed IC50 values for the EGFR inhibitor under varying conditions were fairly similar. Additionally, when tested under reducing conditions (GSH), the IC50 values of compounds 1a-5a increased indicating suitability of RBIs under oxidative stress conditions.

The studies involved pre-treating A431 cells with $H_2O_2$ (200 μM, 5 min), incubating with variable compound concentrations (0, 0.01 μM, 0.1 μM, 1 μM, 10 μM, and 100 μM) for 1 hour, and stimulating with EGF (100 ng/ml). Cells were also pre-treated with GSH (10 mM, 1 hour), incubated with variable compound concentrations (0, 0.01 μM, 0.1 μM, 1 μM, 10 μM, and 100 μM) for 1 hour, and stimulated with EGF (100 ng/ml). IC50 values were determined by Western blot analysis of EGFR autophosphorylation and calculated using KaleidaGraph™ software.

The microsomal stability assay may be used as an indicator of in vivo stability of a drug candidate which affects the pharmacokinetics. Microsome stability of Compounds 1a-5a was evaluated using human and mouse liver microsomes with PD168393 as a reference. Compounds 1a-5a in TABLE 3 exhibited low clearance and had good bioavailability compared to PD168393 control. For example, in human liver microsome, Compound 2a had a $t_{1/2}$>100 min compared to $t_{1/2}$ of 10 min for PD168393.

Plasma stability of drug candidates may be essential for maintaining acceptable drug concentration and half-life in order to achieve desirable pharmacological effects. Compounds 1a to 5a were evaluated for plasma stability in mice with PD168393 as the reference. At time points of 1 hour, 4 hours, and 8 hours, Compounds 1a-5a showed comparatively higher stability than PD168393. At a time point of 24 hours, Compounds 1a-5a and PD168393 were almost completely degraded.

TABLE 3

| Compound | Potency vs. EGFR | | | Microsome Stability | | Plasma Stability in Mice (20 mg/kg IP) | | | |
|---|---|---|---|---|---|---|---|---|---|
| | IC50 (μM) | IC50 + $H_2O_2$ (μM) | IC50 + GSH (μM) | Human $t_{1/2}$ min (Cl μl/min/mg) | Mouse $t_{1/2}$ min (Cl μl/min/mg) | 1 h (μM) | 4 h (μM) | 8 h (μM) | 24 h (μM) |
| 1a | 13.2 | 0.4 | 5.7 | 29 (24.2) | 16 (42.1) | 11.6 | 2.6 | 0.48 | <0.022 |
| 2a | 5.0 | 0.4 | 2.0 | 111 (6.3) | 59 (11.8) | 14.7 | 1.1 | 0.18 | <0.022 |
| 3a | 1.0 | 0.3 | ND | 17 (39.7) | 4 | 29.1 | 1.1 | 0.1 | <0.025 |
| 4a | 1.2 | 0.2 | ND | 29 (24.3) | 17 | 6.7 | 0.7 | 0.1 | <0.007 |
| 5a | 1.5 | 0.3 | ND | 37 (18.8) | 4 | 18.6 | 1.7 | 0.1 | 0.01 |

TABLE 3-continued

| | Potency vs. EGFR | | | Microsome Stability | | Plasma Stability in Mice (20 mg/kg IP) | | | |
|---|---|---|---|---|---|---|---|---|---|
| | | | | Human $t_{1/2}$ min | Mouse $t_{1/2}$ min | | | | |
| | IC50 | IC50 + $H_2O_2$ | IC50 + GSH | (Cl $\mu$l/min/ | (Cl $\mu$l/min/ | 1 h | 4 h | 8 h | 24 h |
| Compound | ($\mu$M) | ($\mu$M) | ($\mu$M) | mg) | mg) | ($\mu$M) | ($\mu$M) | ($\mu$M) | ($\mu$M) |
| PD168393 | 0.03 | 0.02 | 0.13 | 10 (72.4) | 3 | 2.0 | 0.04 | 0.05 | <0.005 |

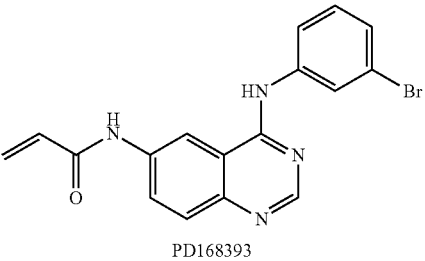 [SMILES: C=CC(=O)Nc1ccc2ncnc(Nc3cccc(Br)c3)c2c1]

The invention also encompasses methods for synthesizing redox-based EGFR inhibitors. The general method for synthesizing redox-based EGFR inhibitors comprises converting a carboxylic acid on a nucleophilic warhead to an acid chloride under neutral reaction conditions and condensing the acid chloride with a primary amine present on a functional binding element. An example of the general method for synthesizing compounds of the invention that modify the activity of the epidermal growth factor receptor protein or EGFR is depicted in FIG. 16, Scheme 1, specifically, the strategy of coupling protected nucleophilic warheads to the quinazoline based scaffold. FIG. 16, Scheme 2 depicts a synthesis reaction for an inventive compound (RBI) that inhibits the activity of EGFR. In FIG. 16, Scheme 2, the nucleophilic warhead carboxylic acid was converted to its corresponding acid chloride and subsequent coupling to form the amide linkage. In order to maintain chemoselectivity, the β-diketone component of the warhead was protected as a its methyl-enone. The carboxylic acid was converted to the corresponding acid chloride using Ghosez's reagent (1.1 eq) and aminoquinazoline (1.0 eq) was added to the same reaction flask under basic conditions (pyridine, 3 eq) to give a corresponding amide in good yields. The warhead deprotection was achieved by subjecting it to ceric ammonium nitrate mediated reflux conditions. FIG. 16, Section 3 identifies additional redox-based EGFR inhibitors that can be synthesized using Scheme 1.

One preferred EGFR inhibitor compound may have a generic Formula III, i.e., 4-anilinoquinazoline core:

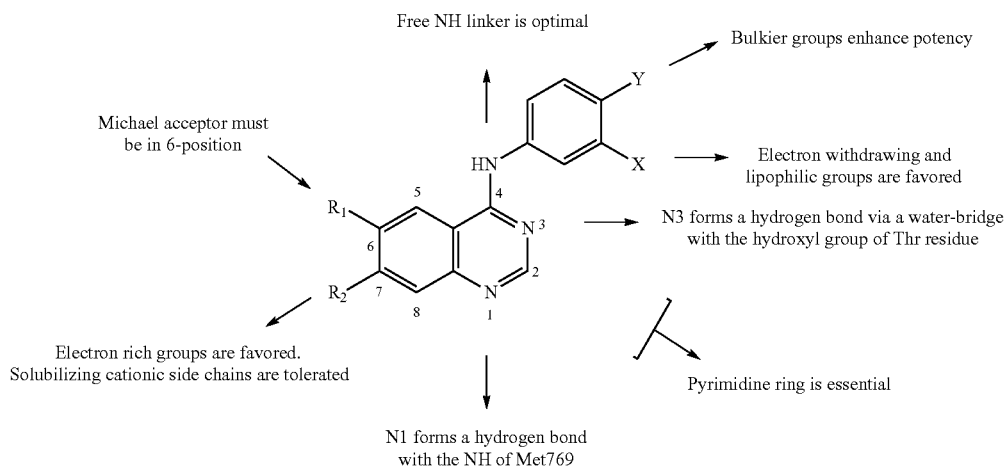

R1 at position 6 is a Michael acceptor, such as for example, a nucleophilic warhead or an acrylamide warhead;

R2 at position 7 is favored by electron-rich groups, where solubilizing cationic side chains are tolerated. R2 may be any alkoxy group;

X is any halogen or any alkyl group; and

Y is any halogen or bulkier alkyl group.

Initial structure-activity relationship studies for the 4-anilinoquinazoline series of reversible EGFR inhibitors resulted in the identification of many structural features. For example, it was found that pyrimidine ring is important as both N1 and N3 are involved in H-bonding. Moreover, the Michael acceptor is essentially fixed at position 6 Inhibitor potency increases with the presence of electron rich groups and cationic side chains on position 7. The aniline ring having position 3' and 4' substituted with electron withdrawing, lipophilic groups are found to result in enhanced inhibitory effect.

The effects of incorporating various structural changes and substitutions are identified and the IC50 rates are presented. Although the irreversible EGFR inhibitors were shown to be effective inhibitors, their bioavailability was not as good primarily due to their low solubility under physiological conditions. To improve the pharmacokinetic properties of such compounds, water-solubilizing groups are incorporated on quinazoline core. Position carbon 6 is reserved for Michael acceptors, usually acrylamide moiety and position 7 is utilized for incorporating solubilizing cationic side chain. In another approach, water-solubilizing groups such as dialkylamine are incorporated at the end of Michael acceptor. This serves dual purpose—of a base involved in the deprotonation of catalytic Cysteine via cyclic catalytic mechanism and exerting an inductive effect to enhance the rate of Michael addition reaction. Several kinase inhibitors were synthesized on these principles and many are in various stages of clinical trials.

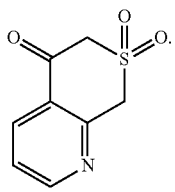

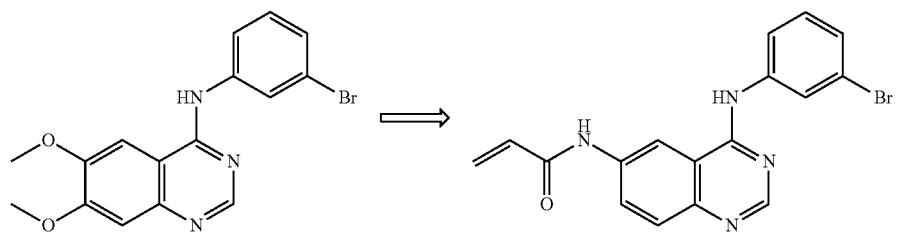

EGFR IC50 = 0.03 nM
Reversible inhibitor (1)

PD 168393
EGFR IC50 = 0.7 nM
Irreversible inhibitor

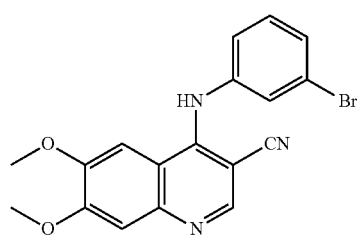

EGFR IC50 = 190 nM
Reversible inhibitor (2)

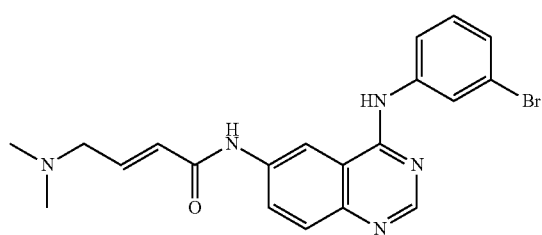

EGFR IC50 = 11 nM
Irreversible inhibitor (3)

-continued
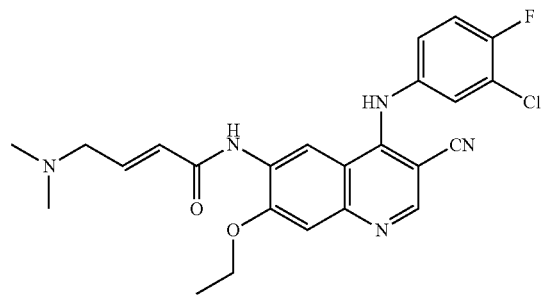
EKB-569
EGFR IC50 = 8 nM
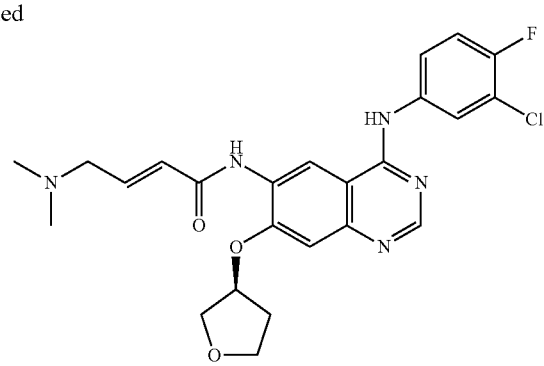
Afatinib, BIBW-2992
EGFR IC50 = 0.5 nM
Irreversible inhibitor
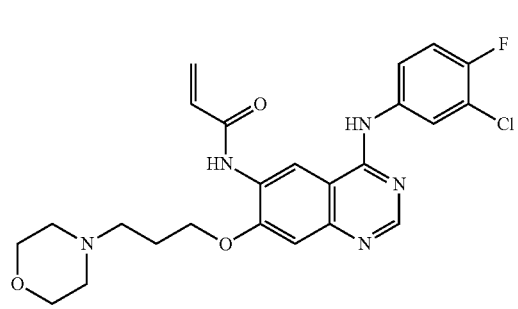
Canertinib, Cl-1033
EGFR IC50 = 1.5 nM
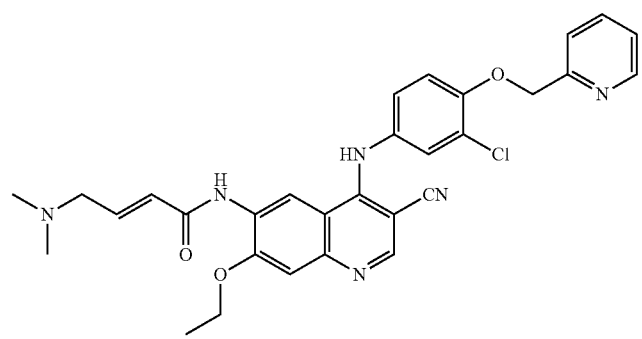
Neratinib, HKI-272
EGFR IC50 = 92 nM
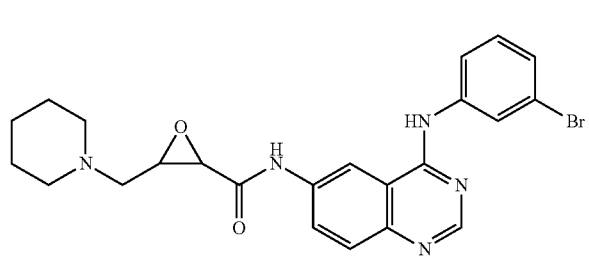
EGFR IC50 = 1.24 nM (4)
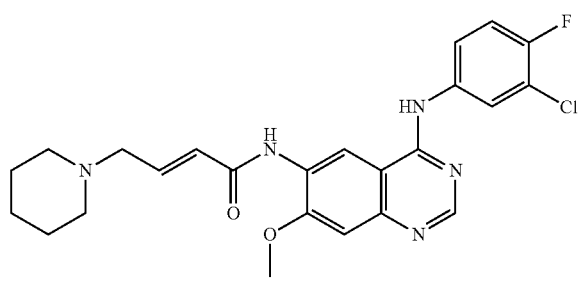
Dacomitinib, PF-00299804
EGFR IC50 = 8nM
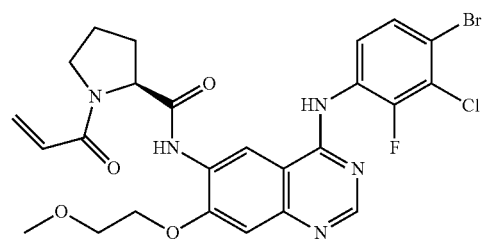
EGFR (A431) IC50 = 6 nM (5)
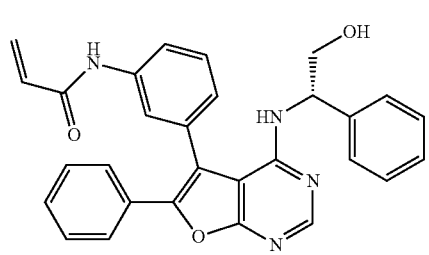
EGFR IC50 = 7 nM (6)

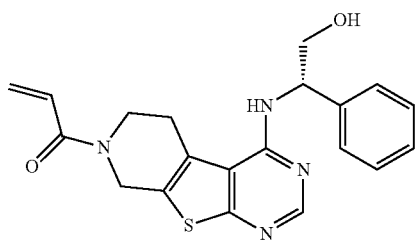

EGFR IC50 = 8nM (7)

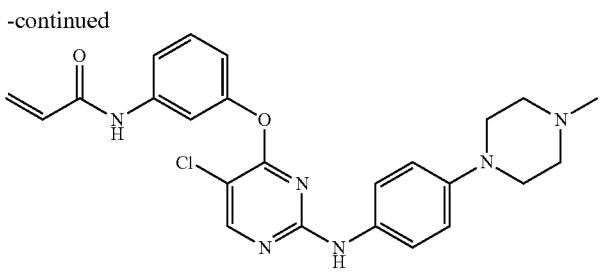

EGFR (T90M) IC50 = 2 nM (8)

A more preferred redox-based EGFR inhibitor may be based on the EGFR inhibitor, PD168393, and have a generic Formula IV:

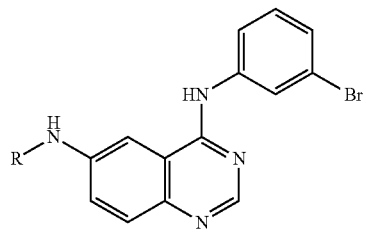

where the R group may be selected from the following substituents:

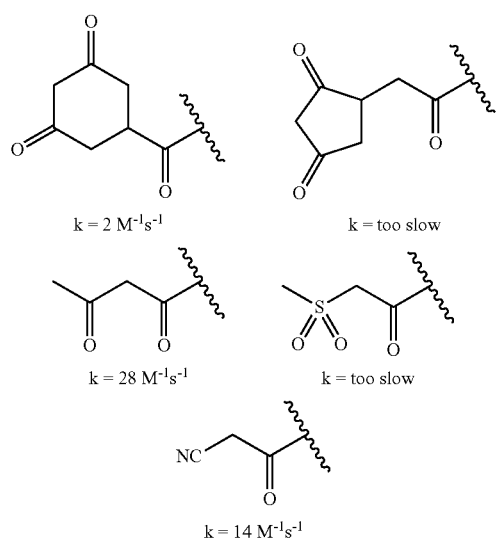

The thiol(ate) reactive acylamide group of PD168393 was replaced with sulfenic acid specific warheads, which were identified by screening with a dipeptide-SOH model. Although the inhibitors showed enhanced activity with increased oxidative stress, they were less potent than PD168393.

Further designing to produce even better redox-based EGFR inhibitors below resulted in a modified Afatinib (A, IC50=0.5 nM) and a modified compound identified (B, IC50=6 nM) below. Modifying Afatinib (A, C) was ideal because it incorporated all of the desirable structural elements that result in an ideal irreversible inhibitor. For example, position 6 has a Michael acceptor coupled with a dimethylamino group at the terminal position. While, position 7 has a tetrahydrofuranyloxy substitution which is both electron rich and solubilizing via H-bonding potential. The generic compound identified in (B) was selected, in addition to the above-mentioned factors, because it incorporates a rigid ring at position 6 resulting in the proper orientation and distance between the warheads and the 4-aminoquinazoline moiety. Also, the core B presents opportunities to explore modifications on position 4 of N-aryl substitution as well as position 7 of quinazoline (D).

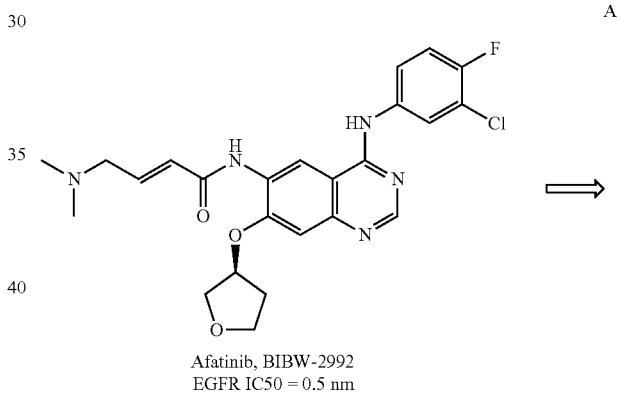

Afatinib, BIBW-2992
EGFR IC50 = 0.5 nm

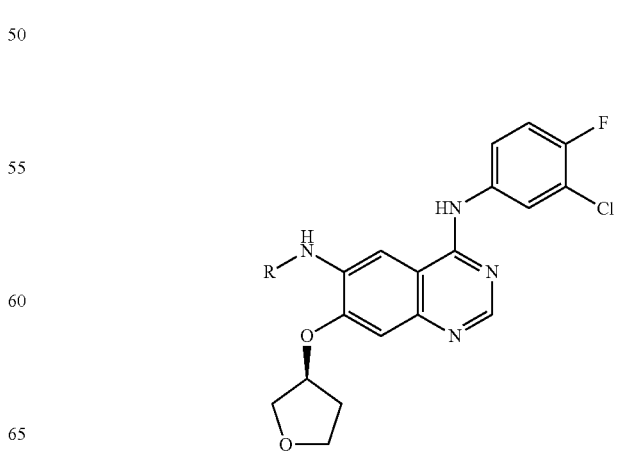

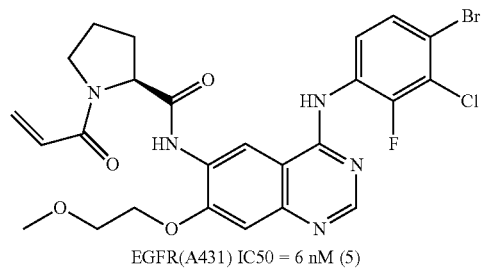
EGFR(A431) IC50 = 6 nM (5)
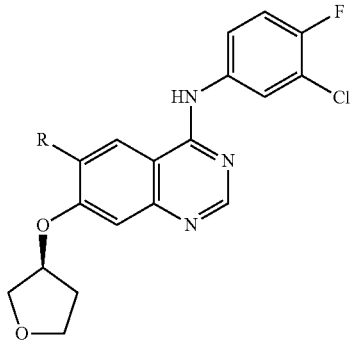
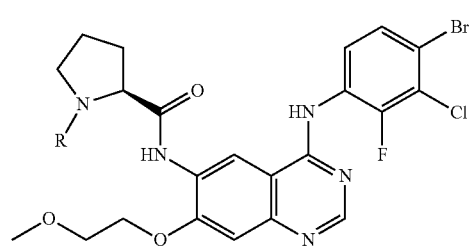
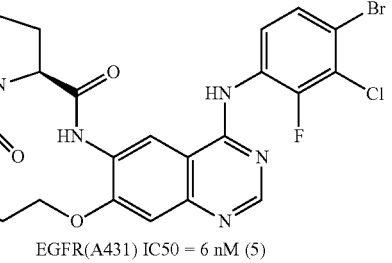
EGFR(A431) IC50 = 6 nM (5)
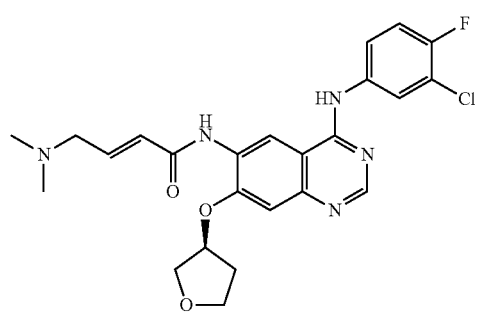
Afatinib, BIBW-2992
EGFR IC50 = 0.5 nm
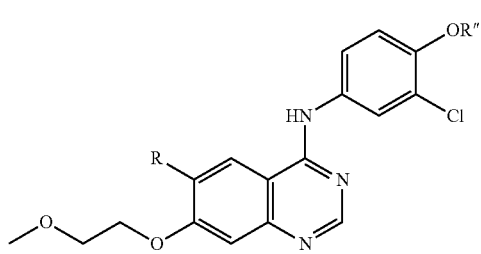
The synthesis of quinazoline core may preferably be optimized as demonstrated in the below synthesis of EGFR inhibitors. The title compound was purified by HPLC to about greater than or equal to 98% purity.

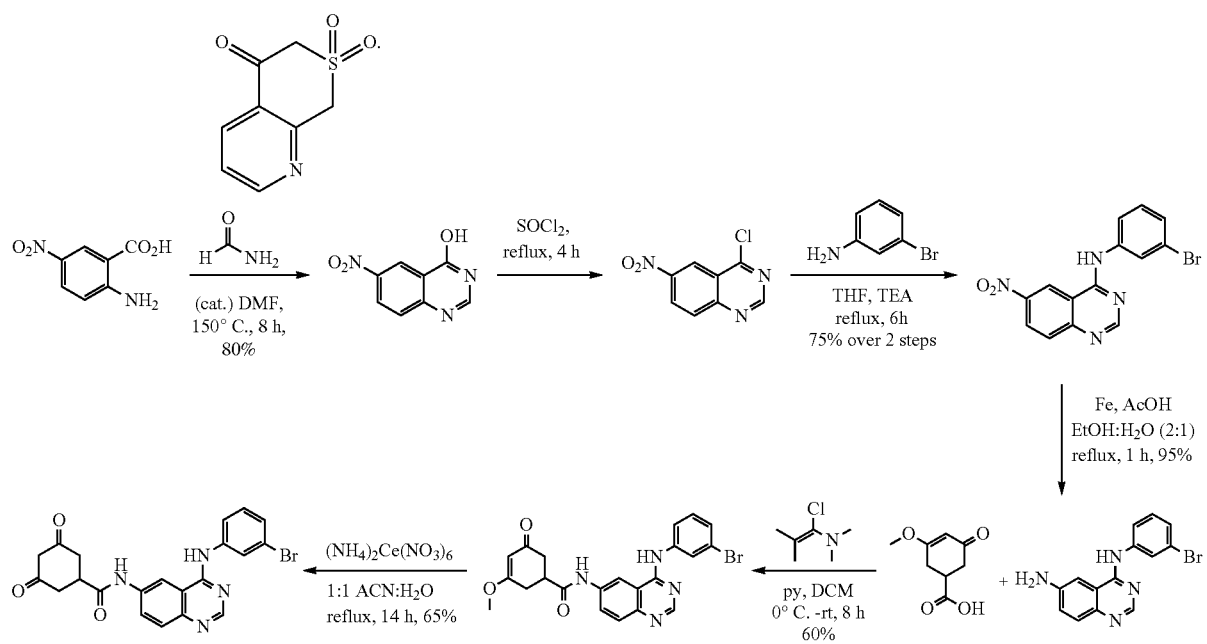
Synthesis of additional EGFR inhibitors that were also purified by preparative HPLC to about greater than or equal to 98% purity is presented below.
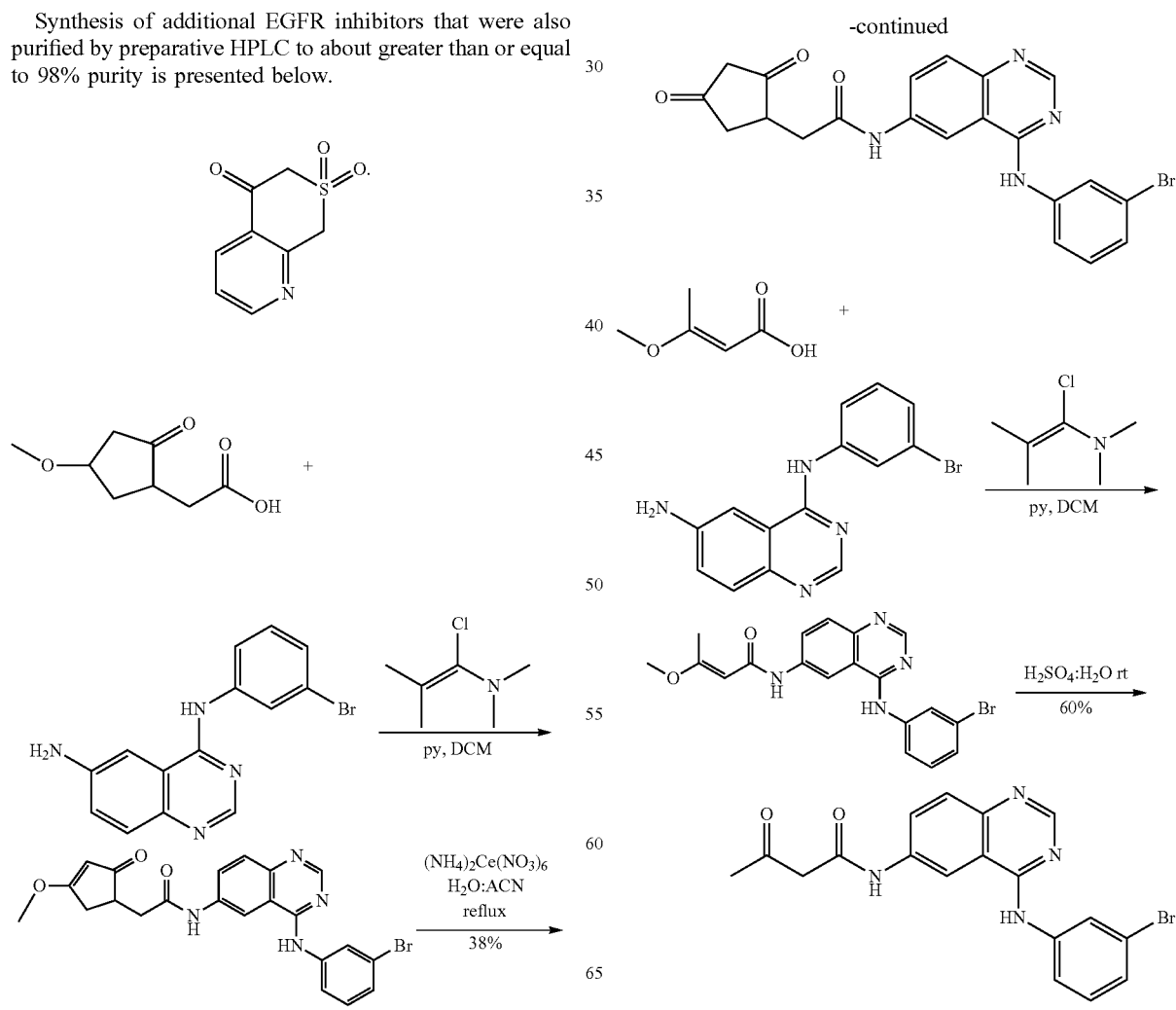

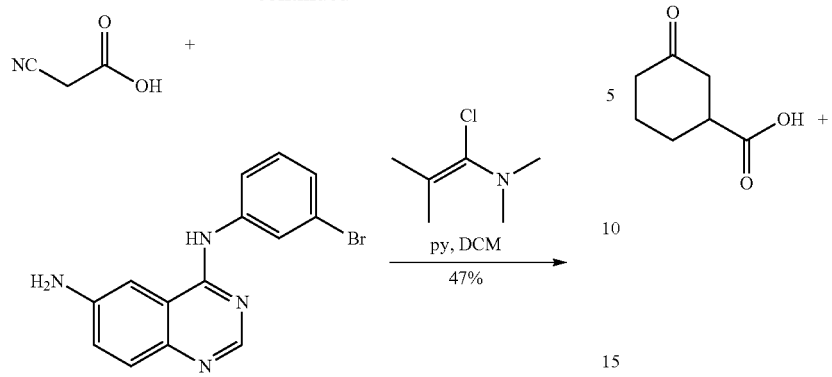
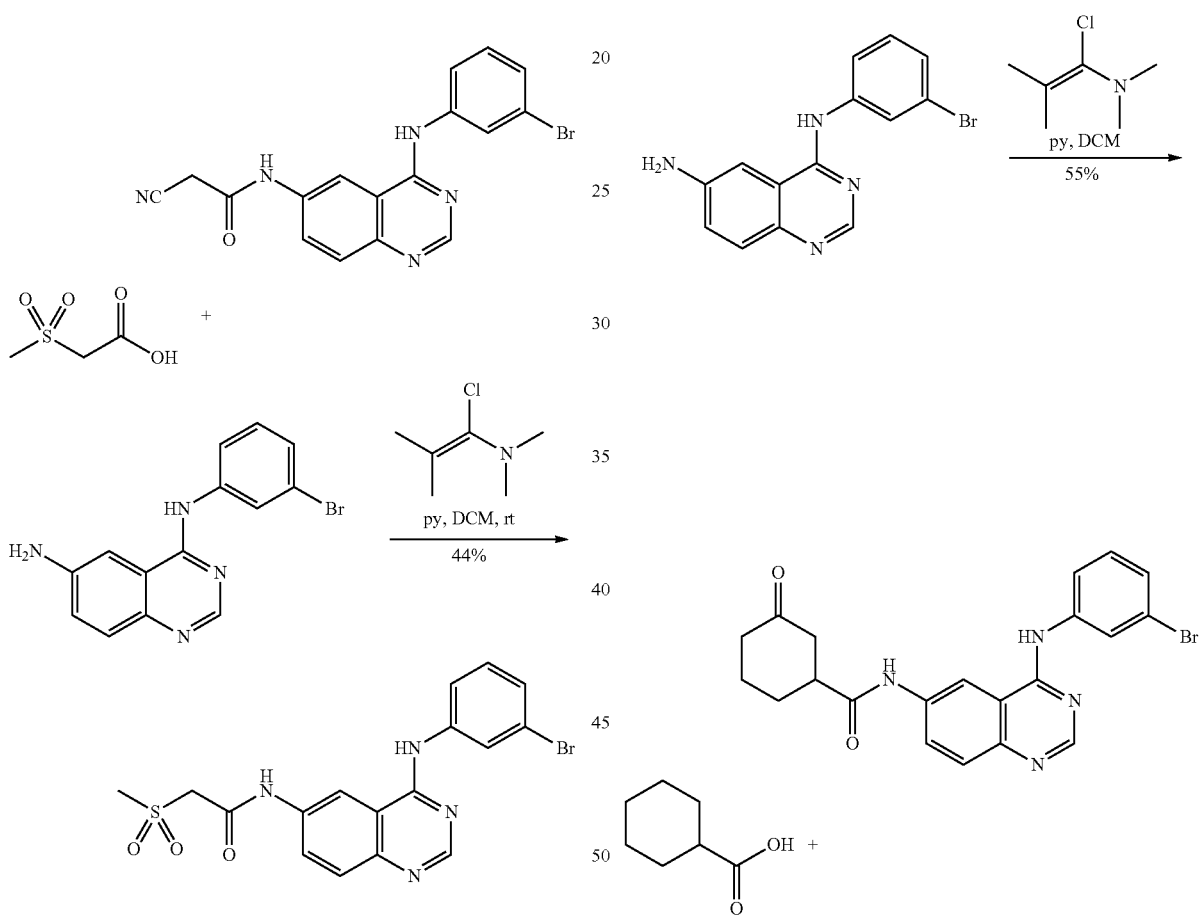
Whereas, synthesis of control compounds may be performed following the below schemes. Again, all of the title compounds were purified by preparative HPLC to greater than or equal to about 98% purity.
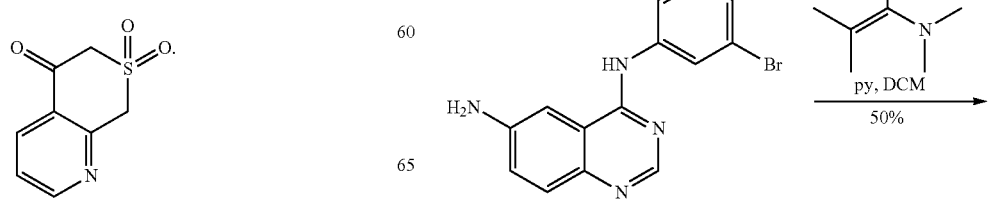

35
-continued
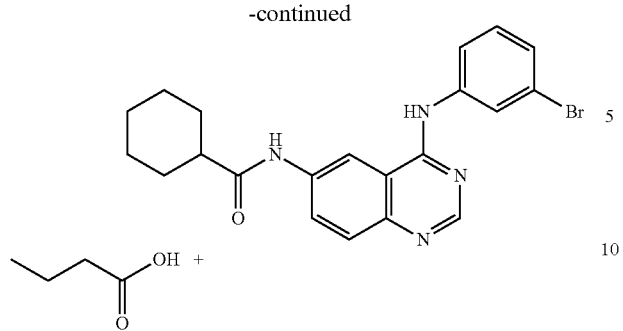
36
-continued
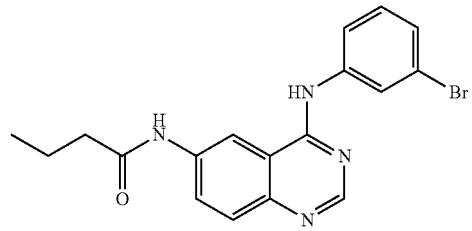 [SMILES: CCCC(=O)Nc1ccc2ncnc(Nc3cccc(Br)c3)c2c1]
Alkyne-functionalized probes were also synthesized following the following schemes, such that the title compounds are purified by preparative HPLC to greater than or equal to 98% purity.
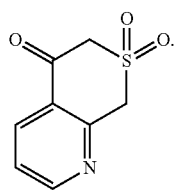
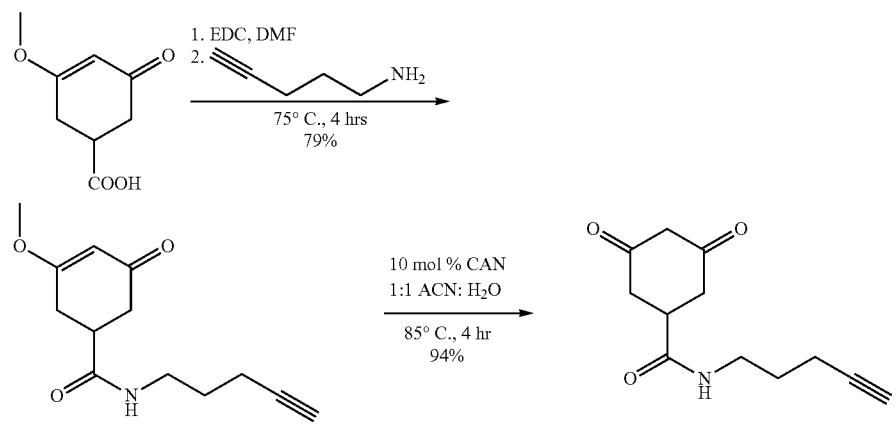

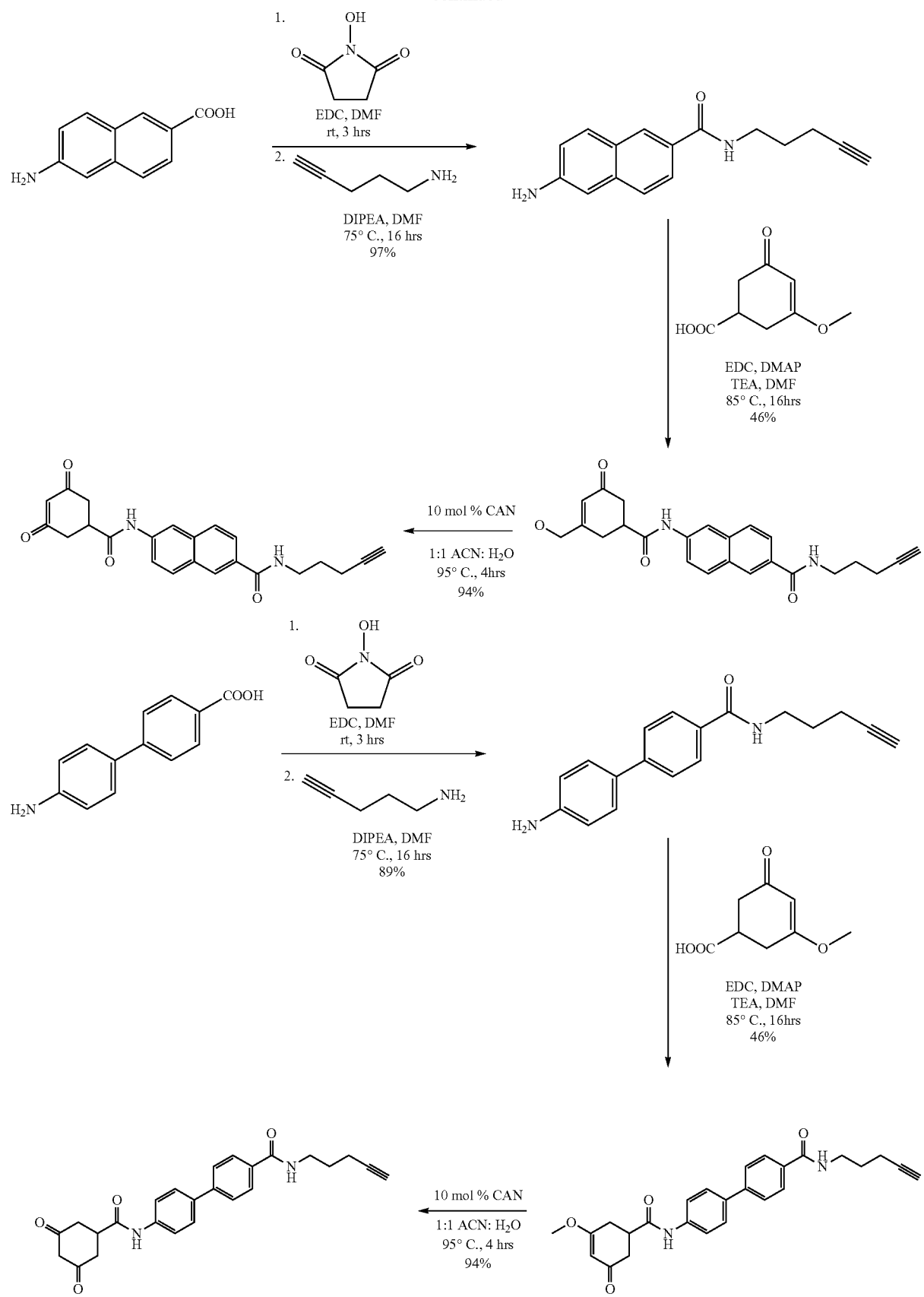

A generic compound of Formula V below may substitute R1 with the sulfenic acid specific warheads identified as having amide linkages of a chain length ranging from 3 to 5 atoms and direct linkages with a chain lengths of 2-3 or 4 atoms. For the other substituents, R2 may be any alkoxy (or H); R3 may be hydrogen (H), any halogen (X), an alkyl, or an alkoxy; and similarly, R4 may be H, X, an alkyl, or an alkoxy.

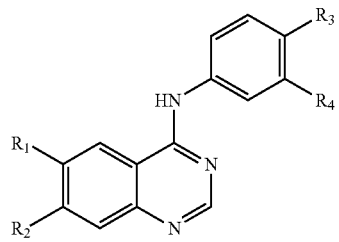

Amide linkage (chain length 3 or 5 atoms)

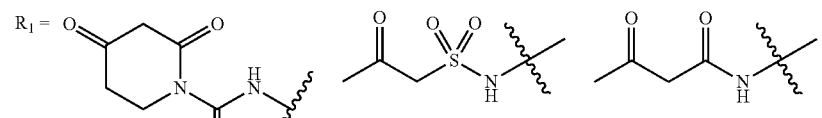

$k = 232\ M^{-1}s^{-1}$       $k = 23\ M^{-1}s^{-1}$       $k = 24\ M^{-1}s^{-1}$

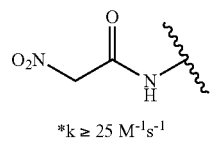 [SMILES: *NC(=O)C[N+](=O)[O-]]  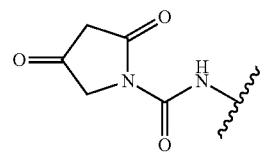

*$k \geq 25\ M^{-1}s^{-1}$       *$k \geq 25\ M^{-1}s^{-1}$

Direct linkage (chain length 2-3 atoms)

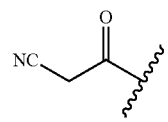  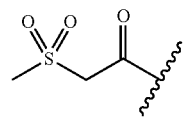  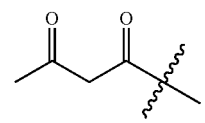

$k = 205\ M^{-1}s^{-1}$       $k = 107\ M^{-1}s^{-1}$       $k = 64\ M^{-1}s^{-1}$

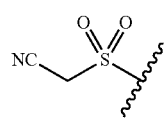  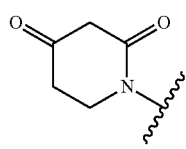  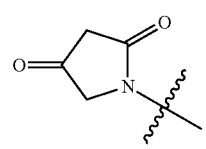

$k = 1300\ M^{-1}s^{-1}$       $k = 1050\ M^{-1}s^{-1}$       $k = 355\ M^{-1}s^{-1}$

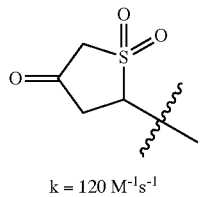 [SMILES: *C1CC(=O)CS1(=O)=O]  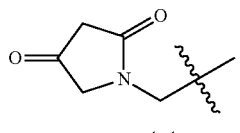  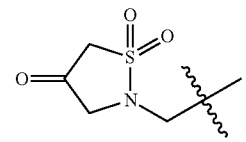

$k = 120\ M^{-1}s^{-1}$       $k = 355\ M^{-1}s^{-1}$       $k = 120\ M^{-1}s^{-1}$

Direct linkage (chain length 4 atoms)

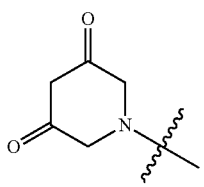  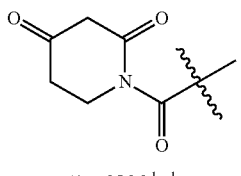  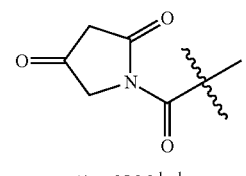

*$k \geq 25\ M^{-1}s^{-1}$       *$k \geq 25\ M^{-1}s^{-1}$       *$k \geq 25\ M^{-1}s^{-1}$ The sulfenic acid specific warheads identified above, may be attached by an amide linkage and/or directly to the core. Based on the attachments, these warheads may be divided into two groups and reported with their second order rate constants. It is apparent from the reported $k_{obs}$ values that for linear warheads, direct linkage has distinct advantage of enhanced sulfenic acid reactivity. In the case of cyclic nucleophiles, both direct as well as amide (urea) mediated linkage would show substantially enhanced reactivity compared to dimedone. Finally, since in PD168393 (and other EGFR inhibitors), the thiol reactive amide site has a distance of 4 atoms from quinazoline site, so it is important to divide the warheads on the bases of atom length from the quinazoline core as well. Chain length variation from 2-5 atoms may also be incorporated as well.

The thiol reactive site in PD168393 (Compound 1, A) below is at position 4 from the core. Compound 2 and Compound 3 (B) represent sulfenic acid reactive warhead containing structures which are proposed to mimic PD168393 in terms of the reactive site distance from core. Compound 2 maintains the similarity to PD168393 in terms that the site of attachment between the core and warhead is an amine.

In the case of Compound 3, the site of attachment is changed from an amine to a carbonyl. This attachment is different from a traditional amine-mediated approach but not without precedence. International patent publications, WO2005/26156 and WO2005/105761, describing the synthesis and activity against receptor tyrosine kinases, particularly EGFR tyrosine kinase support the carbonyl attachment site. One potential advantage of Compound 3 over Compound 2 would be that it shows a structural rigidity and orientation quite similar to PD168393.

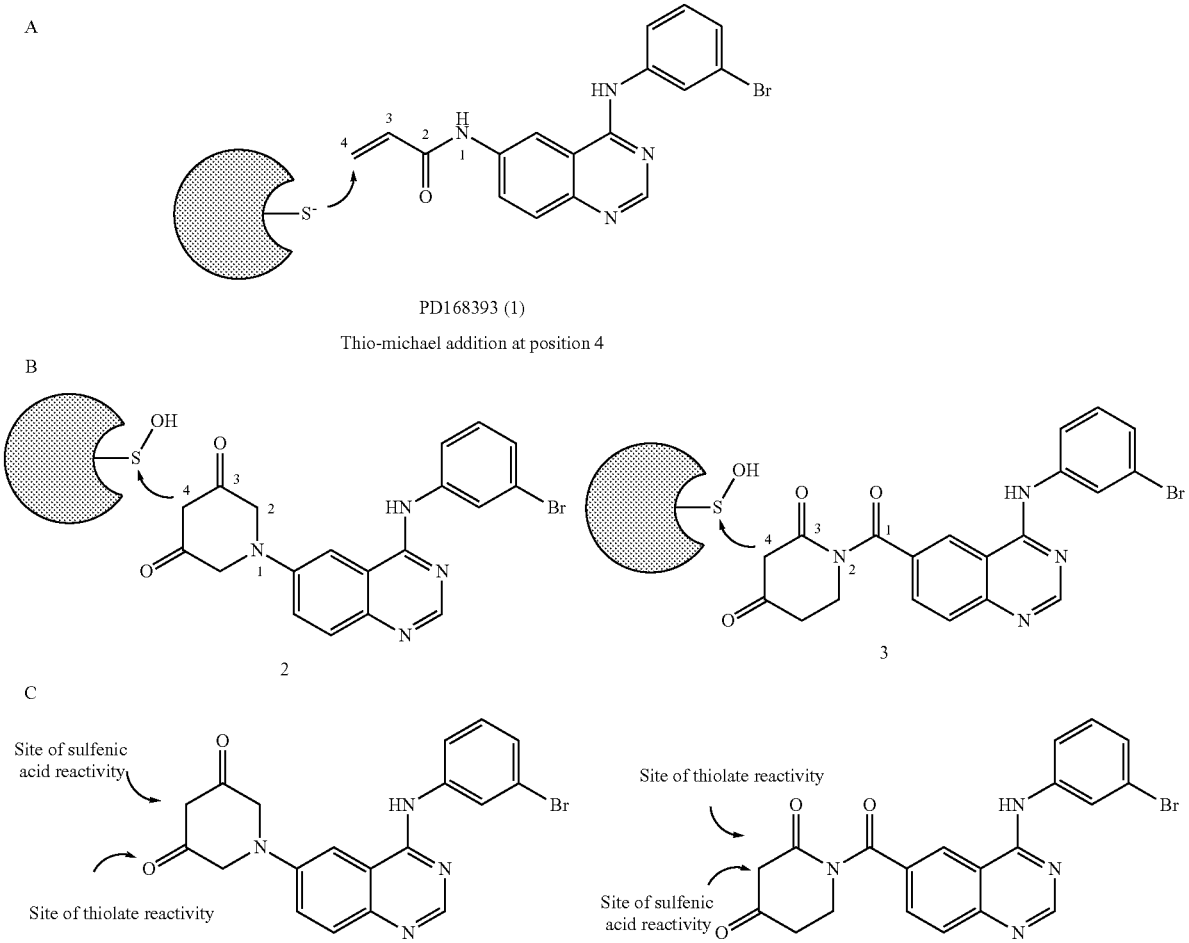

Exemplary redox-based EGFR inhibitors depicting Compounds 4a, 5a, 6a, 7a, 8a, and 9a based on the Afatinib core, may be found in FIG. 17. The six inhibitors bear sulfenic acid-specific warheads, which show maximum reactivity towards the dipeptide sulfenic acid model.

Figure 18C:
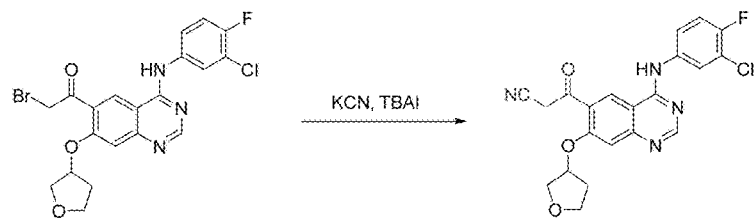

Proposed synthetic schemes for each inhibitor (Compounds 4a, 5a, 6a, 7a, 8a, and 9a) are detailed in FIG. 18 (A-C). Scheme 1 shows the synthesis of the core for amide-linked warhead attachment. Scheme 2 presents the synthesis of the core for direct warhead attachment. Scheme 3 demonstrates the synthesis of Compound 4a of FIG. 17. Scheme 4 presents the synthesis of Compound 5a of FIG. 17. Scheme 5 shows the synthesis of Compound 6a of FIG. 17. Scheme 6 demonstrates the synthesis for Compound 7a. Scheme 7 presents the synthesis of Compound 8a. Scheme 8 demonstrates the synthesis of Compound 9a (of FIG. 17).

Figure 19:
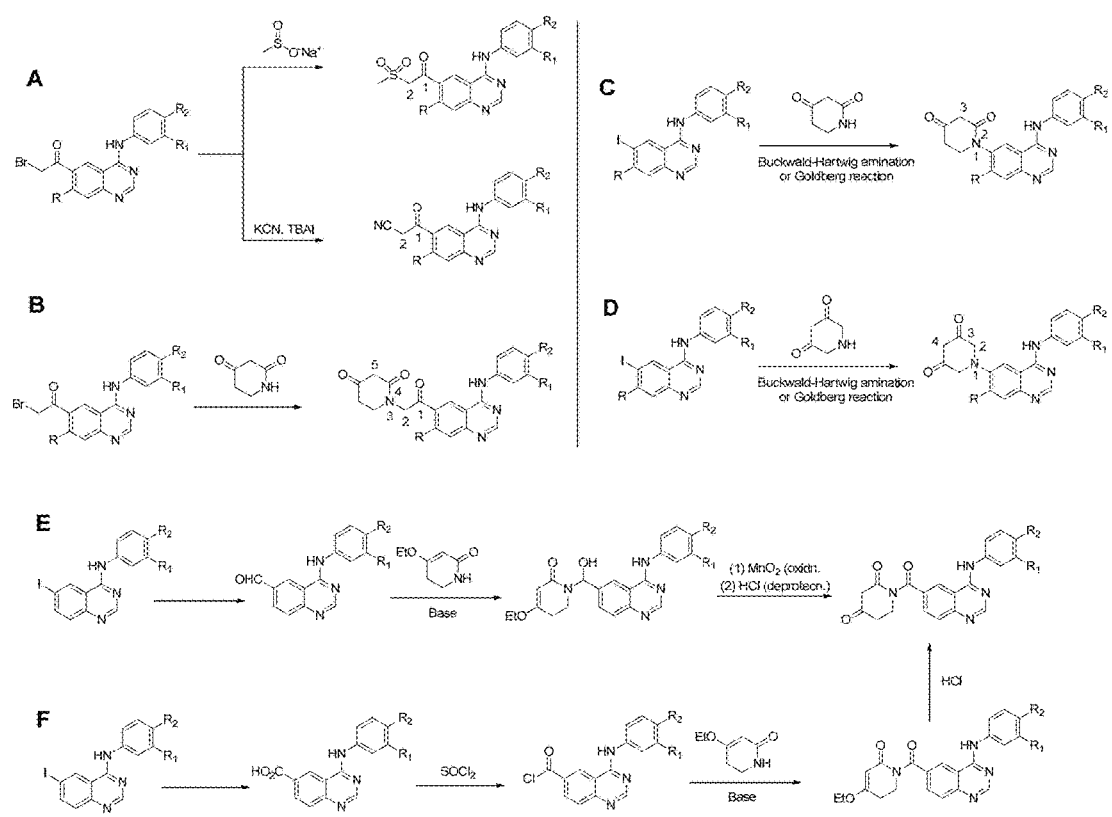
FIG. 19 depicts schemes for the syntheses of exemplary inhibitors through direct warhead attachment and variations of chain length.

Additional schemes for the syntheses of exemplary inhibitors may be found in FIG. 19. The syntheses utilize direct warhead attachment and study the variations of chain length.

PTP1B Target Protein

The invention also provides compounds comprising a nucleophilic warhead and binding element that modify the activity of PTP1B. PTP is a non-receptor phospho-tyrosine protein phosphatase. It negatively regulates insulin signaling by dephosphorylating the phosphotryosine residues of insulin receptor.

The foundation for PTP1B target protein probes was initiated by compounds containing a warhead, a binding module for YopH phosphatase, and a N3 reporter tag. The dissociation constants (Ki) may range from 2 µM to 12,000 µM. (Stephen E. Leonard, et al., "Redox-Based Probes for Protein Tyrosine Phosphatases," *Angew. Chem. Int. Ed.*, 2011, 50:4423-4427). Formula VI below represents a generic redox-based probe compound for YopH phosphatase that was the basis of the design strategy for the inventive RBI probes for tyrosine phosphatases:

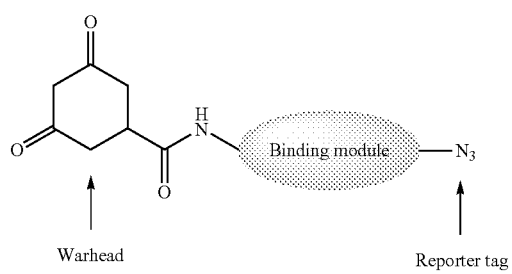

Some exemplary compounds and their inhibition constants include the following which do not make up the inventive compounds.

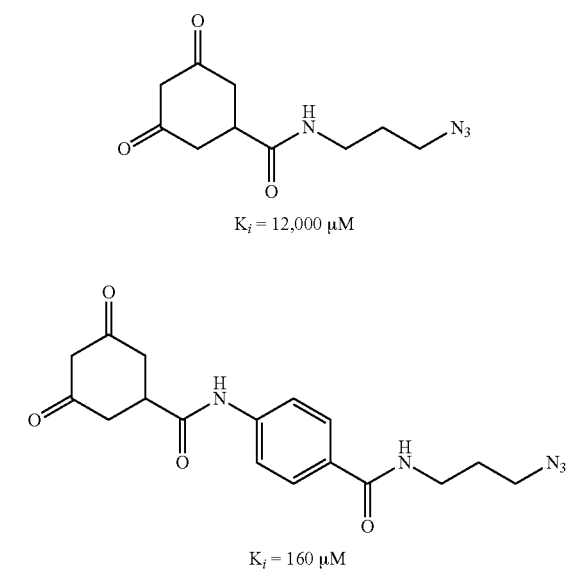

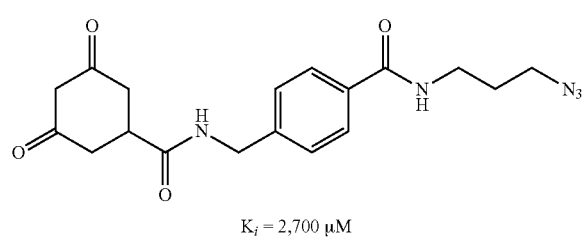

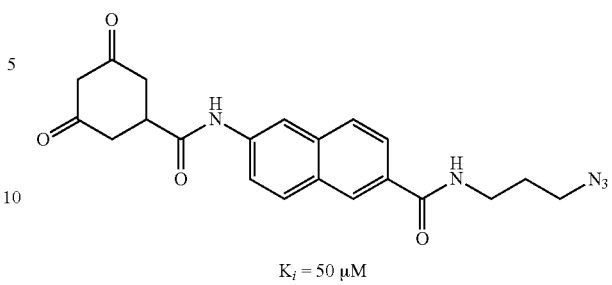

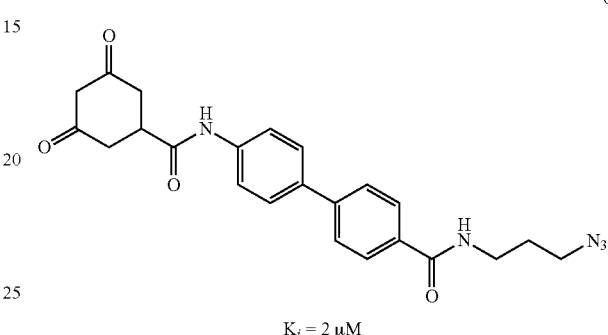

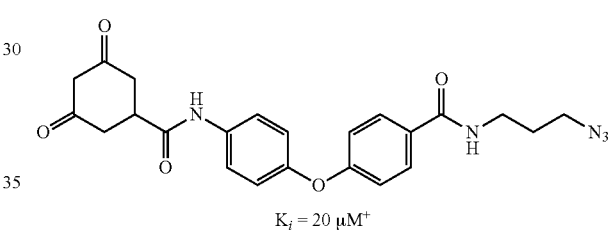

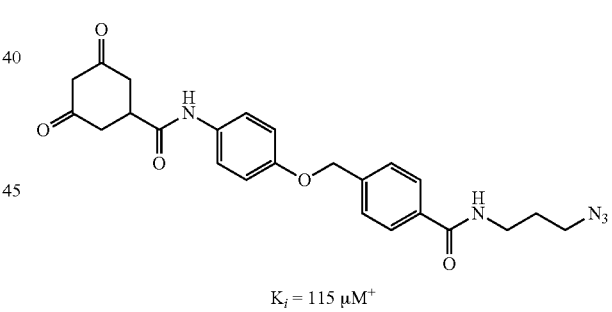

The exemplary foundation compounds, identified above, all have a $N_3$ reporter tag; whereas the inventive redox-based probes for tyrosine phosphatases all have a terminal alkyne. The primary difference is that the inventive RBI probe compounds with a terminal alkyne reporter tag showed in vitro enhancement over the $N_3$ reporter tag compounds. Alkyne tags depicted in Formula VII are less toxic then the azide analogs of Formula VI. Also, the bioorthongonal reaction is enhanced when the chemical reporter harbors an alkyne handle and is used in combination with an azide bearing detection tag. Thus, alkyne reporter tags and compounds with these reporters are preferred in one embodiment.

In certain embodiments, the compounds can be inhibitors of PTP1B. In further embodiments, the compounds of the invention inhibit the activity of PTP1B by covalently binding to PTP1B. In further embodiments, the compounds of the invention inhibit the activity of PTP by reversibly or irreversibly binding to PTP1B. In preferred embodiments, the compounds of the invention can be inhibitors of specific oxidized forms of PTP1B.

The inventive redox-based probes for tyrosine phosphatases which have the terminal alkyne reporter tag have the generic Formula VII compound:

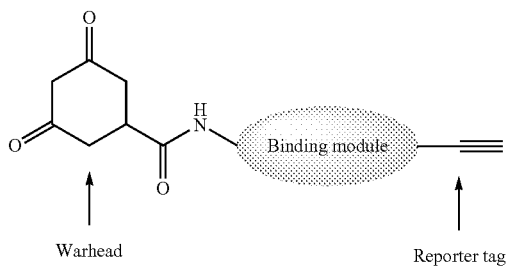

Warhead         Reporter tag where exemplary compounds include, but are not limited to the following:

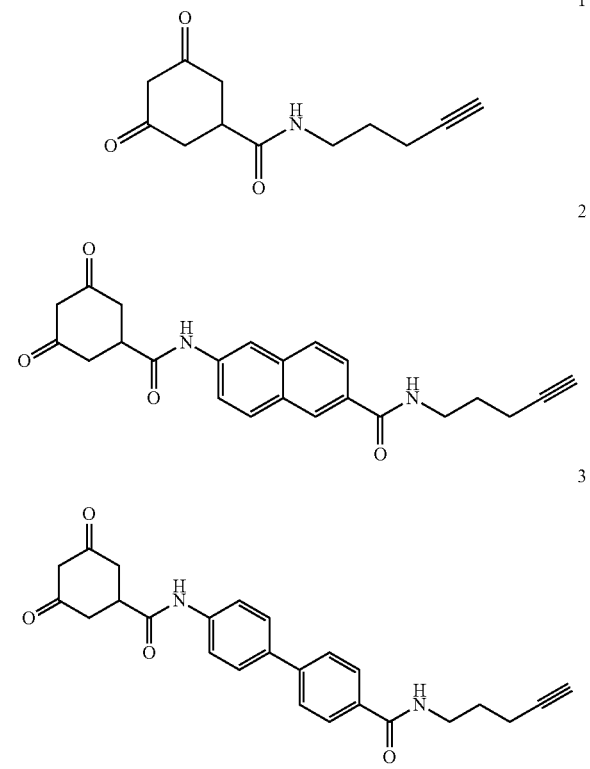

Figure 20:
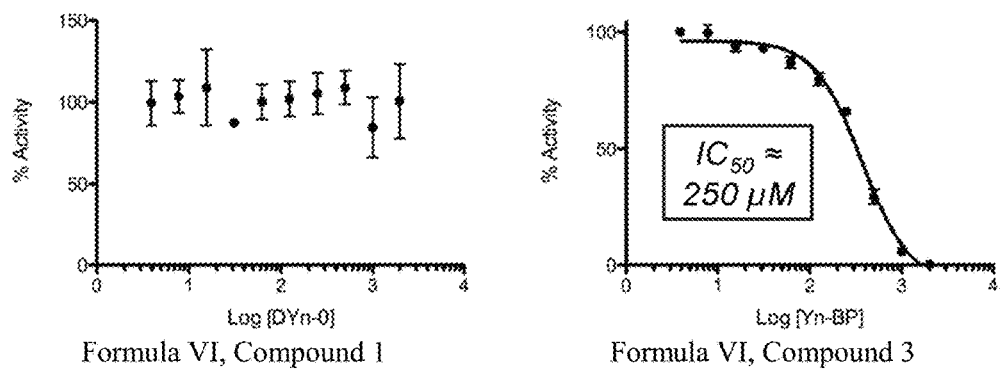
FIG. 20 depicts a fluorescence assay measuring the percent activity of probe compounds, DYn-0 and Yn-BP.
Figure 21A:
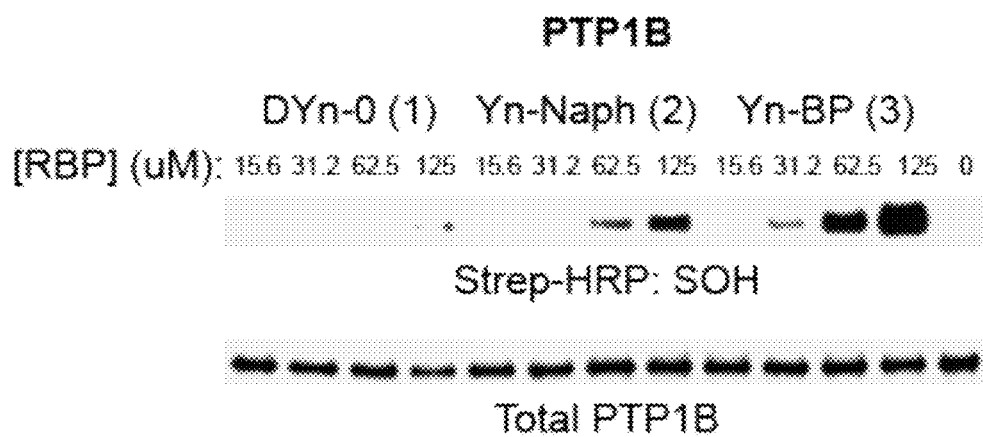
FIG. 21A-21C depict the in vitro studies with PTP1B and control proteins, GPX3 and GAPDH.
Figure 21B:
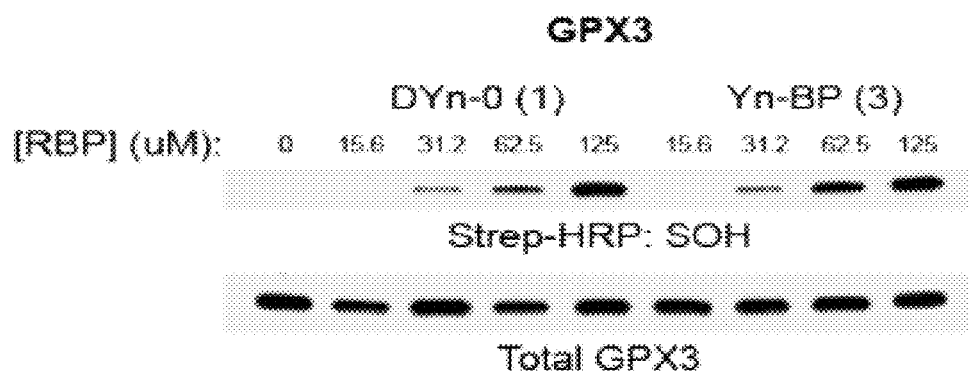
Figure 21C:
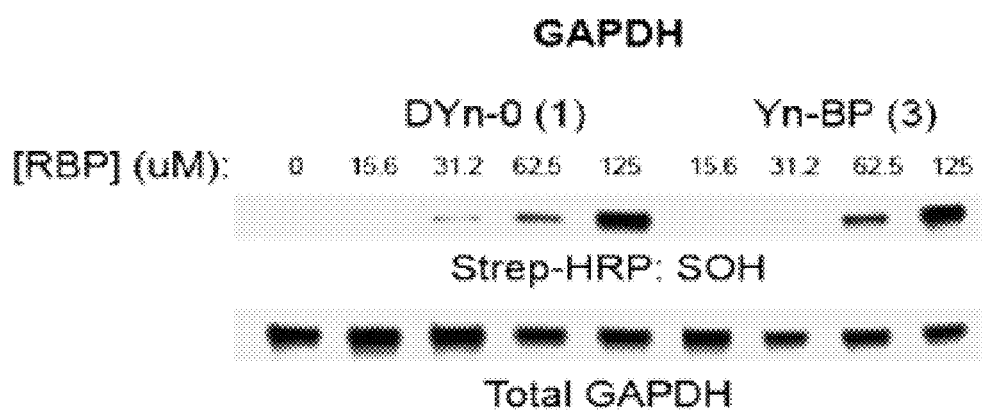

Further studies of Formula VII, Compound 1 (DYn-0) and Compound 3 (DYn-BP or Yn-BP) demonstrated that Compound 3 does not function as an aggregation-based inhibitor, which typically inhibit non-specifically (see, FIG. 20). DYn-BP or Compound 3 was shown to have an IC50 of approximately 250 µM. In vitro analyses with PTP1B and control proteins (i.e., GPX3 and GAPDH) demonstrated that Compound 2 (Yn-Naph) and Compound 3 showed preferential detection of oxidized PTP1B; whereas, there was no preferential detection of control proteins GPX3 and GAPDH (see, FIG. 21A). FIG. 21B and FIG. 21C demonstrated that Compound 1 and Compound 3 had no preferential detection of control proteins, GPX3 and GAPDH, respectively. Cell labeling western blot assays were performed using WT PJ3H-PTP1B purified from *E. coli* that was cloned into a mammalian expression plasmid. Recombinant PTP1B was expressed and purified from BL21AI cells. Recombinant proteins were labeled with respective equivalences of hydrogen peroxide (PTP1B, 10 eq; Gpx3 & GAPDH, 1.5 eq) in the presence of the indicated concentrations of sulfenic acid probes for 1 hour at room temperature with constant rocking Excess probe was removed by size-exclusion chromatography. Probe modified proteins were functionalized with a biotin reporter tag through the bioorthogonal Huisgen [3+2] Cycloaddition ("click chemistry") then analyzed by Western blot.

Figure 22:
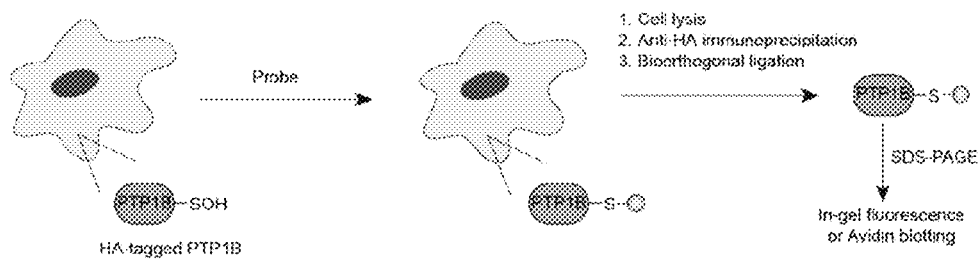
FIG. 22 depicts a method for detecting oxidized PTP1B in cells.
Figure 23:
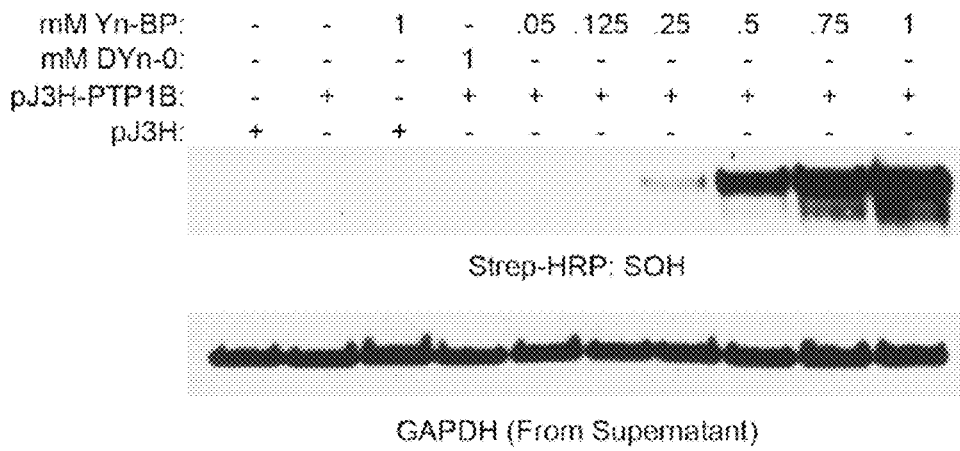
FIG. 23 depicts titration data of Yn-BP inhibitor in pJ3H-PTP1B transfected COS1 cells compared to DYn-0 probe.
Figure 24:
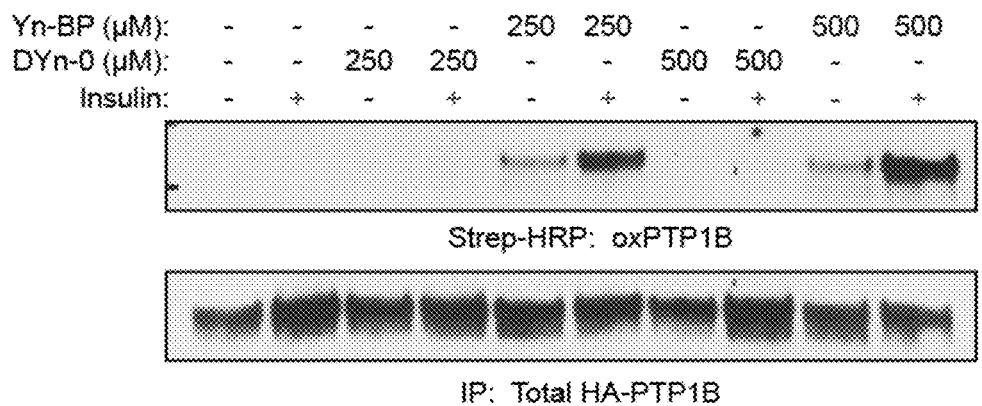
FIG. 24 depicts the detection of oxidized PTP1B in cells with insulin stimulation and Yn-BP redox-based probe and not with DYn-0.

A representation of the method for detecting oxidized PTP1B in cells (basal and insulin-stimulated) may be found in FIG. 22. The method was used in obtaining the titration data of Yn-BP redox-based proteins in pJ3H-PTP1B transfected COS1 cells compared to DYn-0 probe of FIG. 23. Forty-eight (48) hours post pJ3H-PTP1B chemical transfection, cells were washed with PBS and lifted with 0.25% trypsin-EDTA. The cells were suspended in serum-free DMEM at a density of about $3\times10^6$ cells/mL to about $4\times10^6$ cells/mL and treated with DMSO or the indicated concentration of the redox-based probes for 1 hour at 37° C. in a 5% $CO_2$ humidified atmosphere. Detection of oxidized PTP1B in the cells was demonstrated with insulin stimulation and Yn-BP, but not with DYn-0 alone. (see, FIG. 24).

For insulin treatment, cells were cultured in a similar fashion with the exception of being serum-starved 16 hours prior to the experiment. Cells were stimulated with 100 nM insulin for 2 minutes followed by the addition of the redox-based probes for 1 hour at 37° C. in a 5% $CO_2$ humidified atmosphere. HA-PTP1B was immunoprecipitated with anti-HA agarose and probe modified PTP1B was visualized by addition of a reporter tag via click chemistry followed by Western blot. Essentially, the generic compound of Formula VII was shown to enhance affinity to oxidized PTP1B both in vitro and ex vivo.

Non-limiting additional compounds and derivatives based on Formula VIII are exemplified below:

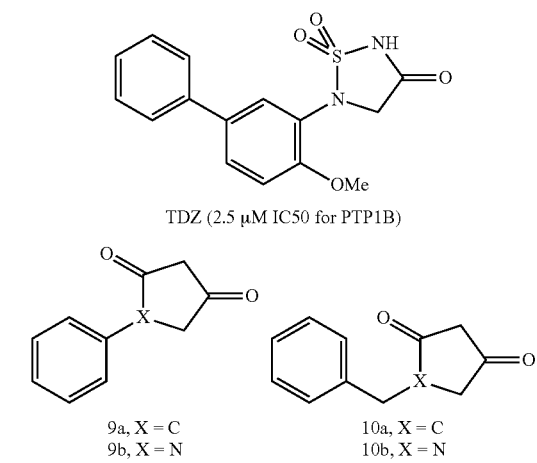

TDZ (2.5 µM IC50 for PTP1B)

9a, X = C
9b, X = N

10a, X = C
10b, X = N

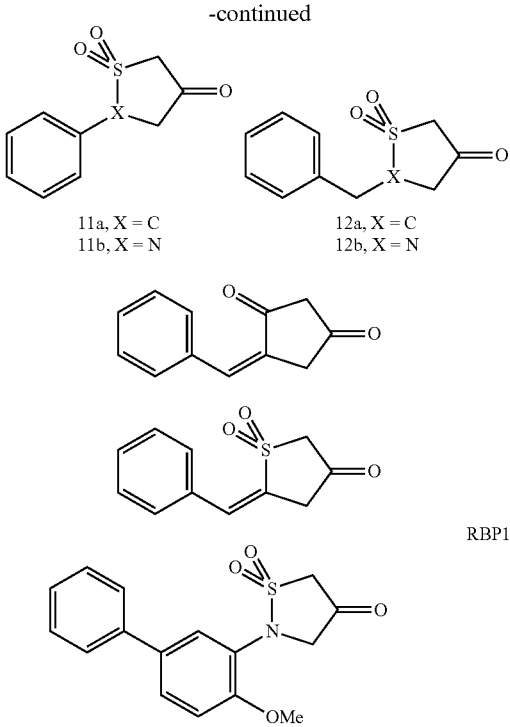

11a, X = C
11b, X = N

12a, X = C
12b, X = N

13

RBP1 (15)

Compounds TDZ and RBP1 may be preferred PTP inhibitors. TDZ mimics known difluoromethylphosphonate (DFMP) and carbosymethylsalicyclic acid (CMS) inhibitors. The TDZ heterocycle may offer improved permeability due to decreased charge density and enhanced selectivity for the catalytic site of PTPs by capitalizing on important hydrogen bonds from the carbonyl and sulfonamide groups. RBP1 maintains these important functional groups and interactions with the exception of harboring a nucleophilic center which can chemoselectively react with oxidized cysteine residues.

A particular embodiment of a compound that modifies the activity of PTP is a compound of Formula IX:

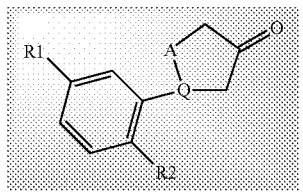

wherein:
A is any atom or functional group that promotes binding to PTP1B, i.e., a binding element or module. In some embodiments, A is a carbonyl group (C=O) or sulfonyl group (O=S=O).
Q is a carbon atom or a nitrogen atom.
R1 is a hydrogen atom or any straight, branched, and/or cyclic alkyl functional group. In certain embodiments, R1 may include more than one functional group. In further embodiments, R1 includes, but is not limited to, any straight, branched, and/or cyclic alkyl functional group containing 0-20 carbon atoms (C0-C20). In further embodiments, R1 includes, but is not limited to, cyclic benzene groups.
R2 is a hydrogen atom or any straight, branched, cyclic alkyl functional group, or any combinations of straight, branched, a cyclic alkyl functional groups. In certain embodiments, R2 may include more than one functional group. In further embodiments, R2 includes, but is not limited to, any straight, branched, cyclic alkyl functional group, or combinations thereof, containing 0-20 carbon atoms.

In one specific embodiment, a compound that modifies the activity of PTP1B has the following Formula X:

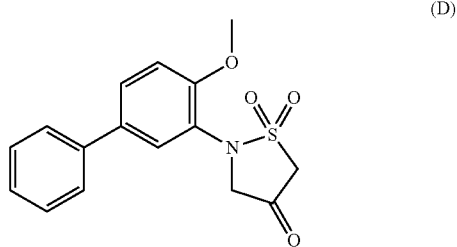 [SMILES: COc1ccc(-c2ccccc2)cc1N1CC(=O)CS1(=O)=O]

(D)

Compound D (or TDZ-7), described above, is an example of an inhibitor of PTP1B.

A further particular embodiment of a compound that modifies the activity of PTP is a compound of Formula XI:

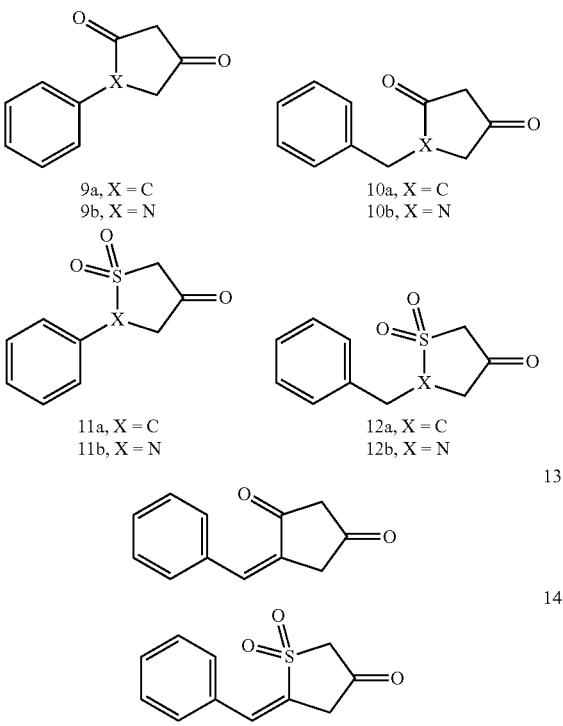

9a, X = C
9b, X = N

10a, X = C
10b, X = N

11a, X = C
11b, X = N

12a, X = C
12b, X = N

13

14

A is any atom or functional group that promotes binding to PTP1B. In some embodiments, A is a carbonyl group (C=O) or sulfonyl group (O=S=O);
Q is a carbon atom or a nitrogen atom;
a is either a single bond or double bond; and
n is either 0 or 1.

The following compounds are additional examples of PTP1B inhibitors:

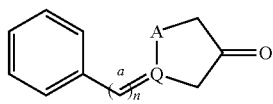

Compounds 9b and 10b demonstrated adduct formation with oxidized PTP1B. Whereas, the other compounds were reactive in dipeptide sulfenic acid models although not with oxidized PTP1B.

Further, studies demonstrate that compounds of the invention are capable of binding to the oxidized form of PTP1B. For example, experimental results, depicted in FIG. 25, have demonstrated that the Compound with the nucleophilic warhead (DYn) and binding element or module (BP), described above, covalently binds to the oxidized form of PTP1B in a dose-dependent manner.

The invention also includes methods of synthesizing compounds that modify the activity of PTP1B. For example, FIG. 26 describes a method that is predicted to be useful for synthesizing Compound D (TDZ-7). Scheme 1 describes an overall method for synthesizing Compound D. Scheme 2 describes a method for synthesizing the compound referred to in Scheme 1 as Compound 3.

In addition, FIG. 27 displays methods for synthesizing Compounds 9b, 10a, and 10b, pictured above. Scheme 1 depicts a method for synthesizing Compound 9b. Scheme 2 depicts a method for synthesizing Compound 10a. Scheme 3 depicts a method for synthesizing Compound 10b.

FIG. 28 demonstrates the effect of an inhibitor compound (RBI) on insulin receptor (IR-β) phosphorylation (pIR-β). The Redox-Based Inhibitor is TDZ-2BP or TDZ-4BP presented in increasing concentrations. The data for each RBI are from two independent experiments in Chinese Hamster Ovary (CHO) cells expressing insulin receptor. The inhibitor concentrations are 0 mM (depicted by "-") and under the triangle, each of the lanes have an inhibitor concentration of 0.03125 mM, 0.0625 mM, 0.125 mM, 0.25 mM, 0.5 mM, and 1 mM. The concentration of insulin is 10 nM, vanadate is 1 mM, and a 4G10 primary antibody was used to detect pIR-β in the Western blot.

Briefly, CHO/hIRc cells were plated onto 6-well pates and allowed to become adherent in complete media overnight at 37° C. in a humidified atmosphere of 5% $CO_2$. The cells were serum-starved for 16 hours prior to the experiment. CHO/hIRc cells were pre-treated with DMSO, 1 mM vanadate, and DYn-0 or BP-Yn1 at various concentrations for 1 hour at 37° C., 5% $CO_2$. Media containing DMSO, vanadate, or RBPs was removed and the cells were washed with PBS (3×) then stimulated with 10 nM insulin for 5 minutes. After stimulation, the media was removed and the cells were washed with ice cold PBS (3×). The cells were then lysed with the aid of a rubber policeman. The lysate was resolved by SDS-PAGE and analyzed by Western blot.

The data of FIG. 28 demonstrates a trend of an increase in phosphorylation at lower concentrations of inhibitor (which is expected if the inhibitor targets PTP1B); whereas, higher concentrations of inhibitor begin to block dephosphorylation. One possible interpretation of these data may be that these inhibitors begin to target other proteins, such as kinases, at higher concentrations and that the PTP relevant effect is observed at the lower concentrations. Also, at the highest concentrations, the triphasic behavior of TDZ-4BP may be explained through toxicity and/or stimulation of survival phosphorylation signaling pathways. However, FIG. 29 essentially demonstrates that the inhibitors do modulate insulin receptor phosphorylation levels.

Figure 30:
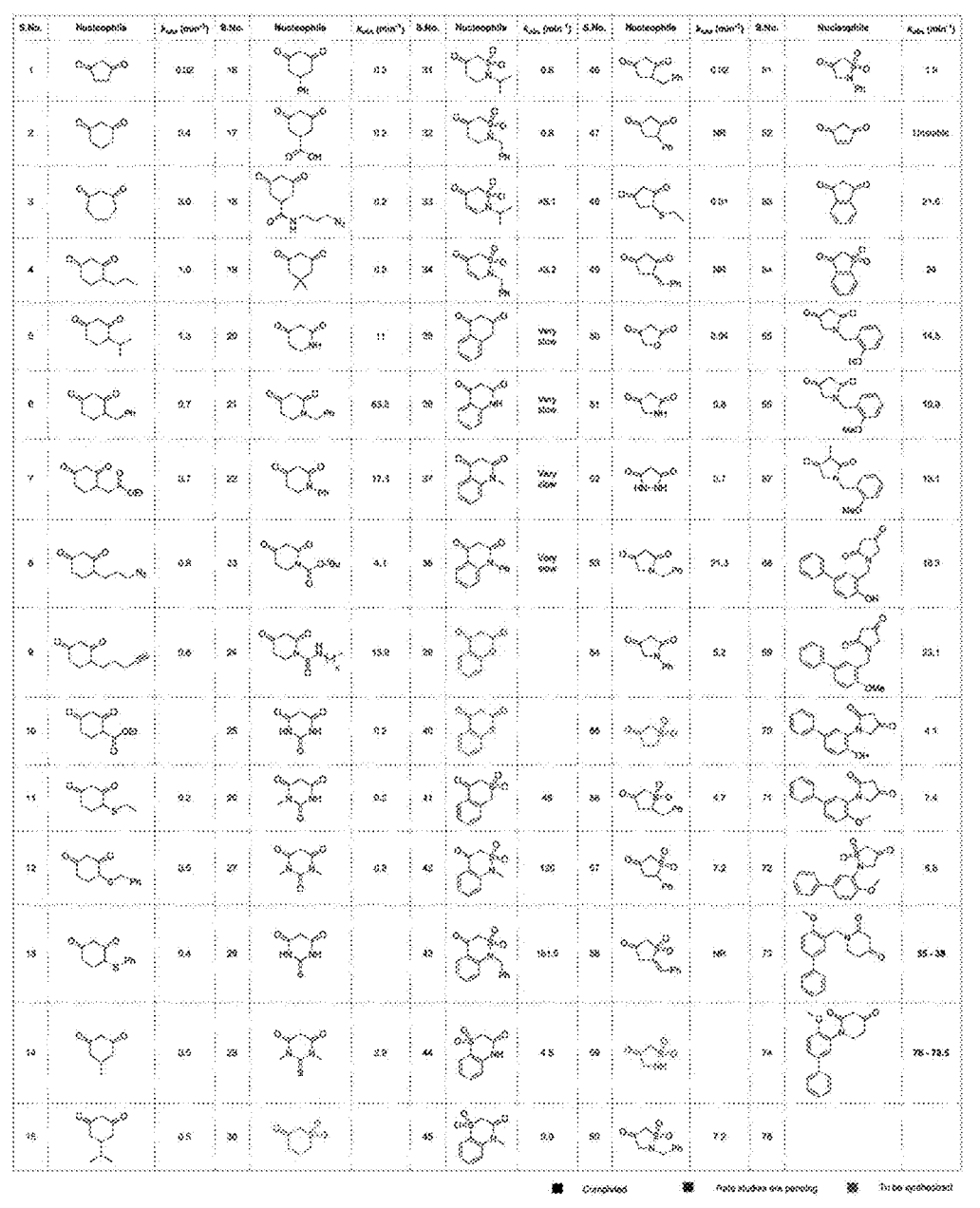

Exemplary irreversible sulfenic acid nucleophiles that are useful in the compounds comprising at least a nucleophilic warhead and a binding element may be found in FIG. 29, FIG. 30, and FIG. 31. FIG. 30 and FIG. 31 provide the observed rate constant ($min^{-1}$) or pseudo first-order rate constant which varies with the concentration of the nucleophile. Preferred nucleophiles may be selected based on those having a high pseudo 1st order rate constant for reaction in the dipeptide sulfenic acid model system. For example, the rate constant for reaction of dimedone in the dipeptide model is 1 $min^{-1}$. However, it is not reactive enough to trap the sulfenic acid in PTP1B as an observable adduct by intact mass analysis. Preferred nucleophiles for the PTP1B target will have a reaction rate constant at least an order of magnitude greater than 1 $min^{-1}$ (i.e., greater than 10 $min^{-1}$). The faster the rate constant for reaction of the nucleophile with sulfenic acid, the more oxidized PTP1B will be covalently modified and irreversibly inhibited by the nucleophile warhead.

Applications—Methods of Treating/Preventing Diseases

The compounds of the invention that modify the activity of a target protein such as EGFR or PTP1B may be used in methods of treating, preventing, or minimizing disease or disease symptoms in a subject, preferably a mammal, and more preferably a human. Generally, the method comprises treating, preventing, or attenuating a disease or disease symptoms by administering a compound to the subject that modifies the activity of the target protein, e.g., EGFR or PTP1B. In a preferred embodiment, a therapeutically effective amount of the compound is administered to the subject. In certain embodiments, the subject is an animal, preferably the animal is a mammal, and more preferably, the mammal is a human. In a further preferred embodiment, the administered compound covalently binds to EGFR and inhibits the activity of EGFR or covalently binds PTP and inhibits the activity of PTP1B. In a further preferred embodiment, the compound binds to the sulfenylated form of EGFR and inhibits the activity of the sulfenylated form of EGFR or the compound binds to a specific oxidized form of PTP1B. In a further preferred embodiment, the EGFR inhibitor compounds are administered to the animal to treat or prevent cancer. The types of cancer that may be treated, prevented, or alleviated by administering the compounds of the invention include, but are not limited to, lung cancer, anal cancer, and glioblastoma multiforme. In further embodiments, the compounds are administered parenterally (e.g., intravenous, subcutaneous, intraperitoneal injection, etc.) in any suitable amount (from about 0.001 mg/kg, 0.01 mg/kg, 0.1 mg/kg or 0.3 mg/kg; to about 0.3 mg/kg, 0.5 mg/kg, 1.0 mg/kg, or 10.0 mg/kg, or more) to treat, prevent, or attenuate cancer in the animal. Another preferred embodiment may be directed to administration of the PTP1B inhibitor compounds to the treat, prevent, or attenuate the animal suffering from diabetes, e.g., type 2 diabetes. The PTP1B inhibitor compounds may be administered to an animal suffering from diabetes in any suitable amount (from greater than about 0.001 mg/kg, about 0.01 mg/kg, about 0.1 mg/kg, or about 0.3 mg/kg; to less than about 0.3 mg/kg, about 0.5 mg/kg, about 1.0 mg/kg, or about 10.0 mg/kg, or less than an amount greater than 10 mg/kg) to treat, prevent, or minimize diabetes or its symptoms in the animal.

Applications—Pharmaceutical Formulations with Active Compounds

The compounds of the invention, comprising a nucleophilic warhead and binding element, can be used as active ingredients in pharmaceutical formulations. In certain embodiments, the pharmaceutically acceptable salts of the inventive compounds may be used as active ingredients in pharmaceutical formulations. Pharmaceutically acceptable salts are salts that retain the desired biological activity of the parent compound and do not have some or all of the undesired toxicological effects. Examples of such salts are (1) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (2) salts formed from elemental anions such as chlorine, bromine, and iodine. In preferred embodiments, the pharmaceutical formulations contain therapeutically or pharmaceutically effective amounts of the active ingredients or their pharmaceutically acceptable salts.

The compounds of the invention are useful as pharmaceutically active ingredients and may be utilized in bulk form. Preferably, these compounds are formulated into pharmaceutical formulations for administration to a subject. A subject can be any animal, including mammals and, more preferably, humans. Any of a number of suitable pharmaceutical formulations may be utilized as a vehicle for the administration of the compounds of the invention.

The compounds of the invention may be formulated for administration for the treatment, prevention, or minimization of a variety of conditions and diseases. In the manufacture of a pharmaceutical formulation according to the invention, the compounds of the invention and their pharmaceutically acceptable salts, or the acid derivatives of either (hereinafter referred to as the "active compound") are typically admixed with, inter alia, an acceptable carrier. The carrier must be compatible with other ingredients in the formulation and must not be deleterious to the patient. The carrier may be a solid or a liquid, or both, and is preferably formulated with the compound as a unit-dose formulation, for example, a tablet, which may contain from about 0.5% to about 95% by weight of the active compound. One or more of each of the active compounds may be incorporated in the formulations of the invention, which may be prepared by any of the well-known techniques of pharmacy comprising admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous), and transdermal administration, although the most suitable route in any given case will depend on the nature and severity of the condition or disease being treated, prevented, or minimized, and on the nature of the particular active compound which is being used.

Formulations suitable for oral administration include, but are not limited to, capsules, cachets, lozenges, or tablets, each containing a predetermined amount of the active compound; as a powder or granules; as a solution or a suspension in an aqueous or non-aqueous liquid; or as an oil-in-water or water-in-oil emulsion. The formulations may be prepared by any method that includes the step of bringing into association the active compound and a suitable carrier (which may contain one or more additional ingredients as noted above).

In general, the formulations of the invention are prepared by uniformly admixing the active compound with a liquid or finely divided solid carrier, or both, and then, if needed, shaping the resulting mixture. For example, tablets can be prepared by compressing or molding powder or granules containing the active compound, optionally with one or more additional ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for sub-lingual administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous preparations of the active compound, and the preparations are preferably isotonic with the blood of the subject. These parenteral formulations may be administered by means of subcutaneous, intravenous, intramuscular, or intradermal injection. The preparations may be prepared by admixing the compound with water or a glycine buffer and rendering the resulting solution sterile and isotonic with the blood.

Formulations suitable for topical application to the skin preferably take the form of an ointment, cream, lotion, paste, gel, spray, aerosol, or oil. Carriers that may be used include vaseline, lanoline, polyethylene glycols, alcohols, transdermal enhancers, and combinations of two or more thereof.

Formulations suitable for transdermal administration may be presented in patches adapted to remain in contact with the epidermis of the recipient for a prolonged period of time. Formulations suitable for transdermal administration may also be delivered by iontophoresis and typically take the form of a buffered aqueous solution of the active compound, although it is not required that the solution be buffered. Suitable formulations comprise citrate or bis/tris buffer (pH 6) or ethanol/water and contain from about 0.01 M to about 0.2M active compound.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

Having now fully described the subject compositions and methods, it will be understood by those of ordinary skill in the art that the same can be performed within a wide and equivalent range of conditions, formulations and other parameters without affecting their scope or any embodiment thereof. All cited patents, patent applications, publications, and documents are fully incorporated by reference in their entirety.

EXAMPLES

Example 1

Synthesis of Probe Compound, DYn-0, and Inhibition Studies

The DYn-0 compound (FIG. 6A) may be synthesized by the following method. To a dry round bottom flask with nitrogen was added 3-methoxy-5-oxocyclohex-3-9-enecarboxylic acid (300 mg, 1.76 mmol), EDC-HCl (505.9 mg, 2.65 mmol), and dry DMF (2 mL). The reaction was allowed to mix at room temperature for 30 min under nitrogen. 4-pentyneamine (293.1 mg, 3.53 mmol) was added and the reaction mixture was brought up to 75° C. and allowed to mix overnight under nitrogen. The reaction was quenched with addition of water and extracted with EtOAc. The organic layer was dried over MgSO4, filtered, and concentrated. The crude material was not subjected to flash column chromatography resulting in a yield of 329.2 mg of DYn-0 product (79% yield).

Figure 32:
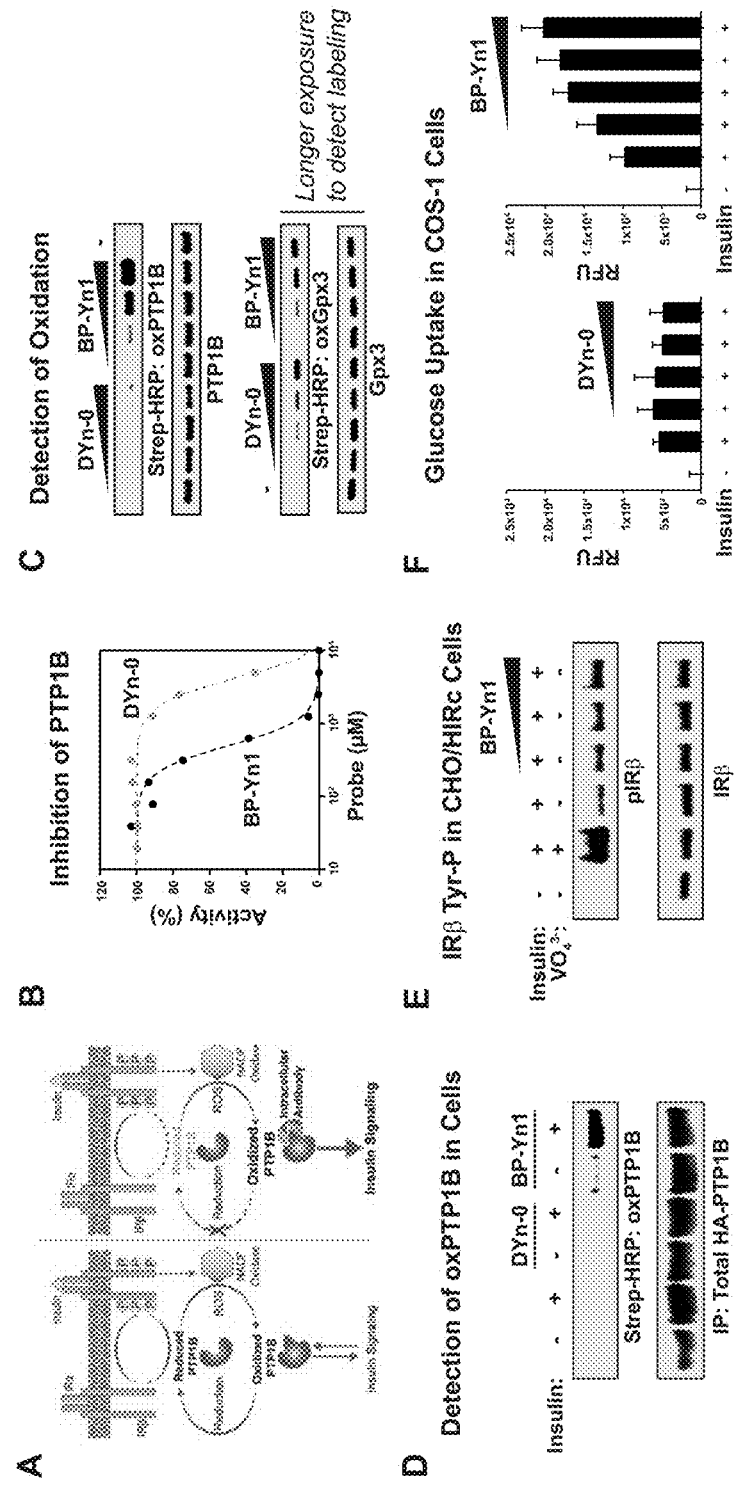
FIG. 32 depicts the targeting of oxidized PTP1B during insulin signaling—the receptor-ligand interaction (A); inhibition of PTP1B (B); detection of oxidation (C); detection of oxidized PTP1B in cells (D); IRβ tyrosine phosphorylation in CHO/HIRc cells (E); and glucose uptake in COS-1 cells comparing probes DYn-0 and BP-Yn1 (F).
Figure 33:
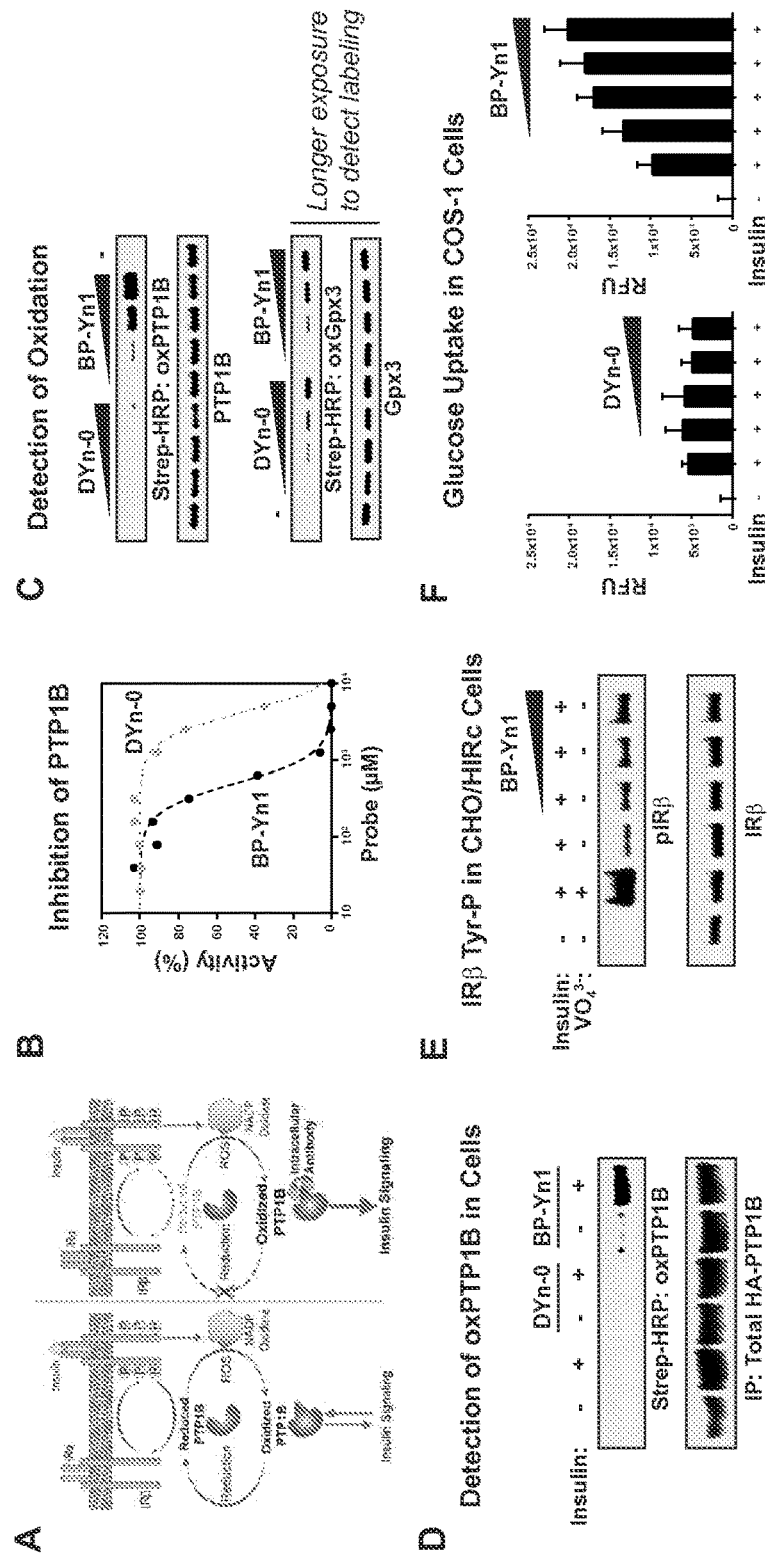

The inhibition of PTP1B was studied using the probe DYn-0 and BP-Yn1. Insulin binding to Insulin Receptor-β (IRβ) induces receptor autophosphorylation on specific tyrosine residues within the cytoplasmic domain. The newly phosphorylated (P) sites serve as interaction platforms for proteins involved in key prosurvival pathways. Receptor-ligand interaction also stimulates the production of ROS and oxidation of intracellular biomolecules, leading to modulation of the signaling cascade (FIG. 32A). The percent phosphatase activity was reduced by an order of magnitude in the concentration of DYn-0 to BP-Yn1 (FIG. 32B). Detection of oxidized PTP1B or oxidized control protein, Gpx3 in the presence of probe compounds, DYn-0 and BP-Yn1 (FIG. 32C). Detection of oxidized PTP1B in COS1 cells upon insulin stimulation (FIG. 32D). Dose-dependent phosphorylation of IRβ tyrosine phosphatase in the presence of insulin with BP-Yn1 in CHO/HIRc cells (FIG. 32E). Glucose uptake in COS-1 cells with increasing amounts of BP-Yn1 (FIG. 32F).

The PTP assay included PTP that was prepared up to 100 nM in 32 mM HEPES, pH 7.2, 5 mM NaCl, 2.5 mM EDTA, 0.83% glycerol, 0.02% Triton X-100, and 0.002% Brij-35. The protein was dispensed to a black ckear-bottomed 96-well microplate followed by the addition of redox-based probes or DMSO and allowed to incubate for 15 minutes at 25° C. The assay was initiated with the addition of 4-methylumbelliferyl phosphate (4-MUP), and the formation of fluorescent product was measured with an excitation wavelength of 358 nm and emission wavelength of 449 nm.

For the Glucose Uptake assay, COS-1 cells were plated in triplicate in a black clear-bottomed 96-well microplate at a density of about 3×10$^4$ cells/well and allowed to become adherent in complete media overnight at 37° C. in a humidified atmosphere of 5% $CO_2$. Subsequently, the cells were washed with PBS and serum starved in glucose-free DMEM for 4 hours at 37° C., 5% $CO_2$. Following serum deprivation, the cells were treated with varying concentrations of redox-based probes for 1 hour at 37° C., 5% $CO_2$. Media containing probes was removed, and the cells were treated with 2-NBD glucose in the presence of 250 nM insulin for 15 minutes at 37° C., 5% $CO_2$. After stimulation, cells were washed, and 2-NBD glucose uptake was measured using an EnVision® plate reader with an excitation wavelength of 485 nm and emission wavelength of 535 nm.

It was demonstrated that stabilization of oxidized PTP1B using single-chain variable fragment antibodies, which target a unique conformation of oxidized PTP1B, enhanced phosphorylation and sustained insulin signaling (FIG. 32A). The redox-based probes, which harbor a binding module, showed enhanced selectivity for phosphatases (FIG. 32B) and detected the oxidized phosphatase as opposed to the parent compound with no binding module (FIG. 32C). Cell studies showed that the BP-Yn1 probe could detect increased levels of oxidized PTP1B upon insulin stimulation (FIG. 32D). This translated to small molecule trapping of the oxidized phosphatase and enhancement of insulin receptor phosphorylation (FIG. 32E) and glucose uptake (FIG. 32F). These findings support the development of the new class of small molecule inhibitors that target the oxidized inactive phosphatase by nucleophilic trapping of the oxidized catalytic cysteine as presented here.

Example 2

Synthesis of Probe Compound, DYn-1

The DYn-1 compound (FIG. 5) may be synthesized by the following method. To a solution of 3-ethoxy-6-(prop-2-yn-1-yl)cyclohex-2-enone (0.05 g, 0.29 mmol) in acetonitrile (2 ml) and water (2 ml) was added CAN (0.015 g, 0.028 mmol). The solution was heated to reflux for 2 hr. The reaction mixture was then diluted with brine (20 ml), and extracted with EtOAc (3×20 ml). The organic phases were combined, washed with brine (30 ml), dried over Na2SO4, and concentrated in vacuo. The resulting orange solid was purified by silica gel column chromatography using 1:1 Hexanes:EtOAc to give compound 1 as a pale yellow solid (0.042 g, 0.28 mmol) in 96% yield. Rf: 0.3 (1:1 Hexanes:EtOAc).

Example 3

Synthesis of Probe Compound, DYn-2

The DYn-2 compound of Formula XII (FIG. 5):

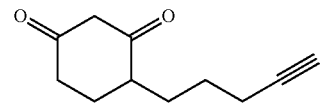

Figure 5:
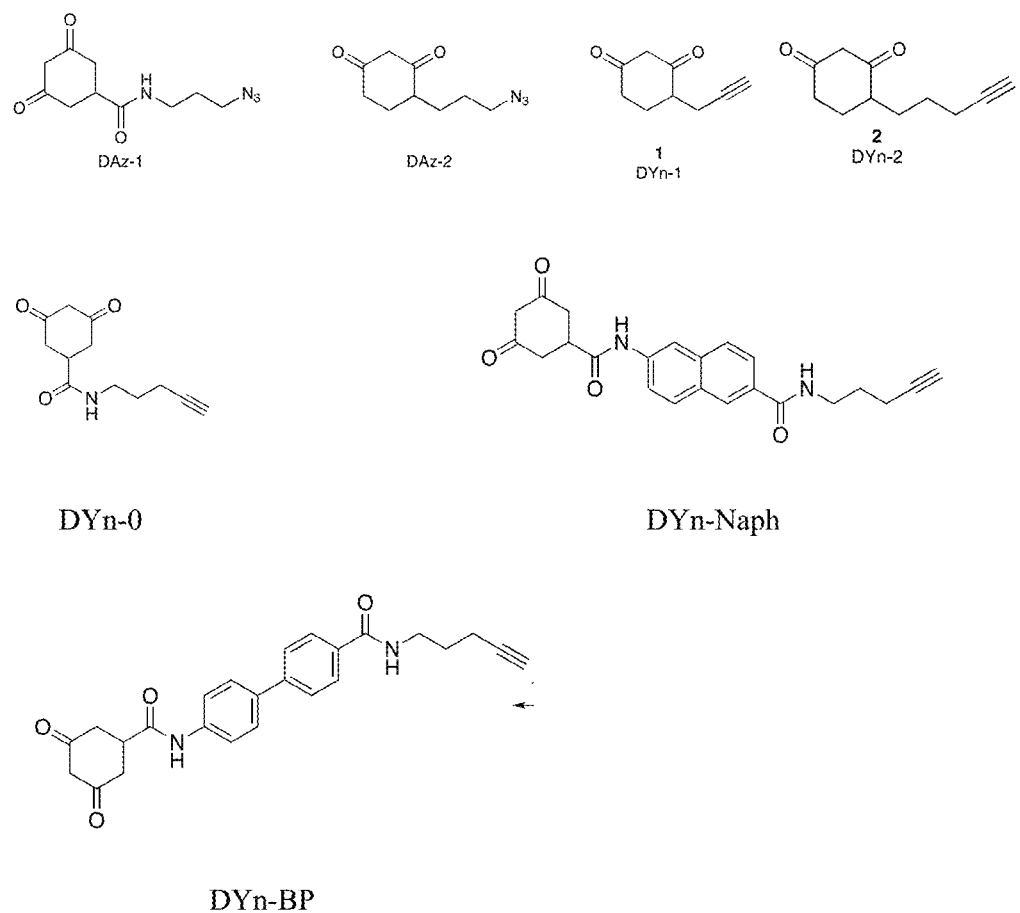
FIG. 5 depicts examples of probe compounds useful for identifying proteins with at least one redox-sensitive cysteine.

FIG. 5 may be synthesized by the following method from Jackson, P. M.; Moody, C. J.; and Shah, P. *Journal of the Chemical Society, Perkin Transactions 1: Organic and Bio-Organic Chemistry* (1972-1999), (11), 2909-18, 1990 (FIG. 6B, Scheme 4). All reactions were conducted in flame-dried glassware under an argon atmosphere with dry solvents, unless otherwise noted. Tetrahydrofuran (THF) was freshly distilled from sodium/benzophenone. All chemicals were purchased from Sigma-Aldrich (St. Louis, Mo.) and used as received. Silica gel P60 (Sorbent Technologies) was used for column chromatography. Reactions were monitored by thin layer chromatography (TLC) carried out using Analtech 60 F254 silica gel (precoated sheets, 0.25 mm thick). 5-iodo-pent-1-yne was synthesized according to the reported procedure. $^1$H NMR and $^{13}$C NMR spectra were collected in CDCl3 (Cambridge Isotope Laboratories, Cambridge, Mass.) at 400 and 100 MHz using a Bruker AM-400 instrument with chemical shifts relative to residual $CHCl_3$ (7.27 and 77.37 ppm). Low resolution mass spectral analyses were carried out on an Agilent LC/MS system.

Lithium diisopropylaminde was prepared by the dropwise addition of 2.5 M solution of n-BuLi (15.7 ml, 39.25 mmol) to a solution of diisopropylamine (3.97 g, 39.25 mmol) in THF (40 ml) and stirring the resultant pale yellow mixture at −78° C. for 30 minutes in 250 ml flask equipped with stir bar under N2 pressure. A solution of cyclohexane-1,3-dione (2.0 g, 17.84 mmol) in THF (20 ml) and HMPA (10 ml) was added dropwise to this lithium diisopropylamide solution at −78° C. Resulting deep yellow colored reaction mixture was allowed to stir at −78° C. and the temperature was slowly increased to 0° C. The reaction mixture was allowed to stir at 0° C. for 30 minutes after which it was again cooled to −78° C. To this dianion slurry, a solution of 5-iodopent-1-yne (3.81 g, 19.62 mmol) in THF (20 ml) was added dropwise at −78° C. Resulting orange slurry was stirred at −78° C. for 2 h with close monitoring. After the completion, the reaction mixture was neutralized with 1.0 M HCl. THF was removed under reduced pressure and the residue was partitioned between ethyl acetate and water. Organic layer was separated and aqueous layer was extracted with ethyl acetate (3×75 ml). Organic layers were combined and washed brine, dried over anhydrous magnesium sulfate, filtered and evaporated to give crude product. The product was purified by column chromatography using a gradient of 100% DCM which was increased up to 2% MeOH in DCM to recover the product (3.0 g, 16.83 mmol) as a mixture of keto and enol form in 94% isolated yield. $^1$H-NMR (400 MHz, CDCl$_3$): δ 5.42 (s, 1H), 3.41 (d, J=4.0 Hz, 2H), 2.75-1.72 (m, 16H), 1.68-1.45 (m, 6H); 13C-NMR (100 MHz, CDCl3): δ 204.9, 204.4, 197.0, 189.2, 104.2, 84.4, 84.1, 69.1, 68.9, 58.5, 49.1, 41.8, 39.9, 30.1, 29.6, 28.5, 26.4, 26.2, 26.1, 24.7, 18.8, 18.7; LC-MS: m/z for $C_{11}H_{14}O_2$ calculated: 178.23; observed: 179.1 (M$^+$+1, 100%).

Example 4

Synthesis of Probe Compound, DYn-Naph

The DYn-Naph compound (FIG. 5) may be synthesized by the following method (FIG. 6A, Scheme 2). To a dry round bottom flask flushed with nitrogen was added 6-amino-2-napthoic acid (200 mg, 1.07 mmol), NHS (135.18 mg, 1.17 mmol), and dry DMF (2 mL). The reaction mixture was cooled in an ice-bath. EDC-HCl (224.71 mg, 1.17 mmol) was added and the reaction mixture was allowed to react at 0° C. for 30 min, then the reaction was brought up to room temperature and allowed to mix for an additional 3 hrs. The reaction was quenched with the addition of saturated sodium bicarbonate and extracted with EtOAc. The organic layer was dried over MgSO$_4$, filtered, and concentrated for the next step. To a dry round bottom flask flushed with nitrogen was added the NHS-ester of Intermediate Compound (1) (323 mg, 1.13 mmol), which was suspended in dry DMF (4 mL). 4-pentyneamine (292.5 mg, 3.52 mmol) and DIPEA (613 uL, 3.52 mmol) were subsequently added and the reaction mixture was allowed to mix at 75° C. overnight under nitrogen. The reaction was quenched with the addition of saturated sodium bicarbonate and extracted with EtOAc. The organic layer was dried over MgSO$_4$, filtered, and concentrated. Flash column chromatography was used for purification (1:1 EtOAc:Hexanes, 10% MeOH in EtOAc spiked with 1% TEA) to yield 188.2 mg of Intermediate Compound (2) (70% yield). To a dry round bottom flask flushed with nitrogen was added 3-methoxy-5-oxocyclohex-3-9-enecarboxylic acid (115.39 mg, 0.678 mmol), EDC-HCl (194.48 mg, 1.02 mmol), and DMAP (99.4 mg, 0.813 mmol). The flask was sealed under nitrogen. Intermediate Compound (2) (188.2 mg, 0.746 mmol) was resuspended in dry DMF (2 mL) and added to the reaction mixture followed by the addition of TEA (95 μL, 0.678 mmol). The reaction mixture was brought up to 85° C. and allowed to mix overnight under nitrogen. The reaction was quenched with the addition of water and extracted with EtOAc. The organic phases were combined and dried over MgSO$_4$, filtered, and concentrated. Flash column chromatography was used for purification (1:1 Hexanes:EtOAc, 7:3 EtOAc:Hexanes, 5% MeOH in EtOAc) to yield 138.1.6 mg of product (46% yield). In a round bottom flask, Intermediate Compound (3) (138.1 mg, 0.34 mmol) was suspended in a 1:1 Acetonitrile:Water solution (5 mL). 10% CAN (18.8 mg, 0.034 mmol) was added and the reaction mixture was refluxed at 95° C. for 3 hrs., resulting in the synthesis of DYn-Naph (FIG. 5). The reaction was then cooled and concentrated and directly purified by HPLC.

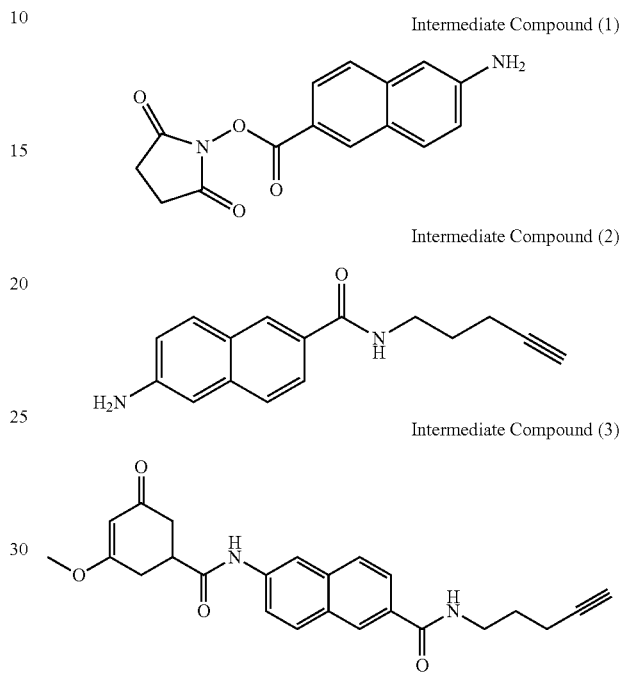

Example 5

Synthesis of Probe Compound, DYn-Bp

DYn-BP (FIG. 5) may be synthesized by the following method (FIG. 6B, Scheme 3). To a dry round bottom flask flushed with nitrogen, was added 4-(4-aminophenyl)benzoic acid (400 mg, 1.88 mmol), NHS (237.4 mg, 1.93 mmol), and dry DMF (2 mL). The reaction mixture was cooled in a ice-bath. EDC-HCl (394.8 mg, 1.93 mmol) was added and the reaction mixture was allowed to react at 0° C. for 30 min, then the reaction was brought up to room temperature and allowed to mix for an additional 3 hrs. The reaction was quenched with the addition of saturated sodium bicarbonate and extracted with EtOAc. The organic layer was dried over MgSO$_4$, filtered, and concentrated for the next step. To a dry round bottom flask flushed with nitrogen, was added the NHS-ester of Intermediate Compound (4) (506.7 mg, 3.26 mmol) which was suspended in dry DMF (4 mL). 4-pentyneamine (271.4 mg, 3.26 mmol) and DIPEA (500 μL, 3.26 mmol) were subsequently added and the reaction mixture was allowed to mix at 75° C. overnight under nitrogen. The reaction was quenched with the addition of saturated sodium bicarbonate and extracted with EtOAc. The organic layer was dried over MgSO$_4$, filtered, and concentrated. Flash column chromatography was used for purification (6:4 Hexanes:EtOAc; 10% MeOH in EtOAc spiked with 1% TEA) to yield 312.1 mg (61.2% yield) of Intermediate Compound (5) for future reactions. To a dry round bottom flask flushed with nitrogen, was added 3-methoxy-5-oxocyclohex-3-9enecarboxylic acid (190.8 mg, 1.12 mmol), EDC-HCl (320.5 mg, 1.68 mmol), and DMAP (205.3 mg, 1.68 mmol). The flask was sealed under nitrogen. Intermediate Compound (5) (312.1 mg, 1.12 mmol) was resuspended in dry DMF (2 mL) and added to the reaction mixture followed by the addition of TEA (250 µL, 1.12 mmol). The reaction mixture was brought up to 85° C. and allowed to mix overnight under nitrogen. The reaction was quenched with the addition of water and extracted with EtOAc. The organic phases were combined and dried over $MgSO_4$, filtered, and concentrated. Flash column chromatography was used for purification (6:4 EtOAc:Hexanes, 8:2 EtOAc:Hexanes, 10% MeOH in EtOAc) to yield 247 mg of product (51.7% yield). In a round bottom flask, Intermediate Compound (6) (247 mg, 0.57 mmol) was suspended in a 1:1 Acetonitrile:Water solution (5 mL). 10% CAN (31.45 mg, 0.057 mmol) was added and the reaction mixture was refluxed at 95° C. for 3 hrs., resulting in the synthesis of DYn-BP. The reaction was then cooled and concentrated and directly purified by HPLC.

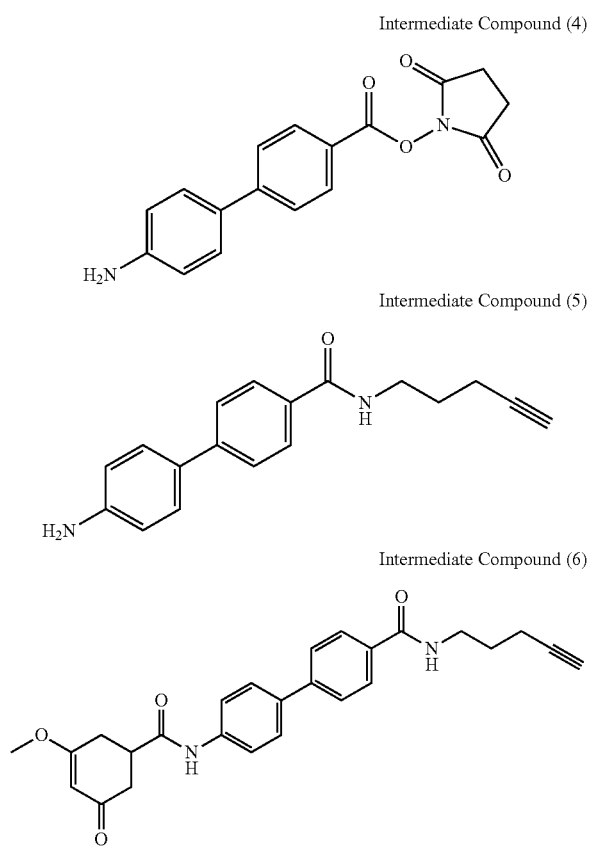

Intermediate Compound (4)

Intermediate Compound (5)

Intermediate Compound (6)

It should be understood, of course, that the foregoing relates to exemplary embodiments of the invention and that modifications may be made without departing from the spirit and scope of the invention as set forth in the following claims.

Aspects of the disclosure can be modified, if necessary, with various configurations, and concepts of the various patents, applications, and publications to provide yet further embodiments of the disclosure.

These and other changes can be made to the disclosure in light of the above-detailed description. In general, in the following claims, the terms used should not be construed to limit the disclosure to the specific embodiments disclosed in the specification and the claims, but should be construed to include all systems and methods that operate in accordance with the claims. Accordingly, the invention is not limited by the disclosure, but instead its scope is to be determined broadly by the following claims.

What is claimed is:

1. A compound for modifying the activity of a protein phosphatase, wherein the protein phosphatase comprises a redox-sensitive cysteine, the compound comprising a nucleophilic warhead wherein the warhead can form a covalent bond with a sulfenic acid-modified or sulfenamide-modified form of the redox-sensitive cysteine; and a binding module;

wherein the compound is of one of the following formulas:

Formula TDZ-11:

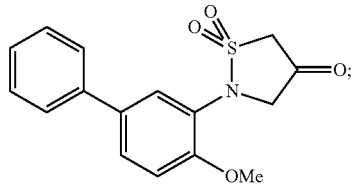 [SMILES: COc1ccc(-c2ccccc2)cc1N1CC(=O)CS1(=O)=O]

Formula IX:

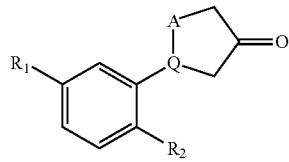

wherein:
A is a carbonyl group or a sulfonyl group;
Q is a carbon atom or a nitrogen atom;
$R_1$ is a hydrogen atom or any straight, branched, or cyclic alkyl functional group; and
$R_2$ is a hydrogen atom or any straight, branched or cyclic alkyl functional group;

or,

Formula XI:

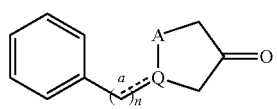

wherein:
A is a carbonyl group or a sulfonyl group;
Q is a carbon atom or a nitrogen atom;
a is a single bond or a double bond; and
n is 0 or 1.

2. A method of modifying the activity of a protein phosphatase, comprising:
exposing the protein to a compound of claim 1.

3. A method of treating diabetes in a subject, comprising:
administering to a subject afflicted with a disease, a therapeutically effective amount of a compound, wherein the compound is any one of the compounds of claim 1.

4. The compound of claim 1, wherein for the compound of formula (IX), A is a sulfonyl group.

5. The compound of claim 1, wherein for the compound of formula (IX), Q is a nitrogen atom.

6. The compound of claim 1, wherein for the compound of formula (XI), Q is a carbon atom.

7. The compound of claim 1, wherein for the compound of formula (XI), a is a double bond.

8. The compound of claim 1, wherein for the compound of formula (XI), A is a sulfonyl group.

9. The method of claim 2, wherein the phosphatase is PTP1B.

* * * * *